(12) United States Patent
Ye et al.

(10) Patent No.: US 8,741,591 B2
(45) Date of Patent: Jun. 3, 2014

(54) PH-INSENSITIVE GLUCOSE INDICATOR PROTEIN

(75) Inventors: Kaiming Ye, Fayetteville, AR (US); Sha Jin, Fayetteville, AR (US)

(73) Assignee: The Research Foundation for The State University of New York, Binghamton, NY (US)

( * ) Notice: Subject to any disclaimer, the term of this patent is extended or adjusted under 35 U.S.C. 154(b) by 467 days.

(21) Appl. No.: 12/902,725

(22) Filed: Oct. 12, 2010

(65) Prior Publication Data
US 2011/0091919 A1 Apr. 21, 2011

Related U.S. Application Data

(60) Provisional application No. 61/250,118, filed on Oct. 9, 2009.

(51) Int. Cl.
*C12Q 1/54* (2006.01)
*C07K 14/00* (2006.01)

(52) U.S. Cl.
USPC .............................................. 435/14; 530/350

(58) Field of Classification Search
None
See application file for complete search history.

(56) References Cited

U.S. PATENT DOCUMENTS

| 4,703,756 | A | 11/1987 | Gough |
| 4,919,141 | A | 4/1990 | Zeir |
| 5,372,133 | A | 12/1994 | Hogen Esch |
| 5,593,852 | A | 1/1997 | Heller |
| 2005/0112685 | A1* | 5/2005 | Amiss et al. .................... 435/7.1 |
| 2005/0118726 | A1* | 6/2005 | Schultz et al. ................. 436/518 |
| 2007/0136825 | A1* | 6/2007 | Frommer et al. .................. 800/3 |
| 2008/0213811 | A1* | 9/2008 | Vogel et al. ...................... 435/15 |

OTHER PUBLICATIONS

Geddes, Review in Fluorescence (2002).

* cited by examiner

*Primary Examiner* — Lisa J Hobbs
(74) *Attorney, Agent, or Firm* — Steven M. Hoffberg; Ostrolenk Faber LLP

(57) ABSTRACT

The present invention encompasses a glucose indicator protein, a biosensor comprising one or more glucose indicator proteins, and methods of use thereof.

10 Claims, 47 Drawing Sheets
(17 of 47 Drawing Sheet(s) Filed in Color)

Leader peptide cleavage site

A leader peptide signal sequence

MNKKVLTLSAVMASMLFGAAAHAADTRIGVTIYKVDDNFMSVVRKAIEQDAKAAPDVQLLMNDSQNDQSKQND
QIDVLLAKGVKALAINLVDPAAAGTVIEKARGQNVPVVFNKEPSRKALDSYDKAYYVGTDSKESGHQGDLIAKHW
AANQGWDLNKDGQQFVLLKGEPGGHPDAEARTTYVIKELNDKGIKTEQLQLDTAMWDTAQAKDRMDAWLSGPNA
NKIEVVIANNDAMAMGAVEALKAHNKSSIPVFGVDALPEALALVKSGALAGTVLNDANNQAKATFDLAKNLADGK
GAADGTNWKIDNKVVRWPYVGVDKIDNLAEFSKK*

FIG. 1

A
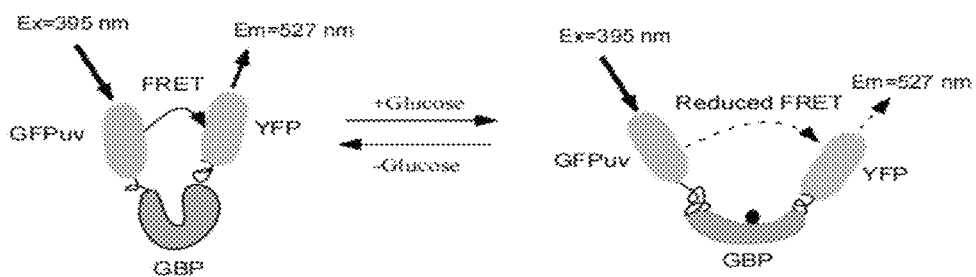
B
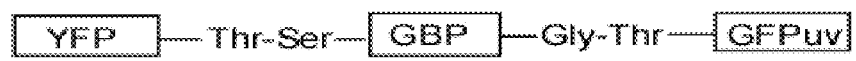
C
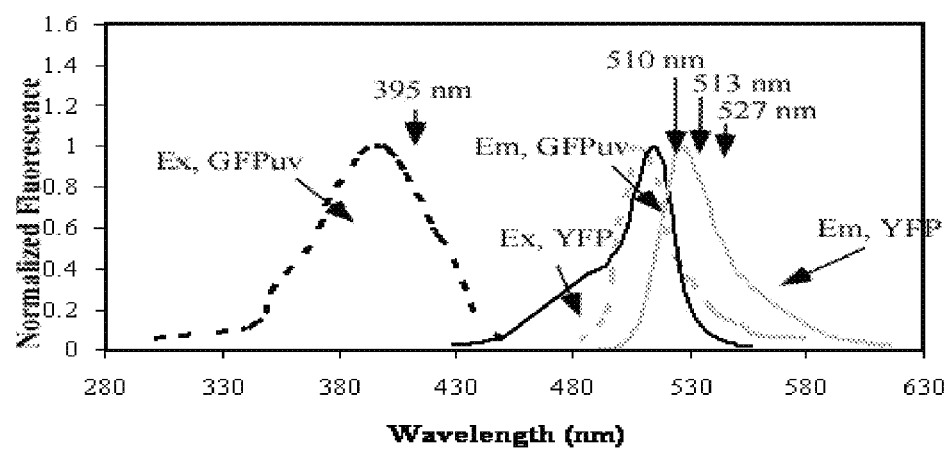
FIG. 3

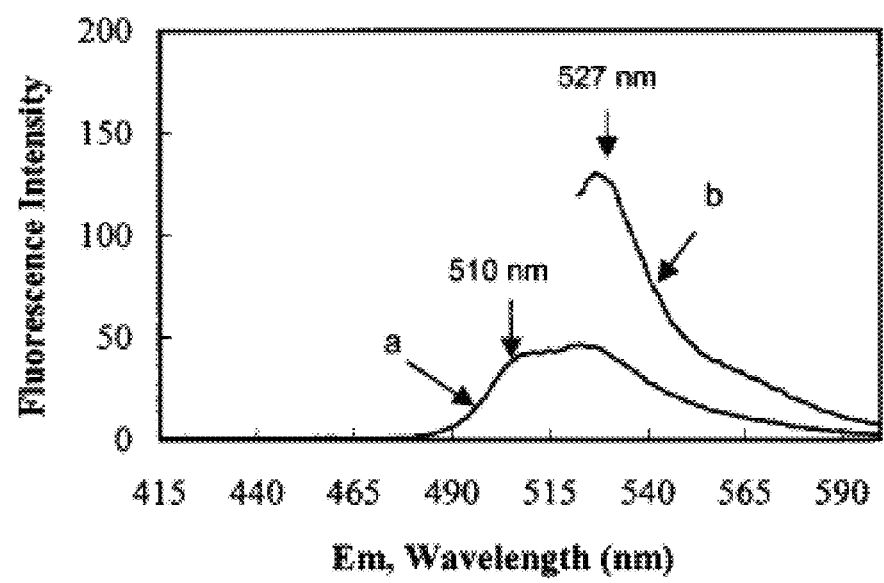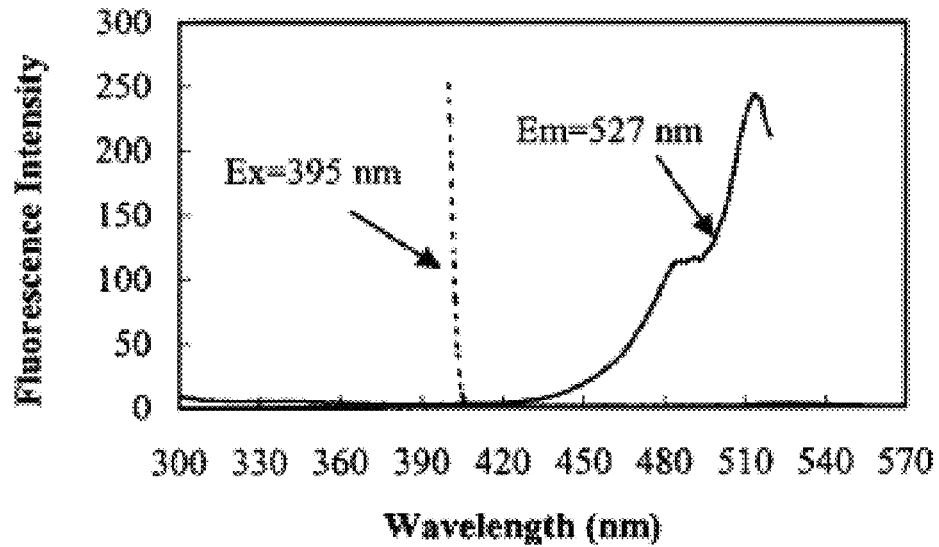
FIG. 4

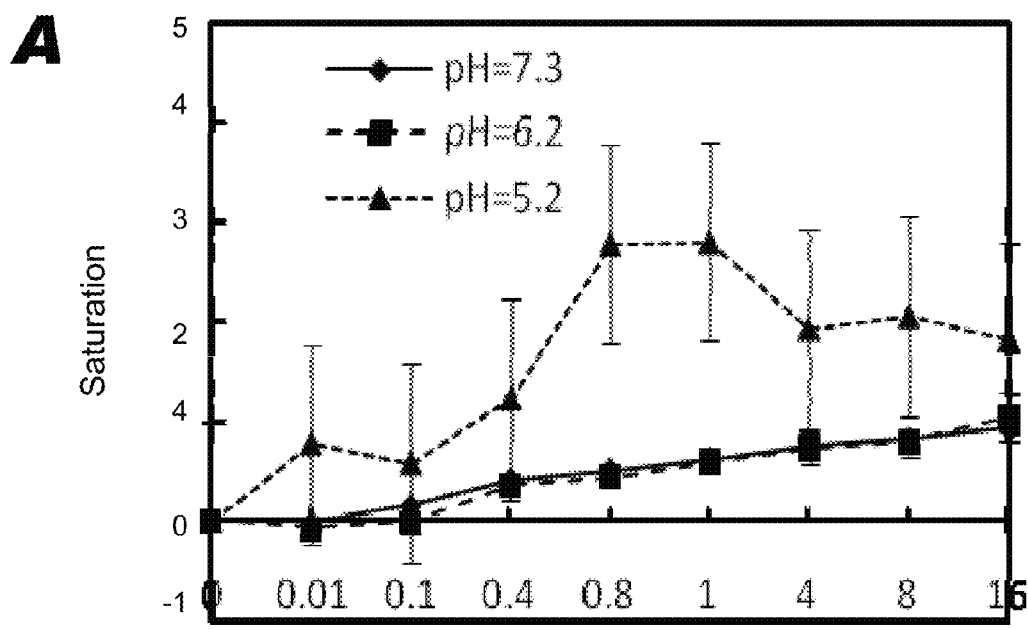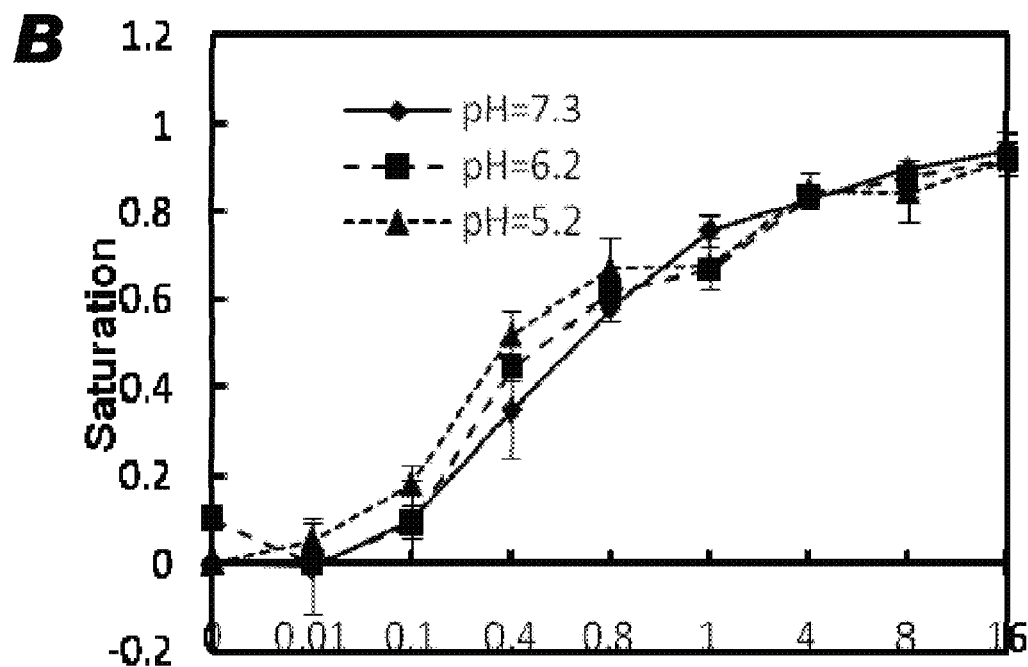
FIG. 9

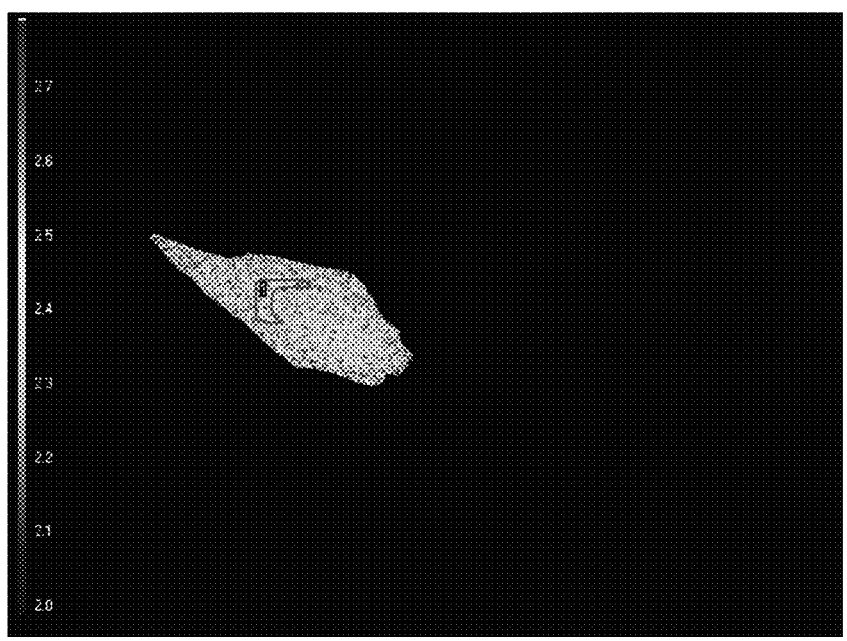
FIG. 14

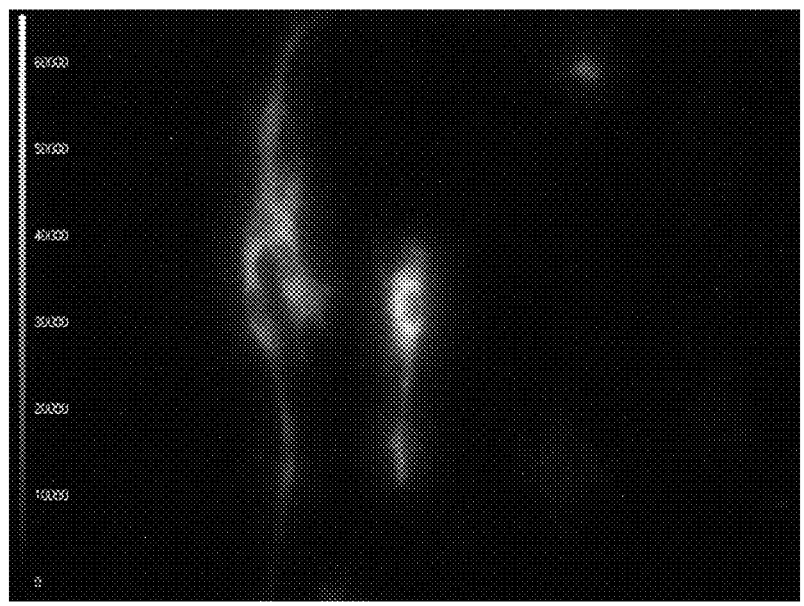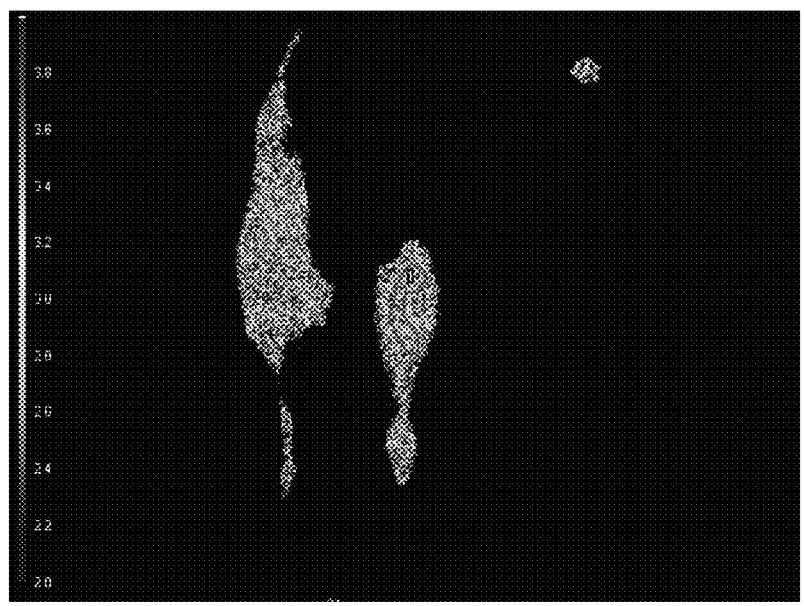
FIG. 15

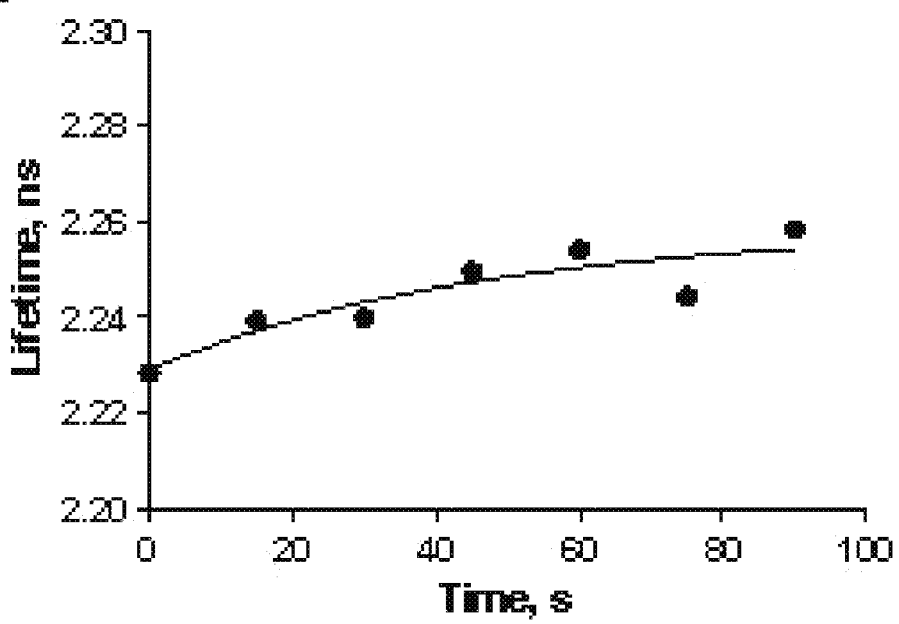
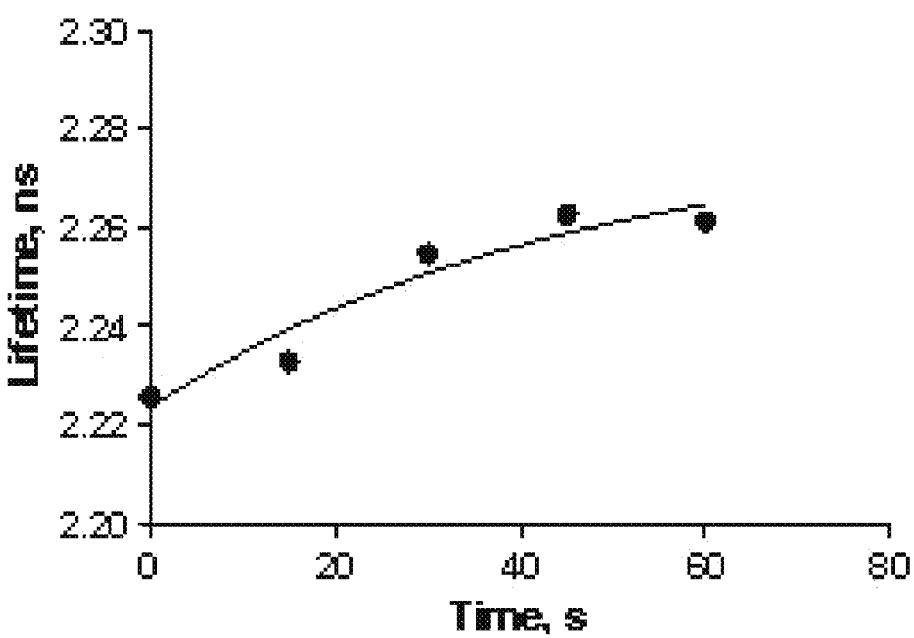
FIG. 20

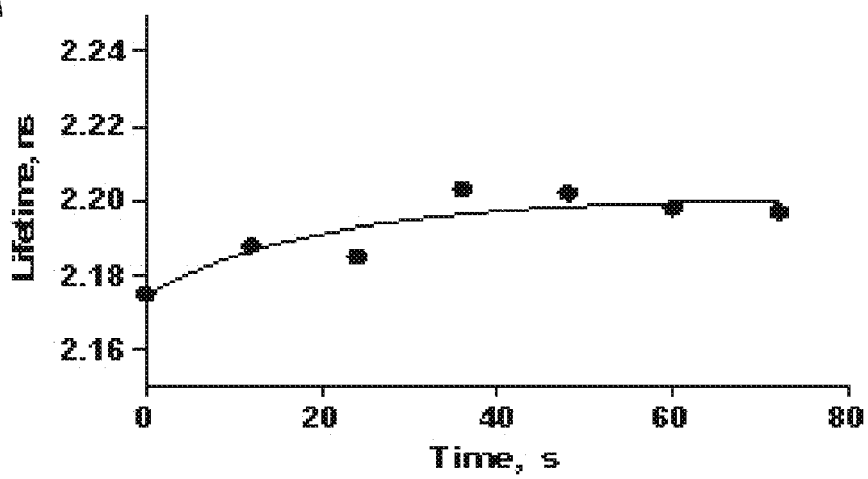
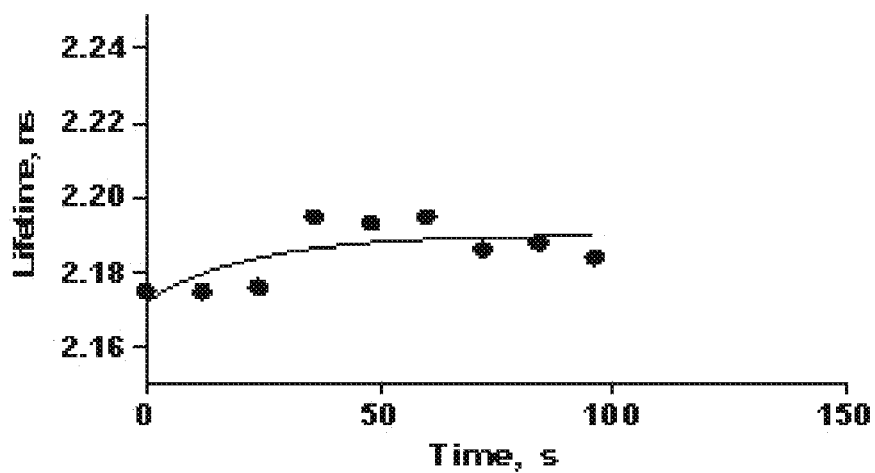
FIG. 25

FIG. 26 - Sequence of GIP$_r$-Thr

```
ATGGTGAGCAAGGGCGAGGAGCTGTTCACCGGGGTGGTGCCCATCCTGGTCGAGCTGGA
CGGCGACGTAAACGGCCACAAGTTCAGCGTGTCCGGCGAGGGCGAGGGCGATGCCACC
TACGGCAAGCTGACCCTGAAGTTCATCTGCACCACCGGCAAGCTGCCCGTGCCCTGGCC
CACCCTCGTGACCACCCTGACCTGGGGCGTGCAGTGCTTCAGCCGCTACCCCGACCACA
TGAAGCAGCACGACTTCTTCAAGTCCGCCATGCCCGAAGGCTACGTCCAGGAGCGCACCA
TCTTCTTCAAGGACGACGGCAACTACAAGACCCGCGCCGAGGTGAAGTTCGAGGGCGAC
ACCCTGGTGAACCGCATCGAGCTGAAGGGCATCGACTTCAAGGAGGACGGCAACATCCT
GGGGCACAAGCTGGAGTACAACTACATCAGCCACAACGTCTATATCACCGCCGACAAGCA
GAAGAACGGCATCAAGGCCAACTTCAAGATCCGCCACAACATCGAGGACGGCAGCGTGC
AGCTCGCCGACCACTACCAGCAGAACACCCCCATCGGCGACGGCCCCGTGCTGCTGCCC
GACAACCACTACCTGAGCACCCAGTCCGCCCTGAGCAAAGACCCCAACGAGAAGCGCGA
TCACATGGTCCTGCTGGAGTTCGTGACCGCCGCCGGGATCACTCTCGGCATGGACGAGC
TGTACAAGGGTACCGGTGGTACCGGAGGCGCCGCTGATACTCGCATTGGTGTAACAATCT
ATAAGTACGACGATAACACTATGTCTGTAGTGCGCAAGGCTATTGAGCAAGATGCGAAAGC
CGCGCCAGATGTTCAGCTGCTGATGAATGATTCTCAGAATGACCAGTCCAAGCAGAACGA
TCAGATCGACGTATTGCTGGCGAAAGGGGTGAAGGCACTGGCAATCAACCTGGTTGACCC
GGCAGCTGCGGGTACGGTGATTGAGAAGCGCGTGGGCAAAACGTGCCGGTGGTTTTCT
TCAACAAAGAACCGTCTCGTAAGGCGCTGGATAGCTACGACAAAGCCTACTACGTTGGCA
CTGACTCCAAAGAGTCCGGCATTATTCAAGGCGATTTGATTGCTAAACACTGGGCGGCGA
ATCAGGGTTGGGATCTGAACAAAGACGGTCAGATTCAGTTCGTACTGCTGAAAGGTGAAC
CGGGCCATCCGGATGCAGAAGCACGTACCACTTACGTGATTAAAGAATTGAACGATAAAG
GCATCAAAACTGAACAGTTACAGTTAGATACCGCAATGTGGGACACCGCTCAGGCGAAAG
ATAAGATGGACGCCTGGCTGTCTGGCCCGAACGCCAACAAAATCGAAGTGGTTATCGCCA
ACAACGATGCGATGGCAATGGGCGCGGTTGAAGCGCTGAAAGCACACAACAAGTCCAGC
ATTCCGGTGTTTGGCGTCGATGCGCTGCCAGAAGCGCTGGCGCTGGTGAAATCCGGTGC
ACTGGCGGGCACCGTACTGAACGATGCTAACAACCAGGCGAAAGCGACCTTTGATCTGGC
GAAAAACCTGGCCGATGGTAAAGGTGCGGCTGATGGCACCAACTGGAAAATCGACAACAA
AGTGGTCCGCGTACCTTATGTTGGCGTAGATAAAGACAACCTGGCTGAATTCAGCAAGAAA
GGCGCCGGTACCGGTGGACTAGTAGTGAGCAAGGGCGAGGAGCTGTTCACCGGGGTGG
TGCCCATCCTGGTCGAGCTGGACGGCGACGTAAACGGCCACAAGTTCAGCGTGTCCGGC
GAGGGCGAGGGCGATGCCACCTACGGCAAGCTGACCCTGAAGTTCATCTGCACCACCGG
CAAGCTGCCCGTGCCCTGGCCCACCCTCGTGACCACCTTCGGCTACGGCCTGATGTGCTT
CGCCCGCTACCCCGACCACATGAAGCAGCACGACTTCTTCAAGTCCGCCATGCCCGAAG
GCTACGTCCAGGAGCGCACCATCTTCTTCAAGGACGACGGCAACTACAAGACCCGCGCC
GAGGTGAAGTTCGAGGGCGACACCCTGGTGAACCGCATCGAGCTGAAGGGCATCGACTT
CAAGGAGGACGGCAACATCCTGGGGCACAAGCTGGAGTACAACTACAACAGCCACAACG
TCTATATCATGGCCGACAAGCAGAAGAACGGCATCAAGGTGAACTTCAAGATCCGCCACA
ACATCGAGGACGGCAGCGTGCAGCTCGCCGACCACTACCAGCAGAACACCCCCATCGGC
GACGGCCCCGTGCTGCTGCCCGACAACCACTACCTGAGCTACCAGTCCGCCCTGAGCAA
AGACCCCAACGAGAAGCGCGATCACATGGTCCTGCTGGAGTTCGTGACCGCCGCCGGGA
TCACTCTCGGCATGGACGAGCTGTACAAGCAAGCTTACGTAGAACAAAAACTCATCTCAGA
AGAGGATCTGAATAGCGCCGTCGACCATCATCATCATCATCATTGA
```

FIG. 27 - *Sequence of GIP$_f$-Cys*

ATGGTGAGCAAGGGCGAGGAGCTGTTCACCGGGGTGGTGCCCATCCTGGTCGAGCTGGA
CGGCGACGTAAACGGCCACAAGTTCAGCGTGTCCGGCGAGGGCGAGGGCGATGCCACCT
ACGGCAAGCTGACCCTGAAGTTCATCTGCACCACCGGCAAGCTGCCCGTGCCCTGGCCCA
CCCTCGTGACCACCCTGACCTGGGGCGTGCAGTGCTTCAGCCGCTACCCCGACCACATGA
AGCAGCACGACTTCTTCAAGTCCGCCATGCCCGAAGGCTACGTCCAGGAGCGCACCATCT
TCTTCAAGGACGACGGCAACTACAAGACCCGCGCCGAGGTGAAGTTCGAGGGCGACACC
CTGGTGAACCGCATCGAGCTGAAGGGCATCGACTTCAAGGAGGACGGCAACATCCTGGG
GCACAAGCTGGAGTACAACTACATCAGCCACAACGTCTATATCACCGCCGACAAGCAGAA
GAACGGCATCAAGGCCAACTTCAAGATCCGCCACAACATCGAGGACGGCAGCGTGCAGCT
CGCCGACCACTACCAGCAGAACACCCCCATCGGCGACGGCCCCGTGCTGCTGCCCGACA
ACCACTACCTGAGCACCCAGTCCGCCCTGAGCAAAGACCCCAACGAGAAGCGCGATCACA
TGGTCCTGCTGGAGTTCGTGACCGCCGCCGGGATCACTCTCGGCATGGACGAGCTGTACA
AGGGTACCGGTGGTACCGGAGGCGCCGCTGATACTCGCATTGGTGTAACAATCTATAAGT
ACGACGATAACTGTATGTCTGTAGTGCGCAAGGCTATTGAGCAAGATGCGAAAGCCGCGC
CAGATGTTCAGCTGCTGATGAATGATTCTCAGAATGACCAGTCCAAGCAGAACGATCAGAT
CGACGTATTGCTGGCGAAAGGGGTGAAGGCACTGGCAATCAACCTGGTTGACCCGGCAG
CTGCGGGTACGGTGATTGAGAAAGCGCGTGGGCAAAACGTGCCGGTGGTTTTCTTCAACA
AAGAACCGTCTCGTAAGGCGCTGGATAGCTACGACAAAGCCTACTACGTTGGCACTGACT
CCAAAGAGTCCGGCATTATTCAAGGCGATTTGATTGCTAAACACTGGGCGGCGAATCAGG
GTTGGGATCTGAACAAAGACGGTCAGATTCAGTTCGTACTGCTGAAAGGTGAACCGGGCC
ATCCGGATGCAGAAGCACGTACCACTTACGTGATTAAAGAATTGAACGATAAAGGCATCAA
AACTGAACAGTTACAGTTAGATACCGCAATGTGGGACACCGCTCAGGCGAAAGATAAGATG
GACGCCTGGCTGTCTGGCCCGAACGCCAACAAAATCGAAGTGGTTATCGCCAACAACGAT
GCGATGGCAATGGGCGCGGTTGAAGCGCTGAAAGCACACAACAAGTCCAGCATTCCGGT
GTTTGGCGTCGATGCGCTGCCAGAAGCGCTGGCGCTGGTGAAATCCGGTGCACTGGCGG
GCACCGTACTGAACGATGCTAACAACCAGGCGAAAGCGACCTTTGATCTGGCGAAAAACC
TGGCCGATGGTAAAGGTGCGGCTGATGGCACCAACTGGAAAATCGACAACAAAGTGGTCC
GCGTACCTTATGTTGGCGTAGATAAAGACAACCTGGCTGAATTCAGCAAGAAAGGCGCCG
GTACCGGTGGACTAGTAGTGAGCAAGGGCGAGGAGCTGTTCACCGGGGTGGTGCCCATC
CTGGTCGAGCTGGACGGCGACGTAAACGGCCACAAGTTCAGCGTGTCCGGCGAGGGCGA
GGGCGATGCCACCTACGGCAAGCTGACCCTGAAGTTCATCTGCACCACCGGCAAGCTGCC
CGTGCCCTGGCCCACCCTCGTGACCACCTTCGGCTACGGCCTGATGTGCTTCGCCCGCTA
CCCCGACCACATGAAGCAGCACGACTTCTTCAAGTCCGCCATGCCCGAAGGCTACGTCCA
GGAGCGCACCATCTTCTTCAAGGACGACGGCAACTACAAGACCCGCGCCGAGGTGAAGTT
CGAGGGCGACACCCTGGTGAACCGCATCGAGCTGAAGGGCATCGACTTCAAGGAGGACG
GCAACATCCTGGGGCACAAGCTGGAGTACAACTACAACAGCCACAACGTCTATATCATGG
CCGACAAGCAGAAGAACGGCATCAAGGTGAACTTCAAGATCCGCCACAACATCGAGGACG
GCAGCGTGCAGCTCGCCGACCACTACCAGCAGAACACCCCCATCGGCGACGGCCCCGTG
CTGCTGCCCGACAACCACTACCTGAGCTACCAGTCCGCCCTGAGCAAAGACCCCAACGAG
AAGCGCGATCACATGGTCCTGCTGGAGTTCGTGACCGCCGCCGGGATCACTCTCGGCATG
GACGAGCTGTACAAGCAAGCTTACGTAGAACAAAAACTCATCTCAGAAGAGGATCTGAATA
GCGCCGTCGACCATCATCATCATCATCATTGA

**FIG. 28 - *Sequence of GIP<sub>i</sub>-Leu***

```
ATGGTGAGCAAGGGCGAGGAGCTGTTCACCGGGGTGGTGCCCATCCTGGTCGAGCTGGA
CGGCGACGTAAACGGCCACAAGTTCAGCGTGTCCGGCGAGGGCGAGGGCGATGCCACCT
ACGGCAAGCTGACCCTGAAGTTCATCTGCACCACCGGCAAGCTGCCCGTGCCCTGGCCCA
CCCTCGTGACCACCCTGACCTGGGGCGTGCAGTGCTTCAGCCGCTACCCCGACCACATGA
AGCAGCACGACTTCTTCAAGTCCGCCATGCCCGAAGGCTACGTCCAGGAGCGCACCATCT
TCTTCAAGGACGACGGCAACTACAAGACCCGCGCCGAGGTGAAGTTCGAGGGCGACACC
CTGGTGAACCGCATCGAGCTGAAGGGCATCGACTTCAAGGAGGACGGCAACATCCTGGG
GCACAAGCTGGAGTACAACTACATCAGCCACAACGTCTATATCACCGCCGACAAGCAGAA
GAACGGCATCAAGGCCAACTTCAAGATCCGCCACAACATCGAGGACGGCAGCGTGCAGCT
CGCCGACCACTACCAGCAGAACACCCCCATCGGCGACGGCCCCGTGCTGCTGCCCGACA
ACCACTACCTGAGCACCCAGTCCGCCCTGAGCAAAGACCCCAACGAGAAGCGCGATCACA
TGGTCCTGCTGGAGTTCGTGACCGCCGCCGGGATCACTCTCGGCATGGACGAGCTGTACA
AGGGTACCGGTGGTACCGGAGGCGCCGCTGATACTCGCATTGGTGTAACAATCTATAAGT
ACGACGATAACTTGATGTCTGTAGTGCGCAAGGCTATTGAGCAAGATGCGAAAGCCGCGC
CAGATGTTCAGCTGCTGATGAATGATTCTCAGAATGACCAGTCCAAGCAGAACGATCAGAT
CGACGTATTGCTGGCGAAAGGGGTGAAGGCACTGGCAATCAACCTGGTTGACCCGGCAG
CTGCGGGTACGGTGATTGAGAAAGCGCGTGGGCAAAACGTGCCGGTGGTTTTCTTCAACA
AAGAACCGTCTCGTAAGGCGCTGGATAGCTACGACAAAGCCTACTACGTTGGCACTGACT
CCAAAGAGTCCGGCATTATTCAAGGCGATTTGATTGCTAAACACTGGGCGGCGAATCAGG
GTTGGGATCTGAACAAAGACGGTCAGATTCAGTTCGTACTGCTGAAAGGTGAACCGGGCC
ATCCGGATGCAGAAGCACGTACCACTTACGTGATTAAAGAATTGAACGATAAAGGCATCAA
AACTGAACAGTTACAGTTAGATACCGCAATGTGGGACACCGCTCAGGCGAAAGATAAGATG
GACGCCTGGCTGTCTGGCCCGAACGCCAACAAAATCGAAGTGGTTATCGCCAACAACGAT
GCGATGGCAATGGGCGCGGTTGAAGCGCTGAAAGCACACAACAAGTCCAGCATTCCGGT
GTTTGGCGTCGATGCGCTGCCAGAAGCGCTGGCGCTGGTGAAATCCGGTGCACTGGCGG
GCACCGTACTGAACGATGCTAACAACCAGGCGAAAGCGACCTTTGATCTGGCGAAAAACC
TGGCCGATGGTAAAGGTGCGGCTGATGGCACCAACTGGAAAATCGACAACAAAGTGGTCC
GCGTACCTTATGTTGGCGTAGATAAAGACAACCTGGCTGAATTCAGCAAGAAAGGCGCCG
GTACCGGTGGACTAGTAGTGAGCAAGGGCGAGGAGCTGTTCACCGGGGTGGTGCCCATC
CTGGTCGAGCTGGACGGCGACGTAAACGGCCACAAGTTCAGCGTGTCCGGCGAGGGCGA
GGGCGATGCCACCTACGGCAAGCTGACCCTGAAGTTCATCTGCACCACCGGCAAGCTGCC
CGTGCCCTGGCCCACCCTCGTGACCACCTTCGGCTACGGCCTGATGTGCTTCGCCCGCTA
CCCCGACCACATGAAGCAGCACGACTTCTTCAAGTCCGCCATGCCCGAAGGCTACGTCCA
GGAGCGCACCATCTTCTTCAAGGACGACGGCAACTACAAGACCCGCGCCGAGGTGAAGTT
CGAGGGCGACACCCTGGTGAACCGCATCGAGCTGAAGGGCATCGACTTCAAGGAGGACG
GCAACATCCTGGGGCACAAGCTGGAGTACAACTACAACAGCCACAACGTCTATATCATGG
CCGACAAGCAGAAGAACGGCATCAAGGTGAACTTCAAGATCCGCCACAACATCGAGGACG
GCAGCGTGCAGCTCGCCGACCACTACCAGCAGAACACCCCCATCGGCGACGGCCCCGTG
CTGCTGCCCGACAACCACTACCTGAGCTACCAGTCCGCCCTGAGCAAAGACCCCAACGAG
AAGCGCGATCACATGGTCCTGCTGGAGTTCGTGACCGCCGCCGGGATCACTCTCGGCATG
GACGAGCTGTACAAGCAAGCTTACGTAGAACAAAAACTCATCTCAGAAGAGGATCTGAATA
GCGCCGTCGACCATCATCATCATCATCATTGA
```

**FIG. 29 - *Sequence of GIP$_i$-Val***

```
ATGGTGAGCAAGGGCGAGGAGCTGTTCACCGGGGTGGTGCCCATCCTGGTCGAGCTGGA
CGGCGACGTAAACGGCCACAAGTTCAGCGTGTCCGGCGAGGGCGAGGGCGATGCCACCT
ACGGCAAGCTGACCCTGAAGTTCATCTGCACCACCGGCAAGCTGCCCGTGCCCTGGCCCA
CCCTCGTGACCACCCTGACCTGGGGCGTGCAGTGCTTCAGCCGCTACCCCGACCACATGA
AGCAGCACGACTTCTTCAAGTCCGCCATGCCCGAAGGCTACGTCCAGGAGCGCACCATCT
TCTTCAAGGACGACGGCAACTACAAGACCCGCGCCGAGGTGAAGTTCGAGGGCGACACC
CTGGTGAACCGCATCGAGCTGAAGGGCATCGACTTCAAGGAGGACGGCAACATCCTGGG
GCACAAGCTGGAGTACAACTACATCAGCCACAACGTCTATATCACCGCCGACAAGCAGAA
GAACGGCATCAAGGCCAACTTCAAGATCCGCCACAACATCGAGGACGGCAGCGTGCAGCT
CGCCGACCACTACCAGCAGAACACCCCCATCGGCGACGGCCCCGTGCTGCTGCCCGACA
ACCACTACCTGAGCACCCAGTCCGCCCTGAGCAAAGACCCCAACGAGAAGCGCGATCACA
TGGTCCTGCTGGAGTTCGTGACCGCCGCCGGGATCACTCTCGGCATGGACGAGCTGTACA
AGGGTACCGGTGGTACCGGAGGCGCCGCTGATACTCGCATTGGTGTAACAATCTATAAGT
ACGACGATAACGTTATGTCTGTAGTGCGCAAGGCTATTGAGCAAGATGCGAAAGCCGCGC
CAGATGTTCAGCTGCTGATGAATGATTCTCAGAATGACCAGTCCAAGCAGAACGATCAGAT
CGACGTATTGCTGGCGAAAGGGGTGAAGGCACTGGCAATCAACCTGGTTGACCCGGCAG
CTGCGGGTACGGTGATTGAGAAAGCGCGTGGGCAAAACGTGCCGGTGGTTTTCTTCAACA
AAGAACCGTCTCGTAAGGCGCTGGATAGCTACGACAAAGCCTACTACGTTGGCACTGACT
CCAAAGAGTCCGGCATTATTCAAGGCGATTTGATTGCTAAACACTGGGCGGCGAATCAGG
GTTGGGATCTGAACAAAGACGGTCAGATTCAGTTCGTACTGCTGAAAGGTGAACCGGGCC
ATCCGGATGCAGAAGCACGTACCACTTACGTGATTAAAGAATTGAACGATAAAGGCATCAA
AACTGAACAGTTACAGTTAGATACCGCAATGTGGGACACCGCTCAGGCGAAAGATAAGATG
GACGCCTGGCTGTCTGGCCCGAACGCCAACAAAATCGAAGTGGTTATCGCCAACAACGAT
GCGATGGCAATGGGCGCGGTTGAAGCGCTGAAAGCACACAACAAGTCCAGCATTCCGGT
GTTTGGCGTCGATGCGCTGCCAGAAGCGCTGGCGCTGGTGAAATCCGGTGCACTGGCGG
GCACCGTACTGAACGATGCTAACAACCAGGCGAAAGCGACCTTTGATCTGGCGAAAAACC
TGGCCGATGGTAAAGGTGCGGCTGATGGCACCAACTGGAAAATCGACAACAAAGTGGTCC
GCGTACCTTATGTTGGCGTAGATAAAGACAACCTGGCTGAATTCAGCAAGAAAGGCGCCG
GTACCGGTGGACTAGTAGTGAGCAAGGGCGAGGAGCTGTTCACCGGGGTGGTGCCCATC
CTGGTCGAGCTGGACGGCGACGTAAACGGCCACAAGTTCAGCGTGTCCGGCGAGGGCGA
GGGCGATGCCACCTACGGCAAGCTGACCCTGAAGTTCATCTGCACCACCGGCAAGCTGCC
CGTGCCCTGGCCCACCCTCGTGACCACCTTCGGCTACGGCCTGATGTGCTTCGCCCGCTA
CCCCGACCACATGAAGCAGCACGACTTCTTCAAGTCCGCCATGCCCGAAGGCTACGTCCA
GGAGCGCACCATCTTCTTCAAGGACGACGGCAACTACAAGACCCGCGCCGAGGTGAAGTT
CGAGGGCGACACCCTGGTGAACCGCATCGAGCTGAAGGGCATCGACTTCAAGGAGGACG
GCAACATCCTGGGGCACAAGCTGGAGTACAACTACAACAGCCACAACGTCTATATCATGG
CCGACAAGCAGAAGAACGGCATCAAGGTGAACTTCAAGATCCGCCACAACATCGAGGACG
GCAGCGTGCAGCTCGCCGACCACTACCAGCAGAACACCCCCATCGGCGACGGCCCCGTG
CTGCTGCCCGACAACCACTACCTGAGCTACCAGTCCGCCCTGAGCAAAGACCCCAACGAG
AAGCGCGATCACATGGTCCTGCTGGAGTTCGTGACCGCCGCCGGGATCACTCTCGGCATG
GACGAGCTGTACAAGCAAGCTTACGTAGAACAAAAACTCATCTCAGAAGAGGATCTGAATA
GCGCCGTCGACCATCATCATCATCATCATTGA
```

FIG. 30 - *Sequence of a plasmid encoding the GIP: AcGFP-GBPval-mCherry*

```
GTTTGACAGCTTATCATCGACTGCACGGTGCACCAATGCTTCTGGCGTCAGGCAGCCATC
GGAAGCTGTGGTATGGCTGTGCAGGTCGTAAATCACTGCATAATTCGTGTCGCTCAAGGC
GCACTCCCGTTCTGGATAATGTTTTTTGCGCCGACATCATAACGGTTCTGGCAAATATTCTG
AAATGAGCTGTTGACAATTAATCATCCGGCTCGTATAATGTGTGGAATTGTGAGCGGATAA
CAATTTCACACAGGAAACAGCGCCGCTGAGAAAAAGCGAAGCGGCACTGCTCTTTAACAAT
TTATCAGACAATCTGTGTGGGCACTCGACCGGAATTATCGATTAACTTTATTATTAAAAATTA
AAGAGGTATATATTAATGTATCGATTAAATAAGGAGGAATAAACCATGGTGAGCAAGGGCG
CCGAGCTGTTCACCGGCATCGTGCCCATCCTGATCGAGCTGAATGGCGATGTGAATGGCC
ACAAGTTCAGCGTGAGCGGCGAGGGCGAGGGCGATGCCACCTACGGCAAGCTGACCCTG
AAGTTCATCTGCACCACCGGCAAGCTGCCTGTGCCCTGGCCCACCCTGGTGACCACCCTG
AGCTACGGCGTGCAGTGCTTCTCACGCTACCCCGATCACATGAAGCAGCACGACTTCTTC
AAGAGCGCCATGCCTGAGGGCTACATCCAGGAGCGCACCATCTTCTTCGAGGATGACGGC
AACTACAAGTCGCGCGCCGAGGTGAAGTTCGAGGGCGATACCCTGGTGAATCGCATCGAG
CTGACCGGCACCGATTTCAAGGAGGATGGCAACATCCTGGGCAATAAGATGGAGTACAAC
TACAACGCCCACAATGTGTACATCATGACCGACAAGGCCAAGAATGGCATCAAGGTGAACT
TCAAGATCCGCCACAACATCGAGGATGGCAGCGTGCAGCTGGCCGACCACTACCAGCAGA
ATACCCCCATCGGCGATGGCCCTGTGCTGCTGCCCGATAACCACTACCTGTCCACCCAGA
GCGCCCTGTCCAAGGACCCCAACGAGAAGCGCGATCACATGATCTACTTCGGCTTCGTGA
CCGCCGCCGCCATCACCCACGGCATGGATGAGCTGTACAAGTCCGGAGCTGATACTCGCA
TTGGTGTAACAATCTATAAGTACGACGATAACGTTATGTCTGTAGTGCGCAAGGCTATTGA
GCAAGATGCGAAAGCCGCGCCAGATGTTCAGCTGCTGATGAATGATTCTCAGAATGACCA
GTCCAAGCAGAACGATCAGATCGACGTATTGCTGGCGAAAGGGGTGAAGGCACTGGCAAT
CAACCTGGTTGACCCGGCAGCTGCGGGTACGGTGATTGAGAAAGCGCGTGGGCAAAACG
TGCCGGTGGTTTTCTTCAACAAAGAACCGTCTCGTAAGGCGCTGGATAGCTACGACAAAGC
CTACTACGTTGGCACTGACTCCAAAGAGTCCGGCATTATTCAAGGCGATTTGATTGCTAAA
CACTGGGCGGCGAATCAGGGTTGGGATCTGAACAAAGACGGTCAGATTCAGTTCGTACTG
CTGAAAGGTGAACCGGGCCATCCGGATGCAGAAGCACGTACCACTTACGTGATTAAAGAA
TTGAACGATAAAGGCATCAAAACTGAACAGTTACAGTTAGATACCGCAATGTGGGACACCG
CTCAGGCGAAAGATAAGATGGACGCCTGGCTGTCTGGCCCGAACGCCAACAAATCGAAG
TGGTTATCGCCAACAACGATGCGATGGCAATGGGCGCGGTTGAAGCGCTGAAAGCACACA
ACAAGTCCAGCATTCCGGTGTTTGGCGTCGATGCGCTGCCAGAAGCGCTGGCGCTGGTGA
AATCCGGTGCACTGGCGGGCACCGTACTGAACGATGCTAACAACCAGGCGAAAGCGACCT
TTGATCTGGCGAAAAACCTGGCCGATGGTAAAGGTGCGGCTGATGGCACCAACTGGAAAA
TCGACAACAAAGTGGTCCGCGTACCTTATGTTGGCGTAGATAAAGACAACCTGGCTGAATT
CAGCAAGAAAATGATGGTGAGCAAGGGCGAGGAGGATAACATGGCCATCATCAAGGAGTT
CATGCGCTTCAAGGTGCACATGGAGGGCTCCGTGAACGGCCACGAGTTCGAGATCGAGG
GCGAGGGCGAGGGCCGCCCCTACGAGGGCACCCAGACCGCCAAGCTGAAGGTGACCAA
GGGTGGCCCCTGCCCTTCGCCTGGGACATCCTGTCCCTCAGTTCATGTACGGCTCCAA
GGCCTACGTGAAGCACCCCGCCGACATCCCCGACTACTTGAAGCTGTCCTTCCCCGAGGG
CTTCAAGTGGGAGCGCGTGATGAACTTCGAGGACGGCGGCGTGGTGACCGTGACCCAGG
ACTCCTCCCTGCAGGACGGCGAGTTCATCTACAAGGTGAAGCTGCGCGGCACCAACTTCC
CCTCCGACGGCCCCGTAATGCAGAAGAAGACCATGGGCTGGGAGGCCTCCTCCGAGCGG
```

FIG. 30 - Cont'd.

```
ATGTACCCCGAGGACGGCGCCCTGAAGGGCGAGATCAAGCAGAGGCTGAAGCTGAAGGA
CGGCGGCCACTACGACGCTGAGGTCAAGACCACCTACAAGGCCAAGAAGCCCGTGCAGC
TGCCCGGCGCCTACAACGTCAACATCAAGTTGGACATCACCTCCCACAACGAGGACTACA
CCATCGTGGAACAGTACGAACGCGCCGAGGGCCGCCACTCCACCGGCGGCATGGACGAG
CTGTACAAGCAAGCTTACGTAGAACAAAAACTCATCTCAGAAGAGGATCTGAATAGCGCCG
TCGACCATCATCATCATCATCATTGAGTTTAAACGGTCTCCAGCTTGGCTGTTTTGGCGGAT
GAGAGAAGATTTTCAGCCTGATACAGATTAAATCAGAACGCAGAAGCGGTCTGATAAAACA
GAATTTGCCTGGCGGCAGTAGCGCGGTGGTCCCACCTGACCCCATGCCGAACTCAGAAGT
GAAACGCCGTAGCGCCGATGGTAGTGTGGGGTCTCCCCATGCGAGAGTAGGGAACTGCC
AGGCATCAAATAAAACGAAAGGCTCAGTCGAAAGACTGGGCCTTTCGTTTTATCTGTTGTTT
GTCGGTGAACGCTCTCCTGAGTAGGACAAATCCGCCGGGAGCGGATTTGAACGTTGCGAA
GCAACGGCCCGGAGGGTGGCGGGCAGGACGCCCGCCATAAACTGCCAGGCATCAAATTA
AGCAGAAGGCCATCCTGACGGATGGCCTTTTTGCGTTTCTACAAACTCTTTTTGTTTATTTT
TCTAAATACATTCAAATATGTATCCGCTCATGAGACAATAACCCTGATAAATGCTTCAATAAT
ATTGAAAAAGGAAGAGTATGAGTATTCAACATTTCCGTGTCGCCCTTATTCCCTTTTTTGCG
GCATTTTGCCTTCCTGTTTTTGCTCACCCAGAAACGCTGGTGAAAGTAAAAGATGCTGAAG
ATCAGTTGGGTGCACGAGTGGGTTACATCGAACTGGATCTCAACAGCGGTAAGATCCTTGA
GAGTTTTCGCCCCGAAGAACGTTTTCCAATGATGAGCACTTTTAAAGTTCTGCTATGTGGC
GCGGTATTATCCCGTGTTGACGCCGGGCAAGAGCAACTCGGTCGCCGCATACACTATTCT
CAGAATGACTTGGTTGAGTACTCACCAGTCACAGAAAAGCATCTTACGGATGGCATGACAG
TAAGAGAATTATGCAGTGCTGCCATAACCATGAGTGATAACACTGCGGCCAACTTACTTCT
GACAACGATCGGAGGACCGAAGGAGCTAACCGCTTTTTTGCACAACATGGGGGATCATGT
AACTCGCCTTGATCGTTGGGAACCGGAGCTGAATGAAGCCATACCAAACGACGAGCGTGA
CACCACGATGCCTGTAGCAATGGCAACAACGTTGCGCAAACTATTAACTGGCGAACTACTT
ACTCTAGCTTCCCGGCAACAATTAATAGACTGGATGGAGGCGGATAAAGTTGCAGGACCA
CTTCTGCGCTCGGCCCTTCCGGCTGGCTGGTTTATTGCTGATAAATCTGGAGCCGGTGAG
CGTGGGTCTCGCGGTATCATTGCAGCACTGGGGCCAGATGGTAAGCCCTCCCGTATCGTA
GTTATCTACACGACGGGGAGTCAGGCAACTATGGATGAACGAAATAGACAGATCGCTGAG
ATAGGTGCCTCACTGATTAAGCATTGGTAACTGTCAGACCAAGTTTACTCATATATACTTTA
GATTGATTTAAAACTTCATTTTTAATTTAAAAGGATCTAGGTGAAGATCCTTTTTGATAATCT
CATGACCAAAATCCCTTAACGTGAGTTTTCGTTCCACTGAGCGTCAGACCCCGTAGAAAAG
ATCAAAGGATCTTCTTGAGATCCTTTTTTTCTGCGCGTAATCTGCTGCTTGCAAACAAAAAA
ACCACCGCTACCAGCGGTGGTTTGTTTGCCGGATCAAGAGCTACCAACTCTTTTTCCGAAG
GTAACTGGCTTCAGCAGAGCGCAGATACCAAATACTGTCCTTCTAGTGTAGCCGTAGTTAG
GCCACCACTTCAAGAACTCTGTAGCACCGCCTACATACCTCGCTCTGCTAATCCTGTTACC
AGTGGCTGCTGCCAGTGGCGATAAGTCGTGTCTTACCGGGTTGGACTCAAGACGATAGTT
ACCGGATAAGGCGCAGCGGTCGGGCTGAACGGGGGGTTCGTGCACACAGCCCAGCTTGG
AGCGAACGACCTACACCGAACTGAGATACCTACAGCGTGAGCTATGAGAAAGCGCCACGC
TTCCCGAAGGGAGAAAGGCGGACAGGTATCCGGTAAGCGGCAGGGTCGGAACAGGAGAG
CGCACGAGGGAGCTTCCAGGGGGAAACGCCTGGTATCTTTATAGTCCTGTCGGGTTTCGC
CACCTCTGACTTGAGCGTCGATTTTTGTGATGCTCGTCAGGGGGCGGAGCCTATGGAAA
AACGCCAGCAACGCGGCCTTTTTACGGTTCCTGGCCTTTTGCTGGCCTTTTGCTCACATGT
```

FIG. 30 - Cont'd.

TCTTTCCTGCGTTATCCCCTGATTCTGTGGATAACCGTATTACCGCCTTTGAGTGAGCTGAT
ACCGCTCGCCGCAGCCGAACGACCGAGCGCAGCGAGTCAGTGAGCGAGGAAGCGGAAG
AGCGCCTGATGCGGTATTTTCTCCTTACGCATCTGTGCGGTATTTCACACCGCATATGGTG
CACTCTCAGTACAATCTGCTCTGATGCCGCATAGTTAAGCCAGTATACACTCCGCTATCGC
TACGTGACTGGGTCATGGCTGCGCCCCGACACCCGCCAACACCCGCTGACGCGCCCTGA
CGGGCTTGTCTGCTCCCGGCATCCGCTTACAGACAAGCTGTGACCGTCTCCGGGAGCTGC
ATGTGTCAGAGGTTTTCACCGTCATCACCGAAACGCGCGAGGCAGCAGATCAATTCGCGC
GCGAAGGCGAAGCGGCATGCATTTACGTTGACACCATCGAATGGTGCAAAACCTTTCGCG
GTATGGCATGATAGCGCCCGGAAGAGAGTCAATTCAGGGTGGTGAATGTGAAACCAGTAA
CGTTATACGATGTCGCAGAGTATGCCGGTGTCTCTTATCAGACCGTTTCCCGCGTGGTGAA
CCAGGCCAGCCACGTTTCTGCGAAAACGCGGGAAAAAGTGGAAGCGGCGATGGCGGAGC
TGAATTACATTCCCAACCGCGTGGCACAACAACTGGCGGGCAAACAGTCGTTGCTGATTG
GCGTTGCCACCTCCAGTCTGGCCCTGCACGCGCCGTCGCAAATTGTCGCGGCGATTAAAT
CTCGCGCCGATCAACTGGGTGCCAGCGTGGTGGTGTCGATGGTAGAACGAAGCGGCGTC
GAAGCCTGTAAAGCGGCGGTGCACAATCTTCTCGCGCAACGCGTCAGTGGGCTGATCATT
AACTATCCGCTGGATGACCAGGATGCCATTGCTGTGGAAGCTGCCTGCACTAATGTTCCG
GCGTTATTTCTTGATGTCTCTGACCAGACACCCATCAACAGTATTATTTTCTCCCATGAAGA
CGGTACGCGACTGGGCGTGGAGCATCTGGTCGCATTGGGTCACCAGCAAATCGCGCTGTT
AGCGGGCCCATTAAGTTCTGTCTCGGCGCGTCTGCGTCTGGCTGGCTGGCATAAATATCT
CACTCGCAATCAAATTCAGCCGATAGCGGAACGGGAAGGCGACTGGAGTGCCATGTCCGG
TTTTCAACAAACCATGCAAATGCTGAATGAGGGCATCGTTCCCACTGCGATGCTGGTTGCC
AACGATCAGATGGCGCTGGGCGCAATGCGCGCCATTACCGAGTCCGGGCTGCGCGTTGG
TGCGGATATCTCGGTAGTGGGATACGACGATACCGAAGACAGCTCATGTTATATCCCGCC
GTCAACCACCATCAAACAGGATTTTCGCCTGCTGGGGCAAACCAGCGTGGACCGCTTGCT
GCAACTCTCTCAGGGCCAGGCGGTGAAGGGCAATCAGCTGTTGCCCGTCTCACTGGTGAA
AAGAAAAACCACCCTGGCGCCCAATACGCAAACCGCCTCTCCCCGCGCGTTGGCCGATTC
ATTAATGCAGCTGGCACGACAGGTTTCCCGACTGGAAAGCGGGCAGTGAGCGCAACGCAA
TTAATGTGAGTTAGCGCGAATTGATCTG

FIG. 31 - *Sequence of a plasmid encoding AcGFP-GBPcys-mCherry*

```
GTTTGACAGCTTATCATCGACTGCACGGTGCACCAATGCTTCTGGCGTCAGGCAGCCATC
GGAAGCTGTGGTATGGCTGTGCAGGTCGTAAATCACTGCATAATTCGTGTCGCTCAAGGC
GCACTCCCGTTCTGGATAATGTTTTTTGCGCCGACATCATAACGGTTCTGGCAAATATTCTG
AAATGAGCTGTTGACAATTAATCATCCGGCTCGTATAATGTGTGGAATTGTGAGCGGATAA
CAATTTCACACAGGAAACAGCGCCGCTGAGAAAAAGCGAAGCGGCACTGCTCTTTAACAAT
TTATCAGACAATCTGTGTGGGCACTCGACCGGAATTATCGATTAACTTTATTATTAAAAATTA
AAGAGGTATATATTAATGTATCGATTAAATAAGGAGGAATAAACCATGGTGAGCAAGGGCG
CCGAGCTGTTCACCGGCATCGTGCCCATCCTGATCGAGCTGAATGGCGATGTGAATGGCC
ACAAGTTCAGCGTGAGCGGCGAGGGCGAGGGCGATGCCACCTACGGCAAGCTGACCCTG
AAGTTCATCTGCACCACCGGCAAGCTGCCTGTGCCCTGGCCCACCCTGGTGACCACCCTG
AGCTACGGCGTGCAGTGCTTCTCACGCTACCCCGATCACATGAAGCAGCACGACTTCTTC
AAGAGCGCCATGCCTGAGGGCTACATCCAGGAGCGCACCATCTTCTTCGAGGATGACGGC
AACTACAAGTCGCGCGCCGAGGTGAAGTTCGAGGGCGATACCCTGGTGAATCGCATCGAG
CTGACCGGCACCGATTTCAAGGAGGATGGCAACATCCTGGGCAATAAGATGGAGTACAAC
TACAACGCCCACAATGTGTACATCATGACCGACAAGGCCAAGAATGGCATCAAGGTGAACT
TCAAGATCCGCCACAACATCGAGGATGGCAGCGTGCAGCTGGCCGACCACTACCAGCAGA
ATACCCCCATCGGCGATGGCCCTGTGCTGCTGCCCGATAACCACTACCTGTCCACCCAGA
GCGCCCTGTCCAAGGACCCCAACGAGAAGCGCGATCACATGATCTACTTCGGCTTCGTGA
CCGCCGCCGCCATCACCCACGGCATGGATGAGCTGTACAAGTCCGGAGCTGATACTCGCA
TTGGTGTAACAATCTATAAGTACGACGATAACTGTATGTCTGTAGTGCGCAAGGCTATTGA
GCAAGATGCGAAAGCCGCGCCAGATGTTCAGCTGCTGATGAATGATTCTCAGAATGACCA
GTCCAAGCAGAACGATCAGATCGACGTATTGCTGGCGAAAGGGGTGAAGGCACTGGCAAT
CAACCTGGTTGACCCGGCAGCTGCGGGTACGGTGATTGAGAAAGCGCGTGGGCAAAACG
TGCCGGTGGTTTTCTTCAACAAAGAACCGTCTCGTAAGGCGCTGGATAGCTACGACAAAGC
CTACTACGTTGGCACTGACTCCAAAGAGTCCGGCATTATTCAAGGCGATTTGATTGCTAAA
CACTGGGCGGCGAATCAGGGTTGGGATCTGAACAAAGACGGTCAGATTCAGTTCGTACTG
CTGAAAGGTGAACCGGGCCATCCGGATGCAGAAGCACGTACCACTTACGTGATTAAAGAA
TTGAACGATAAAGGCATCAAAACTGAACAGTTACAGTTAGATACCGCAATGTGGGACACCG
CTCAGGCGAAAGATAAGATGGACGCCTGGCTGTCTGGCCCGAACGCCAACAAAATCGAAG
TGGTTATCGCCAACAACGATGCGATGGCAATGGGCGCGGTTGAAGCGCTGAAAGCACACA
ACAAGTCCAGCATTCCGGTGTTTGGCGTCGATGCGCTGCCAGAAGCGCTGGCGCTGGTGA
AATCCGGTGCACTGGCGGGCACCGTACTGAACGATGCTAACAACCAGGCGAAAGCGACCT
TTGATCTGGCGAAAAACCTGGCCGATGGTAAAGGTGCGGCTGATGGCACCAACTGGAAAA
TCGACAACAAAGTGGTCCGCGTACCTTATGTTGGCGTAGATAAAGACAACCTGGCTGAATT
CAGCAAGAAAATGATGGTGAGCAAGGGCGAGGAGGATAACATGGCCATCATCAAGGAGTT
CATGCGCTTCAAGGTGCACATGGAGGGCTCCGTGAACGGCCACGAGTTCGAGATCGAGG
GCGAGGGCGAGGGCCGCCCCTACGAGGGCACCCAGACCGCCAAGCTGAAGGTGACCAA
GGGTGGCCCCCTGCCCTTCGCCTGGGACATCCTGTCCCCTCAGTTCATGTACGGCTCCAA
GGCCTACGTGAAGCACCCCGCCGACATCCCCGACTACTTGAAGCTGTCCTTCCCCGAGGG
CTTCAAGTGGGAGCGCGTGATGAACTTCGAGGACGGCGGCGTGGTGACCGTGACCCAGG
ACTCCTCCCTGCAGGACGGCGAGTTCATCTACAAGGTGAAGCTGCGCGGCACCAACTTCC
CCTCCGACGGCCCCGTAATGCAGAAGAAGACCATGGGCTGGGAGGCCTCCTCCGAGCGG
```

FIG. 31 - Cont'd.

ATGTACCCCGAGGACGGCGCCCTGAAGGGCGAGATCAAGCAGAGGCTGAAGCTGAAGGA
CGGCGGCCACTACGACGCTGAGGTCAAGACCACCTACAAGGCCAAGAAGCCCGTGCAGC
TGCCCGGCGCCTACAACGTCAACATCAAGTTGGACATCACCTCCCACAACGAGGACTACA
CCATCGTGGAACAGTACGAACGCGCCGAGGGCCGCCACTCCACCGGCGGCATGGACGAG
CTGTACAAGCAAGCTTACGTAGAACAAAAACTCATCTCAGAAGAGGATCTGAATAGCGCCG
TCGACCATCATCATCATCATCATTGAGTTTAAACGGTCTCCAGCTTGGCTGTTTTGGCGGAT
GAGAGAAGATTTTCAGCCTGATACAGATTAAATCAGAACGCAGAAGCGGTCTGATAAAACA
GAATTTGCCTGGCGGCAGTAGCGCGGTGGTCCCACCTGACCCCATGCCGAACTCAGAAGT
GAAACGCCGTAGCGCCGATGGTAGTGTGGGGTCTCCCCATGCGAGAGTAGGGAACTGCC
AGGCATCAAATAAAACGAAAGGCTCAGTCGAAAGACTGGGCCTTTCGTTTTATCTGTTGTTT
GTCGGTGAACGCTCTCCTGAGTAGGACAAATCCGCCGGGAGCGGATTTGAACGTTGCGAA
GCAACGGCCCGGAGGGTGGCGGGCAGGACGCCCGCCATAAACTGCCAGGCATCAAATTA
AGCAGAAGGCCATCCTGACGGATGGCCTTTTTGCGTTTCTACAAACTCTTTTTGTTTATTTT
TCTAAATACATTCAAATATGTATCCGCTCATGAGACAATAACCCTGATAAATGCTTCAATAAT
ATTGAAAAAGGAAGAGTATGAGTATTCAACATTTCCGTGTCGCCCTTATTCCCTTTTTTGCG
GCATTTTGCCTTCCTGTTTTTGCTCACCCAGAAACGCTGGTGAAAGTAAAAGATGCTGAAG
ATCAGTTGGGTGCACGAGTGGGTTACATCGAACTGGATCTCAACAGCGGTAAGATCCTTGA
GAGTTTTCGCCCCGAAGAACGTTTTCCAATGATGAGCACTTTTAAAGTTCTGCTATGTGGC
GCGGTATTATCCCGTGTTGACGCCGGGCAAGAGCAACTCGGTCGCCGCATACACTATTCT
CAGAATGACTTGGTTGAGTACTCACCAGTCACAGAAAAGCATCTTACGGATGGCATGACAG
TAAGAGAATTATGCAGTGCTGCCATAACCATGAGTGATAACACTGCGGCCAACTTACTTCT
GACAACGATCGGAGGACCGAAGGAGCTAACCGCTTTTTTGCACAACATGGGGGATCATGT
AACTCGCCTTGATCGTTGGGAACCGGAGCTGAATGAAGCCATACCAAACGACGAGCGTGA
CACCACGATGCCTGTAGCAATGGCAACAACGTTGCGCAAACTATTAACTGGCGAACTACTT
ACTCTAGCTTCCCGGCAACAATTAATAGACTGGATGGAGGCGGATAAAGTTGCAGGACCA
CTTCTGCGCTCGGCCCTTCCGGCTGGCTGGTTTATTGCTGATAAATCTGGAGCCGGTGAG
CGTGGGTCTCGCGGTATCATTGCAGCACTGGGGCCAGATGGTAAGCCCTCCCGTATCGTA
GTTATCTACACGACGGGGAGTCAGGCAACTATGGATGAACGAAATAGACAGATCGCTGAG
ATAGGTGCCTCACTGATTAAGCATTGGTAACTGTCAGACCAAGTTTACTCATATATACTTTA
GATTGATTTAAAACTTCATTTTTAATTTAAAAGGATCTAGGTGAAGATCCTTTTTGATAATCT
CATGACCAAAATCCCTTAACGTGAGTTTTCGTTCCACTGAGCGTCAGACCCCGTAGAAAAG
ATCAAAGGATCTTCTTGAGATCCTTTTTTTCTGCGCGTAATCTGCTGCTTGCAAACAAAAAA
ACCACCGCTACCAGCGGTGGTTTGTTTGCCGGATCAAGAGCTACCAACTCTTTTTCCGAAG
GTAACTGGCTTCAGCAGAGCGCAGATACCAAATACTGTCCTTCTAGTGTAGCCGTAGTTAG
GCCACCACTTCAAGAACTCTGTAGCACCGCCTACATACCTCGCTCTGCTAATCCTGTTACC
AGTGGCTGCTGCCAGTGGCGATAAGTCGTGTCTTACCGGGTTGGACTCAAGACGATAGTT
ACCGGATAAGGCGCAGCGGTCGGGCTGAACGGGGGGTTCGTGCACACAGCCCAGCTTGG
AGCGAACGACCTACACCGAACTGAGATACCTACAGCGTGAGCTATGAGAAAGCGCCACGC
TTCCCGAAGGGAGAAAGGCGGACAGGTATCCGGTAAGCGGCAGGGTCGGAACAGGAGAG
CGCACGAGGGAGCTTCCAGGGGGAAACGCCTGGTATCTTTATAGTCCTGTCGGGTTTCGC
CACCTCTGACTTGAGCGTCGATTTTTGTGATGCTCGTCAGGGGGGCGGAGCCTATGGAAA
AACGCCAGCAACGCGGCCTTTTTACGGTTCCTGGCCTTTTGCTGGCCTTTTGCTCACATGT

FIG. 31 - Cont'd.

```
TCTTTCCTGCGTTATCCCCTGATTCTGTGGATAACCGTATTACCGCCTTTGAGTGAGCTGAT
ACCGCTCGCCGCAGCCGAACGACCGAGCGCAGCGAGTCAGTGAGCGAGGAAGCGGAAG
AGCGCCTGATGCGGTATTTTCTCCTTACGCATCTGTGCGGTATTTCACACCGCATATGGTG
CACTCTCAGTACAATCTGCTCTGATGCCGCATAGTTAAGCCAGTATACACTCCGCTATCGC
TACGTGACTGGGTCATGGCTGCGCCCCGACACCCGCCAACACCCGCTGACGCGCCCTGA
CGGGCTTGTCTGCTCCCGGCATCCGCTTACAGACAAGCTGTGACCGTCTCCGGGAGCTGC
ATGTGTCAGAGGTTTTCACCGTCATCACCGAAACGCGCGAGGCAGCAGATCAATTCGCGC
GCGAAGGCGAAGCGGCATGCATTTACGTTGACACCATCGAATGGTGCAAAACCTTTCGCG
GTATGGCATGATAGCGCCCGGAAGAGAGTCAATTCAGGGTGGTGAATGTGAAACCAGTAA
CGTTATACGATGTCGCAGAGTATGCCGGTGTCTCTTATCAGACCGTTTCCCGCGTGGTGAA
CCAGGCCAGCCACGTTTCTGCGAAAACGCGGGAAAAAGTGGAAGCGGCGATGGCGGAGC
TGAATTACATTCCCAACCGCGTGGCACAACAACTGGCGGGCAAACAGTCGTTGCTGATTG
GCGTTGCCACCTCCAGTCTGGCCCTGCACGCGCCGTCGCAAATTGTCGCGGCGATTAAAT
CTCGCGCCGATCAACTGGGTGCCAGCGTGGTGGTGTCGATGGTAGAACGAAGCGGCGTC
GAAGCCTGTAAAGCGGCGGTGCACAATCTTCTCGCGCAACGCGTCAGTGGGCTGATCATT
AACTATCCGCTGGATGACCAGGATGCCATTGCTGTGGAAGCTGCCTGCACTAATGTTCCG
GCGTTATTTCTTGATGTCTCTGACCAGACACCCATCAACAGTATTATTTTCTCCCATGAAGA
CGGTACGCGACTGGGCGTGGAGCATCTGGTCGCATTGGGTCACCAGCAAATCGCGCTGTT
AGCGGGCCCATTAAGTTCTGTCTCGGCGCGTCTGCGTCTGGCTGGCTGGCATAAATATCT
CACTCGCAATCAAATTCAGCCGATAGCGGAACGGGAAGGCGACTGGAGTGCCATGTCCGG
TTTTCAACAAACCATGCAAATGCTGAATGAGGGCATCGTTCCCACTGCGATGCTGGTTGCC
AACGATCAGATGGCGCTGGGCGCAATGCGCGCCATTACCGAGTCCGGGCTGCGCGTTGG
TGCGGATATCTCGGTAGTGGGATACGACGATACCGAAGACAGCTCATGTTATATCCCGCC
GTCAACCACCATCAAACAGGATTTTCGCCTGCTGGGGCAAACCAGCGTGGACCGCTTGCT
GCAACTCTCTCAGGGCCAGGCGGTGAAGGGCAATCAGCTGTTGCCCGTCTCACTGGTGAA
AAGAAAAACCACCCTGGCGCCCAATACGCAAACCGCCTCTCCCGCGCGTTGGCCGATTC
ATTAATGCAGCTGGCACGACAGGTTTCCCGACTGGAAAGCGGGCAGTGAGCGCAACGCAA
TTAATGTGAGTTAGCGCGAATTGATCTG
```

FIG. 32 - Sequence of a plasmid encoding AcGFP-GBPthr-mCherry

```
GTTTGACAGCTTATCATCGACTGCACGGTGCACCAATGCTTCTGGCGTCAGGCAGCCATC
GGAAGCTGTGGTATGGCTGTGCAGGTCGTAAATCACTGCATAATTCGTGTCGCTCAAGGC
GCACTCCCGTTCTGGATAATGTTTTTGCGCCGACATCATAACGGTTCTGGCAAATATTCTG
AAATGAGCTGTTGACAATTAATCATCCGGCTCGTATAATGTGTGGAATTGTGAGCGGATAA
CAATTTCACACAGGAAACAGCGCCGCTGAGAAAAAGCGAAGCGGCACTGCTCTTTAACAAT
TTATCAGACAATCTGTGTGGGCACTCGACCGGAATTATCGATTAACTTTATTATTAAAAATTA
AAGAGGTATATATTAATGTATCGATTAAATAAGGAGGAATAAACCATGGTGAGCAAGGGCG
CCGAGCTGTTCACCGGCATCGTGCCCATCCTGATCGAGCTGAATGGCGATGTGAATGGCC
ACAAGTTCAGCGTGAGCGGCGAGGGCGAGGGCGATGCCACCTACGGCAAGCTGACCCTG
AAGTTCATCTGCACCACCGGCAAGCTGCCTGTGCCCTGGCCCACCCTGGTGACCACCCTG
AGCTACGGCGTGCAGTGCTTCTCACGCTACCCCGATCACATGAAGCAGCACGACTTCTTC
AAGAGCGCCATGCCTGAGGGCTACATCCAGGAGCGCACCATCTTCTTCGAGGATGACGGC
AACTACAAGTCGCGCGCCGAGGTGAAGTTCGAGGGCGATACCCTGGTGAATCGCATCGAG
CTGACCGGCACCGATTTCAAGGAGGATGGCAACATCCTGGGCAATAAGATGGAGTACAAC
TACAACGCCCACAATGTGTACATCATGACCGACAAGGCCAAGAATGGCATCAAGGTGAACT
TCAAGATCCGCCACAACATCGAGGATGGCAGCGTGCAGCTGGCCGACCACTACCAGCAGA
ATACCCCCATCGGCGATGGCCCTGTGCTGCTGCCCGATAACCACTACCTGTCCACCCAGA
GCGCCCTGTCCAAGGACCCCAACGAGAAGCGCGATCACATGATCTACTTCGGCTTCGTGA
CCGCCGCCGCCATCACCCACGGCATGGATGAGCTGTACAAGTCCGGAGCTGATACTCGCA
TTGGTGTAACAATCTATAAGTACGACGATAACACTATGTCTGTAGTGCGCAAGGCTATTGA
GCAAGATGCGAAAGCCGCGCCAGATGTTCAGCTGCTGATGAATGATTCTCAGAATGACCA
GTCCAAGCAGAACGATCAGATCGACGTATTGCTGGCGAAAGGGGTGAAGGCACTGGCAAT
CAACCTGGTTGACCCGGCAGCTGCGGGTACGGTGATTGAGAAAGCGCGTGGGCAAAACG
TGCCGGTGGTTTTCTTCAACAAAGAACCGTCTCGTAAGGCGCTGGATAGCTACGACAAAGC
CTACTACGTTGGCACTGACTCCAAAGAGTCCGGCATTATTCAAGGCGATTTGATTGCTAAA
CACTGGGCGGCGAATCAGGGTTGGGATCTGAACAAAGACGGTCAGATTCAGTTCGTACTG
CTGAAAGGTGAACCGGGCCATCCGGATGCAGAAGCACGTACCACTTACGTGATTAAAGAA
TTGAACGATAAAGGCATCAAAACTGAACAGTTACAGTTAGATACCGCAATGTGGGACACCG
CTCAGGCGAAAGATAAGATGGACGCCTGGCTGTCTGGCCCGAACGCCAACAAAATCGAAG
TGGTTATCGCCAACAACGATGCGATGGCAATGGGCGCGGTTGAAGCGCTGAAAGCACACA
ACAAGTCCAGCATTCCGGTGTTTGGCGTCGATGCGCTGCCAGAAGCGCTGGCGCTGGTGA
AATCCGGTGCACTGGCGGGCACCGTACTGAACGATGCTAACAACCAGGCGAAAGCGACCT
TTGATCTGGCGAAAAACCTGGCCGATGGTAAAGGTGCGGCTGATGGCACCAACTGGAAAA
TCGACAACAAAGTGGTCCGCGTACCTTATGTTGGCGTAGATAAAGACAACCTGGCTGAATT
CAGCAAGAAAATGATGGTGAGCAAGGGCGAGGAGGATAACATGGCCATCATCAAGGAGTT
CATGCGCTTCAAGGTGCACATGGAGGGCTCCGTGAACGGCCACGAGTTCGAGATCGAGG
GCGAGGGCGAGGGCCGCCCCTACGAGGGCACCCAGACCGCCAAGCTGAAGGTGACCAA
GGGTGGCCCCCTGCCCTTCGCCTGGGACATCCTGTCCCCTCAGTTCATGTACGGCTCCAA
GGCCTACGTGAAGCACCCCGCCGACATCCCCGACTACTTGAAGCTGTCCTTCCCCGAGGG
CTTCAAGTGGGAGCGCGTGATGAACTTCGAGGACGGCGGCGTGGTGACCGTGACCCAGG
ACTCCTCCTGCAGGACGGCGAGTTCATCTACAAGGTGAAGCTGCGCGGCACCAACTTCC
CCTCCGACGGCCCCGTAATGCAGAAGAAGACCATGGGCTGGGAGGCCTCCTCCGAGCGG
```

FIG. 32 - Cont'd.

```
ATGTACCCCGAGGACGGCGCCCTGAAGGGCGAGATCAAGCAGAGGCTGAAGCTGAAGGA
CGGCGGCCACTACGACGCTGAGGTCAAGACCACCTACAAGGCCAAGAAGCCCGTGCAGC
TGCCCGGCGCCTACAACGTCAACATCAAGTTGGACATCACCTCCCACAACGAGGACTACA
CCATCGTGGAACAGTACGAACGCGCCGAGGGCCGCCACTCCACCGGCGGCATGGACGAG
CTGTACAAGCAAGCTTACGTAGAACAAAACTCATCTCAGAAGAGGATCTGAATAGCGCCG
TCGACCATCATCATCATCATCATTGAGTTTAAACGGTCTCCAGCTTGGCTGTTTTGGCGGAT
GAGAGAAGATTTTCAGCCTGATACAGATTAAATCAGAACGCAGAAGCGGTCTGATAAAACA
GAATTTGCCTGGCGGCAGTAGCGCGGTGGTCCCACCTGACCCCATGCCGAACTCAGAAGT
GAAACGCCGTAGCGCCGATGGTAGTGTGGGGTCTCCCCATGCGAGAGTAGGGAACTGCC
AGGCATCAAATAAAACGAAAGGCTCAGTCGAAAGACTGGGCCTTTCGTTTTATCTGTTGTTT
GTCGGTGAACGCTCTCCTGAGTAGGACAAATCCGCCGGGAGCGGATTTGAACGTTGCGAA
GCAACGGCCCGGAGGGTGGCGGGCAGGACGCCCGCCATAAACTGCCAGGCATCAAATTA
AGCAGAAGGCCATCCTGACGGATGGCCTTTTGCGTTTCTACAAACTCTTTTTGTTTATTTT
TCTAAATACATTCAAATATGTATCCGCTCATGAGACAATAACCCTGATAAATGCTTCAATAAT
ATTGAAAAAGGAAGAGTATGAGTATTCAACATTTCCGTGTCGCCCTTATTCCCTTTTTTGCG
GCATTTTGCCTTCCTGTTTTTGCTCACCCAGAAACGCTGGTGAAAGTAAAAGATGCTGAAG
ATCAGTTGGGTGCACGAGTGGGTTACATCGAACTGGATCTCAACAGCGGTAAGATCCTTGA
GAGTTTTCGCCCCGAAGAACGTTTTCCAATGATGAGCACTTTTAAAGTTCTGCTATGTGGC
GCGGTATTATCCCGTGTTGACGCCGGGCAAGAGCAACTCGGTCGCCGCATACACTATTCT
CAGAATGACTTGGTTGAGTACTCACCAGTCACAGAAAAGCATCTTACGGATGGCATGACAG
TAAGAGAATTATGCAGTGCTGCCATAACCATGAGTGATAACACTGCGGCCAACTTACTTCT
GACAACGATCGGAGGACCGAAGGAGCTAACCGCTTTTTTGCACAACATGGGGGATCATGT
AACTCGCCTTGATCGTTGGGAACCGGAGCTGAATGAAGCCATACCAAACGACGAGCGTGA
CACCACGATGCCTGTAGCAATGGCAACAACGTTGCGCAAACTATTAACTGGCGAACTACTT
ACTCTAGCTTCCCGGCAACAATTAATAGACTGGATGGAGGCGGATAAAGTTGCAGGACCA
CTTCTGCGCTCGGCCCTTCCGGCTGGCTGGTTTATTGCTGATAAATCTGGAGCCGGTGAG
CGTGGGTCTCGCGGTATCATTGCAGCACTGGGGCCAGATGGTAAGCCCTCCCGTATCGTA
GTTATCTACACGACGGGGAGTCAGGCAACTATGGATGAACGAAATAGACAGATCGCTGAG
ATAGGTGCCTCACTGATTAAGCATTGGTAACTGTCAGACCAAGTTTACTCATATATACTTTA
GATTGATTTAAAACTTCATTTTAATTTAAAAGGATCTAGGTGAAGATCCTTTTTGATAATCT
CATGACCAAAATCCCTTAACGTGAGTTTTCGTTCCACTGAGCGTCAGACCCCGTAGAAAAG
ATCAAAGGATCTTCTTGAGATCCTTTTTTTCTGCGCGTAATCTGCTGCTTGCAAACAAAAAA
ACCACCGCTACCAGCGGTGGTTTGTTTGCCGGATCAAGAGCTACCAACTCTTTTTCCGAAG
GTAACTGGCTTCAGCAGAGCGCAGATACCAAATACTGTCCTTCTAGTGTAGCCGTAGTTAG
GCCACCACTTCAAGAACTCTGTAGCACCGCCTACATACCTCGCTCTGCTAATCCTGTTACC
AGTGGCTGCTGCCAGTGGCGATAAGTCGTGTCTTACCGGGTTGGACTCAAGACGATAGTT
ACCGGATAAGGCGCAGCGGTCGGGCTGAACGGGGGGTTCGTGCACACAGCCCAGCTTGG
AGCGAACGACCTACACCGAACTGAGATACCTACAGCGTGAGCTATGAGAAAGCGCCACGC
TTCCCGAAGGGAGAAAGGCGGACAGGTATCCGGTAAGCGGCAGGGTCGGAACAGGAGAG
CGCACGAGGGAGCTTCCAGGGGGAAACGCCTGGTATCTTTATAGTCCTGTCGGGTTTCGC
CACCTCTGACTTGAGCGTCGATTTTTGTGATGCTCGTCAGGGGGCGGAGCCTATGGAAA
AACGCCAGCAACGCGGCCTTTTTACGGTTCCTGGCCTTTTGCTGGCCTTTTGCTCACATGT
```

FIG. 32 - Cont'd.

```
TCTTTCCTGCGTTATCCCCTGATTCTGTGGATAACCGTATTACCGCCTTTGAGTGAGCTGAT
ACCGCTCGCCGCAGCCGAACGACCGAGCGCAGCGAGTCAGTGAGCGAGGAAGCGGAAG
AGCGCCTGATGCGGTATTTTCTCCTTACGCATCTGTGCGGTATTTCACACCGCATATGGTG
CACTCTCAGTACAATCTGCTCTGATGCCGCATAGTTAAGCCAGTATACACTCCGCTATCGC
TACGTGACTGGGTCATGGCTGCGCCCCGACACCCGCCAACACCCGCTGACGCGCCCTGA
CGGGCTTGTCTGCTCCCGGCATCCGCTTACAGACAAGCTGTGACCGTCTCCGGGAGCTGC
ATGTGTCAGAGGTTTTCACCGTCATCACCGAAACGCGCGAGGCAGCAGATCAATTCGCGC
GCGAAGGCGAAGCGGCATGCATTTACGTTGACACCATCGAATGGTGCAAAACCTTTCGCG
GTATGGCATGATAGCGCCCGGAAGAGAGTCAATTCAGGGTGGTGAATGTGAAACCAGTAA
CGTTATACGATGTCGCAGAGTATGCCGGTGTCTCTTATCAGACCGTTTCCCGCGTGGTGAA
CCAGGCCAGCCACGTTCTGCGAAAACGCGGGAAAAAGTGGAAGCGGCGATGGCGGAGC
TGAATTACATTCCCAACCGCGTGGCACAACAACTGGCGGGCAAACAGTCGTTGCTGATTG
GCGTTGCCACCTCCAGTCTGGCCCTGCACGCGCCGTCGCAAATTGTCGCGGCGATTAAAT
CTCGCGCCGATCAACTGGGTGCCAGCGTGGTGGTGTCGATGGTAGAACGAAGCGGCGTC
GAAGCCTGTAAAGCGGCGGTGCACAATCTTCTCGCGCAACGCGTCAGTGGGCTGATCATT
AACTATCCGCTGGATGACCAGGATGCCATTGCTGTGGAAGCTGCCTGCACTAATGTTCCG
GCGTTATTTCTTGATGTCTCTGACCAGACACCCATCAACAGTATTATTTTCTCCCATGAAGA
CGGTACGCGACTGGGCGTGGAGCATCTGGTCGCATTGGGTCACCAGCAAATCGCGCTGTT
AGCGGGCCCATTAAGTTCTGTCTCGGCGCGTCTGCGTCTGGCTGGCTGGCATAAATATCT
CACTCGCAATCAAATTCAGCCGATAGCGGAACGGGAAGGCGACTGGAGTGCCATGTCCGG
TTTTCAACAAACCATGCAAATGCTGAATGAGGGCATCGTTCCCACTGCGATGCTGGTTGCC
AACGATCAGATGGCGCTGGGCGCAATGCGCGCCATTACCGAGTCCGGGCTGCGCGTTGG
TGCGGATATCTCGGTAGTGGGATACGACGATACCGAAGACAGCTCATGTTATATCCCGCC
GTCAACCACCATCAAACAGGATTTTCGCCTGCTGGGGCAAACCAGCGTGGACCGCTTGCT
GCAACTCTCTCAGGGCCAGGCGGTGAAGGGCAATCAGCTGTTGCCCGTCTCACTGGTGAA
AAGAAAAACCACCCTGGCGCCCAATACGCAAACCGCCTCTCCCCGCGCGTTGGCCGATTC
ATTAATGCAGCTGGCACGACAGGTTTCCCGACTGGAAAGCGGGCAGTGAGCGCAACGCAA
TTAATGTGAGTTAGCGCGAATTGATCTG
```

**FIG. 33 - Sequence of a plasmid encoding *AcGFP-GBPthrDelta12-mCherry***

GTTTGACAGCTTATCATCGACTGCACGGTGCACCAATGCTTCTGGCGTCAGGCAGCCATC
GGAAGCTGTGGTATGGCTGTGCAGGTCGTAAATCACTGCATAATTCGTGTCGCTCAAGGC
GCACTCCCGTTCTGGATAATGTTTTTTGCGCCGACATCATAACGGTTCTGGCAAATATTCTG
AAATGAGCTGTTGACAATTAATCATCCGGCTCGTATAATGTGTGGAATTGTGAGCGGATAA
CAATTTCACACAGGAAACAGCGCCGCTGAGAAAAGCGAAGCGGCACTGCTCTTTAACAAT
TTATCAGACAATCTGTGTGGGCACTCGACCGGAATTATCGATTAACTTTATTATTAAAAATTA
AAGAGGTATATATTAATGTATCGATTAAATAAGGAGGAATAAACCATGGTGAGCAAGGGCG
CCGAGCTGTTCACCGGCATCGTGCCCATCCTGATCGAGCTGAATGGCGATGTGAATGGCC
ACAAGTTCAGCGTGAGCGGCGAGGGCGAGGGCGATGCCACCTACGGCAAGCTGACCCTG
AAGTTCATCTGCACCACCGGCAAGCTGCCTGTGCCCTGGCCCACCCTGGTGACCACCCTG
AGCTACGGCGTGCAGTGCTTCTCACGCTACCCCGATCACATGAAGCAGCACGACTTCTTC
AAGAGCGCCATGCCTGAGGGCTACATCCAGGAGCGCACCATCTTCTTCGAGGATGACGGC
AACTACAAGTCGCGCGCCGAGGTGAAGTTCGAGGGCGATACCCTGGTGAATCGCATCGAG
CTGACCGGCACCGATTTCAAGGAGGATGGCAACATCCTGGGCAATAAGATGGAGTACAAC
TACAACGCCCACAATGTGTACATCATGACCGACAAGGCCAAGAATGGCATCAAGGTGAACT
TCAAGATCCGCCACAACATCGAGGATGGCAGCGTGCAGCTGGCCGACCACTACCAGCAGA
ATACCCCCATCGGCGATGGCCCTGTGCTGCTGCCCGATAACCACTACCTGTCCACCCAGA
GCGCCCTGTCCAAGGACCCCAACGAGAAGCGCGATCACATGATCTACTTCGGCTTCGTGA
CCGCCGCCGCCATCACCCACGGCATGGATGAGCTGTACAAGTCCGGAGACGATAACACTA
TGTCTGTAGTGCGCAAGGCTATTGAGCAAGATGCGAAAGCCGCGCCAGATGTTCAGCTGC
TGATGAATGATTCTCAGAATGACCAGTCCAAGCAGAACGATCAGATCGACGTATTGCTGGC
GAAAGGGGTGAAGGCACTGGCAATCAACCTGGTTGACCCGGCAGCTGCGGGTACGGTGA
TTGAGAAAGCGCGTGGGCAAAACGTGCCGGTGGTTTTCTTCAACAAAGAACCGTCTCGTAA
GGCGCTGGATAGCTACGACAAAGCCTACTACGTTGGCACTGACTCCAAAGAGTCCGGCAT
TATTCAAGGCGATTTGATTGCTAAACACTGGGCGGCGAATCAGGGTTGGGATCTGAACAAA
GACGGTCAGATTCAGTTCGTACTGCTGAAAGGTGAACCGGGCCATCCGGATGCAGAAGCA
CGTACCACTTACGTGATTAAAGAATTGAACGATAAAGGCATCAAAACTGAACAGTTACAGTT
AGATACCGCAATGTGGGACACCGCTCAGGCGAAAGATAAGATGGACGCCTGGCTGTCTGG
CCCGAACGCCAACAAAATCGAAGTGGTTATCGCCAACAACGATGCGATGGCAATGGGCGC
GGTTGAAGCGCTGAAAGCACACAACAAGTCCAGCATTCCGGTGTTTGGCGTCGATGCGCT
GCCAGAAGCGCTGGCGCTGGTGAAATCCGGTGCACTGGCGGGCACCGTACTGAACGATG
CTAACAACCAGGCGAAAGCGACCTTTGATCTGGCGAAAAACCTGGCCGATGGTAAAGGTG
CGGCTGATGGCACCAACTGGAAAATCGACAACAAAGTGGTCCGCGTACCTTATGTTGGCG
TAGATAAAGACAACCTGGCTGAATTCAGCAAGAAATGATGGTGAGCAAGGGCGAGGAGG
ATAACATGGCCATCATCAAGGAGTTCATGCGCTTCAAGGTGCACATGGAGGGCTCCGTGA
ACGGCCACGAGTTCGAGATCGAGGGCGAGGGCGAGGGCCGCCCCTACGAGGGCACCCA
GACCGCCAAGCTGAAGGTGACCAAGGGTGGCCCCCTGCCCTTCGCCTGGGACATCCTGT
CCCCTCAGTTCATGTACGGCTCCAAGGCCTACGTGAAGCACCCCGCCGACATCCCCGACT
ACTTGAAGCTGTCCTTCCCCGAGGGCTTCAAGTGGGAGCGCGTGATGAACTTCGAGGACG
GCGGCGTGGTGACCGTGACCCAGGACTCCTCCCTGCAGGACGGCGAGTTCATCTACAAG
GTGAAGCTGCGCGGCACCAACTTCCCCTCCGACGGCCCCGTAATGCAGAAGAAGACCATG
GGCTGGGAGGCCTCCTCCGAGCGGATGTACCCCGAGGACGGCGCCCTGAAGGGCGAGA

FIG. 33 - Cont'd

```
TCAAGCAGAGGCTGAAGCTGAAGGACGGCGGCCACTACGACGCTGAGGTCAAGACCACC
TACAAGGCCAAGAAGCCCGTGCAGCTGCCCGGCGCCTACAACGTCAACATCAAGTTGGAC
ATCACCTCCCACAACGAGGACTACACCATCGTGGAACAGTACGAACGCGCCGAGGGCCG
CCACTCCACCGGCGGCATGGACGAGCTGTACAAGCAAGCTTACGTAGAACAAAAACTCAT
CTCAGAAGAGGATCTGAATAGCGCCGTCGACCATCATCATCATCATTGAGTTTAAACG
GTCTCCAGCTTGGCTGTTTTGGCGGATGAGAGAAGATTTTCAGCCTGATACAGATTAAATC
AGAACGCAGAAGCGGTCTGATAAAACAGAATTTGCCTGGCGGCAGTAGCGCGGTGGTCCC
ACCTGACCCCATGCCGAACTCAGAAGTGAAACGCCGTAGCGCCGATGGTAGTGTGGGGTC
TCCCCATGCGAGAGTAGGGAACTGCCAGGCATCAAATAAAACGAAAGGCTCAGTCGAAAG
ACTGGGCCTTTCGTTTTATCTGTTGTTTGTCGGTGAACGCTCTCCTGAGTAGGACAAATCC
GCCGGGAGCGGATTTGAACGTTGCGAAGCAACGGCCCGGAGGGTGGCGGGCAGGACGC
CCGCCATAAACTGCCAGGCATCAAATTAAGCAGAAGGCCATCCTGACGGATGGCCTTTTG
CGTTTCTACAAACTCTTTTTGTTTATTTTCTAAATACATTCAAATATGTATCCGCTCATGAGA
CAATAACCCTGATAAATGCTTCAATAATATTGAAAAAGGAAGAGTATGAGTATTCAACATTTC
CGTGTCGCCCTTATTCCCTTTTTTGCGGCATTTTGCCTTCCTGTTTTGCTCACCCAGAAAC
GCTGGTGAAAGTAAAAGATGCTGAAGATCAGTTGGGTGCACGAGTGGGTTACATCGAACT
GGATCTCAACAGCGGTAAGATCCTTGAGAGTTTTCGCCCCGAAGAACGTTTTCCAATGATG
AGCACTTTTAAAGTTCTGCTATGTGGCGCGGTATTATCCCGTGTTGACGCCGGGCAAGAGC
AACTCGGTCGCCGCATACACTATTCTCAGAATGACTTGGTTGAGTACTCACCAGTCACAGA
AAAGCATCTTACGGATGGCATGACAGTAAGAGAATTATGCAGTGCTGCCATAACCATGAGT
GATAACACTGCGGCCAACTTACTTCTGACAACGATCGGAGGACCGAAGGAGCTAACCGCT
TTTTTGCACAACATGGGGGATCATGTAACTCGCCTTGATCGTTGGGAACCGGAGCTGAATG
AAGCCATACCAAACGACGAGCGTGACACCACGATGCCTGTAGCAATGGCAACAACGTTGC
GCAAACTATTAACTGGCGAACTACTTACTCTAGCTTCCCGGCAACAATTAATAGACTGGATG
GAGGCGGATAAAGTTGCAGGACCACTTCTGCGCTCGGCCCTTCCGGCTGGCTGGTTTATT
GCTGATAAATCTGGAGCCGGTGAGCGTGGGTCTCGCGGTATCATTGCAGCACTGGGGCCA
GATGGTAAGCCCTCCCGTATCGTAGTTATCTACACGACGGGGAGTCAGGCAACTATGGAT
GAACGAAATAGACAGATCGCTGAGATAGGTGCCTCACTGATTAAGCATTGGTAACTGTCAG
ACCAAGTTTACTCATATATACTTTAGATTGATTTAAAACTTCATTTTTAATTTAAAAGGATCTA
GGTGAAGATCCTTTTTGATAATCTCATGACCAAAATCCCTTAACGTGAGTTTTCGTTCCACT
GAGCGTCAGACCCCGTAGAAAAGATCAAAGGATCTTCTTGAGATCCTTTTTTTCTGCGCGT
AATCTGCTGCTTGCAAACAAAAAAACCACCGCTACCAGCGGTGGTTTGTTTGCCGGATCAA
GAGCTACCAACTCTTTTTCCGAAGGTAACTGGCTTCAGCAGAGCGCAGATACCAAATACTG
TCCTTCTAGTGTAGCCGTAGTTAGGCCACCACTTCAAGAACTCTGTAGCACCGCCTACATA
CCTCGCTCTGCTAATCCTGTTACCAGTGGCTGCTGCCAGTGGCGATAAGTCGTGTCTTACC
GGGTTGGACTCAAGACGATAGTTACCGGATAAGGCGCAGCGGTCGGGCTGAACGGGGGG
TTCGTGCACACAGCCCAGCTTGGAGCGAACGACCTACACCGAACTGAGATACCTACAGCG
TGAGCTATGAGAAAGCGCCACGCTTCCCGAAGGGAGAAAGGCGGACAGGTATCCGGTAA
GCGGCAGGGTCGGAACAGGAGAGCGCACGAGGGAGCTTCCAGGGGGAAACGCCTGGTA
TCTTTATAGTCCTGTCGGGTTTCGCCACCTCTGACTTGAGCGTCGATTTTTGTGATGCTCGT
CAGGGGGGCGGAGCCTATGGAAAAACGCCAGCAACGCGGCCTTTTACGGTTCCTGGCC
TTTTGCTGGCCTTTTGCTCACATGTTCTTTCCTGCGTTATCCCCTGATTCTGTGGATAACCG
```

FIG. 33 - Cont'd

TATTACCGCCTTTGAGTGAGCTGATACCGCTCGCCGCAGCCGAACGACCGAGCGCAGCGA
GTCAGTGAGCGAGGAAGCGGAAGAGCGCCTGATGCGGTATTTTCTCCTTACGCATCTGTG
CGGTATTTCACACCGCATATGGTGCACTCTCAGTACAATCTGCTCTGATGCCGCATAGTTA
AGCCAGTATACACTCCGCTATCGCTACGTGACTGGGTCATGGCTGCGCCCCGACACCCGC
CAACACCCGCTGACGCGCCCTGACGGGCTTGTCTGCTCCCGGCATCCGCTTACAGACAAG
CTGTGACCGTCTCCGGGAGCTGCATGTGTCAGAGGTTTTCACCGTCATCACCGAAACGCG
CGAGGCAGCAGATCAATTCGCGCGCGAAGGCGAAGCGGCATGCATTTACGTTGACACCAT
CGAATGGTGCAAAACCTTTCGCGGTATGGCATGATAGCGCCCGGAAGAGAGTCAATTCAG
GGTGGTGAATGTGAAACCAGTAACGTTATACGATGTCGCAGAGTATGCCGGTGTCTCTTAT
CAGACCGTTTCCCGCGTGGTGAACCAGGCCAGCCACGTTTCTGCGAAAACGCGGGAAAAA
GTGGAAGCGGCGATGGCGGAGCTGAATTACATTCCCAACCGCGTGGCACAACAACTGGC
GGGCAAACAGTCGTTGCTGATTGGCGTTGCCACCTCCAGTCTGGCCCTGCACGCGCCGTC
GCAAATTGTCGCGGCGATTAAATCTCGCGCCGATCAACTGGGTGCCAGCGTGGTGGTGTC
GATGGTAGAACGAAGCGGCGTCGAAGCCTGTAAAGCGGCGGTGCACAATCTTCTCGCGCA
ACGCGTCAGTGGGCTGATCATTAACTATCCGCTGGATGACCAGGATGCCATTGCTGTGGA
AGCTGCCTGCACTAATGTTCCGGCGTTATTTCTTGATGTCTCTGACCAGACACCCATCAAC
AGTATTATTTTCTCCCATGAAGACGGTACGCGACTGGGCGTGGAGCATCTGGTCGCATTG
GGTCACCAGCAAATCGCGCTGTTAGCGGGCCCATTAAGTTCTGTCTCGGCGCGTCTGCGT
CTGGCTGGCTGGCATAAATATCTCACTCGCAATCAAATTCAGCCGATAGCGGAACGGGAA
GGCGACTGGAGTGCCATGTCCGGTTTTCAACAAACCATGCAAATGCTGAATGAGGGCATC
GTTCCCACTGCGATGCTGGTTGCCAACGATCAGATGGCGCTGGGCGCAATGCGCGCCATT
ACCGAGTCCGGGCTGCGCGTTGGTGCGGATATCTCGGTAGTGGGATACGACGATACCGA
AGACAGCTCATGTTATATCCCGCCGTCAACCACCATCAAACAGGATTTTCGCCTGCTGGGG
CAAACCAGCGTGGACCGCTTGCTGCAACTCTCTCAGGGCCAGGCGGTGAAGGGCAATCA
GCTGTTGCCCGTCTCACTGGTGAAAAGAAAAACCACCCTGGCGCCCAATACGCAAACCGC
CTCTCCCCGCGCGTTGGCCGATTCATTAATGCAGCTGGCACGACAGGTTTCCCGACTGGA
AAGCGGGCAGTGAGCGCAACGCAATTAATGTGAGTTAGCGCGAATTGATCTG

SEQUENCE LISTING

```
<160> NUMBER OF SEQ ID NOS: 9

<210> SEQ ID NO 1
<211> LENGTH: 333
<212> TYPE: PRT
<213> ORGANISM: Escherichia coli

<400> SEQUENCE: 1

Met Asn Lys Lys Val Leu Thr Leu Ser Ala Val Met Ala Ser Met Leu
1               5                   10                  15

Phe Gly Ala Ala Ala His Ala Ala Asp Thr Arg Ile Gly Val Thr Ile
                20                  25                  30

Tyr Lys Tyr Asp Asp Asn Phe Met Ser Val Val Arg Lys Ala Ile Glu
            35                  40                  45

Gln Asp Ala Lys Ala Ala Pro Asp Val Gln Leu Leu Met Asn Asp Ser
        50                  55                  60

Gln Asn Asp Gln Ser Lys Gln Asn Asp Gln Ile Asp Val Leu Leu Ala
65                  70                  75                  80

Lys Gly Val Lys Ala Leu Ala Ile Asn Lys Leu Val Asp Pro Ala Ala
                85                  90                  95

Ala Gly Thr Val Ile Glu Lys Ala Arg Gly Gln Asn Val Pro Val Val
                100                 105                 110

Phe Phe Asn Lys Glu Pro Ser Arg Lys Ala Leu Asp Ser Tyr Asp Lys
            115                 120                 125

Ala Tyr Tyr Val Gly Thr Asp Ser Lys Glu Ser Gly Ile Ile Gln Gly
        130                 135                 140

Asp Leu Ile Ala Lys His Trp Ala Ala Asn Gln Gly Trp Asp Leu Asn
145                 150                 155                 160

Lys Asp Gly Gln Ile Gln Phe Val Leu Leu Lys Gly Glu Pro Gly His
                165                 170                 175

Pro Asp Ala Glu Ala Arg Thr Thr Tyr Val Ile Lys Glu Leu Asn Lys
                180                 185                 190

Asp Gly Ile Lys Thr Glu Gln Leu Gln Leu Asp Thr Ala Met Trp Asp
            195                 200                 205

Thr Ala Gln Ala Lys Asp Lys Met Asp Ala Trp Leu Ser Gly Pro Asn
        210                 215                 220
```

```
Ala Asn Lys Ile Glu Val Val Ile Ala Asn Asn Asp Ala Met Ala Met
225                 230                 235                 240

Gly Ala Val Glu Ala Leu Lys Ala His Asn Lys Ser Ser Ile Pro Val
            245                 250                 255

Phe Gly Val Asp Ala Leu Pro Glu Ala Leu Ala Leu Val Lys Ser Gly
        260                 265                 270

Ala Leu Ala Gly Thr Val Leu Asn Asp Ala Asn Asn Gln Ala Lys Ala
    275                 280                 285

Thr Phe Asp Leu Ala Lys Asn Leu Ala Asp Gly Lys Gly Ala Ala Asp
290                 295                 300

Gly Thr Asn Trp Lys Ile Asp Asn Lys Val Val Arg Val Pro Tyr Val
305                 310                 315                 320

Gly Val Asp Lys Asp Asn Leu Ala Glu Phe Ser Lys Lys
                325                 330

<210> SEQ ID NO 2
<211> LENGTH: 2484
<212> TYPE: DNA
<213> ORGANISM: Artificial Sequence
<220> FEATURE:
<223> OTHER INFORMATION: SYNTHESIZED

<400> SEQUENCE: 2
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta gggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctgggcac     420 aagctggagt acaactacat cagccacaac gtctatatca ccgccgacaa gcagaagaac     480
ggcatcaagg ccaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagggt     720
accggtggta ccggaggcgc cgctgatact cgcattggtg taacaatcta taagtacgac     780
gataacacta tgtctgtagt gcgcaaggct attgagcaag atgcgaaagc cgcgccagat     840
gttcagctgc tgatgaatga ttctcagaat gaccagtcca agcagaacga tcagatcgac     900
gtattgctgg cgaaaggggt gaaggcactg gcaatcaacc tggttgaccc ggcagctgcg     960
ggtacggtga ttgagaaagc gcgtgggcaa acgtgccgg tggttttctt caacaaagaa     1020
ccgtctcgta aggcgctgga tagctacgac aaagcctact acgttggcac tgactccaaa     1080
gagtccggca ttattcaagg cgatttgatt gctaaacact gggcggcgaa tcagggttgg     1140
gatctgaaca agacggtca gattcagttc gtactgctga aggtgaaccc gggccatccg     1200
gatgcagaag cacgtaccac ttacgtgatt aaagaattga cgataaagg catcaaaact     1260 gaacagttac agttagatac cgcaatgtgg gacaccgctc aggcgaaaga taagatggac     1320
gcctggctgt ctggccccaa cgccaacaaa tcgaagtgg ttatcgccaa caacgatgcg     1380
atggcaatgg gcgcggttga agcgctgaaa gcacacaaca gtccagcat ccggtgtttt     1440 ggcgtcgatg cgctgccaga agcgctggcg ctggtgaaat ccggtgcact ggcgggcacc     1500
```

| | |
|---|---:|
| gtactgaacg atgctaacaa ccaggcgaaa gcgacctttg atctggcgaa aaacctggcc | 1560 |
| gatggtaaag gtgcggctga tggcaccaac tggaaaatcg acaacaaagt ggtccgcgta | 1620 |
| ccttatgttg gcgtagataa agacaacctg gctgaattca gcaagaaagg cgccggtacc | 1680 |
| ggtggactag tagtgagcaa gggcgaggag ctgttcaccg gggtggtgcc catcctggtc | 1740 |
| gagctggacg gcgacgtaaa cggccacaag ttcagcgtgt ccggcgaggg cgagggcgat | 1800 |
| gccacctacg gcaagctgac cctgaagttc atctgcacca ccggcaagct gcccgtgccc | 1860 |
| tggcccaccc tcgtgaccac cttcggctac ggcctgatgt gcttcgcccg ctaccccgac | 1920 |
| cacatgaagc agcacgactt cttcaagtcc gccatgcccg aaggctacgt ccaggagcgc | 1980 |
| accatcttct tcaaggacga cggcaactac aagacccgcg ccgaggtgaa gttcgagggc | 2040 |
| gacaccctgg tgaaccgcat cgagctgaag ggcatcgact tcaaggagga cggcaacatc | 2100 |
| ctggggcaca agctggagta caactacaac agccacaacg tctatatcat ggccgacaag | 2160 |
| cagaagaacg gcatcaaggt gaacttcaag atccgccaca acatcgagga cggcagcgtg | 2220 |
| cagctcgccg accactacca gcagaacacc cccatcggcg acggccccgt gctgctgccc | 2280 |
| gacaaccact acctgagcta ccagtccgcc ctgagcaaag accccaacga gaagcgcgat | 2340 |
| cacatggtcc tgctggagtt cgtgaccgcc gccgggatca ctctcggcat ggacgagctg | 2400 |
| tacaagcaag cttacgtaga acaaaaactc atctcagaag aggatctgaa tagcgccgtc | 2460 |
| gaccatcatc atcatcatca ttga | 2484 |

<210> SEQ ID NO 3
<211> LENGTH: 2484
<212> TYPE: DNA
<213> ORGANISM: Artificial Sequence
<220> FEATURE:
<223> OTHER INFORMATION: SYNTHESIZED

<400> SEQUENCE: 3

| | |
|---|---:|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccctgaccta cggcgtgcag tgcttcagcc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacat cagccacaac gtctatatca ccgccgacaa gcagaagaac | 480 |
| ggcatcaagg ccaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actctcggca tggacgagct gtacaagggt | 720 |
| accggtggta ccggaggcgc cgctgatact cgcattggtg taacaatcta taagtacgac | 780 |
| gataactgta tgtctgtagt gcgcaaggct attgagcaag atgcgaaagc gcgccagat | 840 |
| gttcagctgc tgatgaatga ttctcagaat gaccagtcca agcagaacga tcagatcgac | 900 |
| gtattgctgg cgaaaggggt gaaggcactg gcaatcaacc tggttgaccc ggcagctgcg | 960 |
| ggtacgtga ttgagaaagc gcgtgggcaa acgtgccgg tggttttctt caacaaagaa | 1020 |
| ccgtctcgta aggcgctgga tagctacgac aaagcctact acgttggcac tgactccaaa | 1080 |

```
gagtccggca ttattcaagg cgatttgatt gctaaacact gggcggcgaa tcagggttgg   1140
gatctgaaca aagacggtca gattcagttc gtactgctga aggtgaacc gggccatccg    1200 gatgcagaag cacgtaccac ttacgtgatt aaagaattga acgataaagg catcaaaact   1260
gaacagttac agttagatac cgcaatgtgg gacaccgctc aggcgaaaga taagatggac   1320
gcctggctgt ctggcccgaa cgccaacaaa atcgaagtgg ttatcgccaa caacgatgcg   1380
atggcaatgg gcgcggttga agcgctgaaa gcacacaaca agtccagcat tccggtgttt   1440
ggcgtcgatg cgctgccaga agcgctggcg ctggtgaaat ccggtgcact ggcgggcacc   1500
gtactgaacg atgctaacaa ccaggcgaaa gcgacctttg atctggcgaa aaacctggcc   1560
gatggtaaag gtgcggctga tggcaccaac tggaaaatcg acaacaaagt ggtccgcgta   1620
ccttatgttg gcgtagataa agacaacctg gctgaattca gcaagaaagg cgccggtacc   1680
ggtggactag tagtgagcaa gggcgaggag ctgttcaccg gggtggtgcc catcctggtc   1740
gagctggacg gcgacgtaaa cggccacaag ttcagcgtgt ccggcgaggg cgagggcgat   1800
gccacctacg gcaagctgac cctgaagttc atctgcacca ccggcaagct gcccgtgccc   1860
tggcccaccc tcgtgaccac cttcggctac ggcctgatgt gcttcgcccg ctaccccgac   1920
cacatgaagc agcacgactt cttcaagtcc gccatgcccg aaggctacgt ccaggagcgc   1980
accatcttct tcaaggacga cggcaactac aagacccgcg ccgaggtgaa gttcgagggc   2040
gacaccctgg tgaaccgcat cgagctgaag ggcatcgact tcaaggagga cggcaacatc   2100
ctggggcaca gctggagta caactacaac agccacaacg tctatatcat ggccgacaag   2160
cagaagaacg gcatcaaggt gaacttcaag atccgccaca acatcgagga cggcagcgtg   2220
cagctcgccg accactacca gcagaacacc cccatcggcg acggccccgt gctgctgccc   2280
gacaaccact acctgagcta ccagtccgcc ctgagcaaag accccaacga gaagcgcgat   2340
cacatggtcc tgctggagtt cgtgaccgcc gccgggatca ctctcggcat ggacgagctg   2400
tacaagcaag cttacgtaga acaaaaactc atctcagaag aggatctgaa tagcgccgtc   2460
gaccatcatc atcatcatca ttga                                          2484
```

<210> SEQ ID NO 4
<211> LENGTH: 2484
<212> TYPE: DNA
<213> ORGANISM: Artificial Sequence
<220> FEATURE:
<223> OTHER INFORMATION: SYNTHESIZED

<400> SEQUENCE: 4

```
atggtgagca agggcgagga gctgttcacc ggggtggtgc ccatcctggt cgagctggac     60
ggcgacgtaa acgccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgacctg gggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacat cagccacaac gtctatatca ccgccgacaa gcagaagaac    480
ggcatcaagg ccaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
```

```
ctgctggagt tcgtgaccgc cgccgggatc actctcggca tggacgagct gtacaagggt      720
accggtggta ccggaggcgc cgctgatact cgcattggtg taacaatcta taagtacgac      780
gataacttga tgtctgtagt gcgcaaggct attgagcaag atgcgaaagc cgcgccagat      840
gttcagctgc tgatgaatga ttctcagaat gaccagtcca agcagaacga tcagatcgac      900
gtattgctgg cgaaagggt gaaggcactg gcaatcaacc tggttgaccc ggcagctgcg       960
ggtacggtga ttgagaaagc gcgtgggcaa aacgtgccgg tggttttctt caacaaagaa     1020
ccgtctcgta aggcgctgga tagctacgac aaagcctact acgttggcac tgactccaaa     1080
gagtccggca ttattcaagg cgatttgatt gctaaacact gggcggcgaa tcagggttgg     1140
gatctgaaca agacggtca gattcagttc gtactgctga aggtgaacc gggccatccg       1200
gatgcagaag cacgtaccac ttacgtgatt aaagaattga cgataaagg catcaaaact      1260
gaacagttac agttagatac cgcaatgtgg gacaccgctc aggcgaaaga taagatggac     1320
gcctggctgt ctggcccgaa cgccaacaaa atcgaagtgg ttatcgccaa caacgatgcg     1380
atggcaatgg cgcgggttga agcgctgaaa gcacacaaca agtccagcat tccggtgttt     1440
ggcgtcgatg cgctgccaga agcgctggcg ctggtgaaat ccggtgcact ggcgggcacc     1500
gtactgaacg atgctaacaa ccaggcgaaa gcgacctttg atctggcgaa aaacctggcc     1560
gatggtaaag gtgcggctga tggcaccaac tggaaaatcg acaacaaagt ggtccgcgta     1620
ccttatgttg gcgtagataa agacaacctg gctgaattca gcaagaaagg cgccggtacc     1680
ggtggactag tagtgagcaa gggcgaggag ctgttcaccg gggtggtgcc catcctggtc     1740
gagctggacg gcgacgtaaa cggccacaag ttcagcgtgt ccggcgaggg cgagggcgat     1800
gccacctacg gcaagctgac cctgaagttc atctgcacca ccggcaagct gcccgtgccc     1860
tggcccaccc tcgtgaccac cttcggctac ggcctgatgt gcttcgcccg ctaccccgac     1920
cacatgaagc agcacgactt cttcaagtcc gccatgcccg aaggctacgt ccaggagcgc     1980
accatcttct tcaaggacga cggcaactac aagacccgcg ccgaggtgaa gttcgagggc     2040
gacaccctgg tgaaccgcat cgagctgaag ggcatcgact tcaaggagga cggcaacatc     2100
ctggggcaca agctggagta caactacaac agccacaacg tctatatcat ggccgacaag     2160
cagaagaacg gcatcaaggt gaacttcaag atccgccaca acatcgagga cggcagcgtg     2220
cagctcgccg accactacca gcagaacacc cccatcggcg acggccccgt gctgctgccc     2280
gacaaccact acctgagcta ccagtccgcc ctgagcaaag accccaacga gaagcgcgat     2340
cacatggtcc tgctggagtt cgtgaccgcc gccgggatca ctctcggcat ggacgagctg     2400
tacaagcaag cttacgtaga acaaaaactc atctcagaag aggatctgaa tagcgccgtc     2460
gaccatcatc atcatcatca ttga                                           2484
```

<210> SEQ ID NO 5
<211> LENGTH: 2484
<212> TYPE: DNA
<213> ORGANISM: Artificial Sequence
<220> FEATURE:
<223> OTHER INFORMATION: SYNTHESIZED

<400> SEQUENCE: 5

```
atggtgagca agggcgagga gctgttcacc ggggtggtgc ccatcctggt cgagctggac       60
ggcgacgtaa acggccacaa gttcagcgtg tccggcgagg gcgagggcga tgccacctac      120
ggcaagctga ccctgaagtt catctgcacc accggcaagc tgcccgtgcc ctggcccacc      180
ctcgtgacca ccctgacctg gggcgtgcag tgcttcagcc gctaccccga ccacatgaag      240
```

```
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacat cagccacaac gtctatatca ccgccgacaa gcagaagaac    480
ggcatcaagg ccaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagggt    720
accggtggta ccggaggcgc cgctgatact cgcattggtg taacaatcta taagtacgac    780
gataacgtta tgtctgtagt gcgcaaggct attgagcaag atgcgaaagc cgcgccagat    840
gttcagctgc tgatgaatga ttctcagaat gaccagtcca agcagaacga tcagatcgac    900
gtattgctgg cgaaaggggt gaaggcactg gcaatcaacc tggttgaccc ggcagctgcg    960
ggtacggtga ttgagaaagc gcgtgggcaa aacgtgccgg tggttttctt caacaaagaa   1020
ccgtctcgta aggcgctgga tagctacgac aaagcctact acgttggcac tgactccaaa   1080
gagtccggca ttattcaagg cgatttgatt gctaaacact gggcggcgaa tcagggttgg   1140
gatctgaaca aagacggtca gattcagttc gtactgctga aggtgaaccc gggccatccg   1200
gatgcagaag cacgtaccac ttacgtgatt aaagaattga acgataaagg catcaaaact   1260
gaacagttac agttagatac cgcaatgtgg gacaccgctc aggcgaaaga taagatggac   1320
gcctggctgt ctggcccgaa cgccaacaaa atcgaagtgg ttatcgccaa caacgatgcg   1380
atggcaatgg cgcggttga agcgctgaaa gcacacaaca agtccagcat tccggtgttt   1440
ggcgtcgatg cgctgccaga agcgctggcg ctggtgaaat ccggtgcact ggcgggcacc   1500
gtactgaacg atgctaacaa ccaggcgaaa gcgacctttg atctggcgaa aaacctggcc   1560
gatggtaaag gtgcggctga tggcaccaac tggaaaatcg acaacaaagt ggtccgcgta   1620
ccttatgttg gctagataa agacaacctg gctgaattca gcagaaagg cgccggtacc   1680 ggtggactag tagtgagcaa gggcgaggag ctgttcaccg gggtggtgcc catcctggtc   1740
gagctggacg gcgacgtaaa cggccacaag ttcagcgtgt ccggcgaggg cgagggcgat   1800
gccacctacg gcaagctgac cctgaagttc atctgcacca ccggcaagct gcccgtgccc   1860
tggcccaccc tcgtgaccac cttcggctac ggcctgatgt gcttcgcccg ctaccccgac   1920
cacatgaagc agcacgactt cttcaagtcc gccatgcccg aaggctacgt ccaggagcgc   1980
accatcttct tcaaggacga cggcaactac aagacccgcg ccgaggtgaa gttcgagggc   2040
gacaccctgg tgaaccgcat cgagctgaag ggcatcgact tcaaggagga cggcaacatc   2100
ctggggcaca gctggagta caactacaac agccacaacg tctatatcat ggccgacaag   2160
cagaagaacg gcatcaaggt gaacttcaag atccgccaca acatcgagga cggcagcgtg   2220
cagctcgccg accactacca gcagaacacc cccatcggcg acggccccgt gctgctgccc   2280
gacaaccact acctgagcta ccagtccgcc ctgagcaaag accccaacga gaagcgcgat   2340
cacatggtcc tgctggagtt cgtgaccgcc gccgggatca ctctcggcat ggacgagctg   2400
tacaagcaag cttacgtaga acaaaaactc atctcagaag aggatctgaa tagcgccgtc   2460
gaccatcatc atcatcatca ttga                                         2484
```

<210> SEQ ID NO 6
<211> LENGTH: 6721

```
<212> TYPE: DNA
<213> ORGANISM: Artificial Sequence
<220> FEATURE:
<223> OTHER INFORMATION: SYNTHESIZED

<400> SEQUENCE: 6
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatggtgag     420
caagggcgcc gagctgttca ccggcatcgt gcccatcctg atcgagctga atggcgatgt     480
gaatggccac aagttcagcg tgagcggcga gggcgagggc gatgccacct acggcaagct     540
gaccctgaag ttcatctgca ccaccggcaa gctgcctgtg ccctggccca cctggtgac      600 caccctgagc tacggcgtgc agtgcttctc acgctacccc gatcacatga agcagcacga     660
cttcttcaag agcgccatgc ctgagggcta catccaggag cgcaccatct tcttcgagga     720
tgacggcaac tacaagtcgc gcgccgaggt gaagttcgag ggcgataccc tggtgaatcg     780
catcgagctg accggcaccg atttcaagga ggatggcaac atcctgggca ataagatgga     840
gtacaactac aacgcccaca atgtgtacat catgaccgac aaggccaaga atggcatcaa     900
ggtgaacttc aagatccgcc acaacatcga ggatggcagc gtgcagctgg ccgaccacta     960
ccagcagaat acccccatcg gcgatggccc tgtgctgctg cccgataacc actacctgtc    1020
cacccagagc gccctgtcca aggaccccaa cgagaagcgc gatcacatga tctacttcgg    1080
cttcgtgacc gccgccgcca tcacccacgg catggatgag ctgtacaagt ccggagctga    1140
tactcgcatt ggtgtaacaa tctataagta cgacgataac gttatgtctg tagtgcgcaa    1200
ggctattgag caagatgcga aagccgcgcc agatgttcag ctgctgatga atgattctca    1260
gaatgaccag tccaagcaga cgatcagatc gacgtattg ctggcgaaag gggtgaaggc    1320
actggcaatc aacctggttg acccggcagc tgcgggtacg gtgattgaga agcgcgtgg     1380 gcaaaacgtg ccggtggttt tcttcaacaa agaaccgtct cgtaaggcgc tggatagcta    1440
cgacaaagcc tactacgttg gcactgactc caaagagtcc ggcattattc aaggcgattt    1500
gattgctaaa cactgggcgg cgaatcaggg ttgggatctg aacaaagacg gtcagattca    1560
gttcgtactg ctgaaaggtg aaccgggcca tccggatgca gaagcacgta ccacttacgt    1620
gattaaagaa ttgaacgata aaggcatcaa aactgaacag ttacagttag ataccgcaat    1680
gtgggacacc gctcaggcga agataagat ggacgcctgg ctgtctggcc cgaacgccaa    1740
caaaatcgaa gtggttatcg ccaacaacga tgcgatggca atgggcgcgg ttgaagcgct    1800
gaaagcacac aacaagtcca gcattccggt gtttggcgtc gatgcgctgc cagaagcgct    1860
ggcgctggtg aaatccggtg cactggcggg caccgtactg aacgatgcta caaccaggc     1920 gaaagcgacc tttgatctgg cgaaaaacct ggccgatggt aaaggtgcgg ctgatggcac    1980
caactggaaa atcgacaaca aagtggtccg cgtaccttat gttggcgtag ataaagacaa    2040
cctggctgaa ttcagcaaga aaatgatggt gagcaagggc gaggaggata acatggccat    2100
catcaaggag ttcatgcgct tcaaggtgca catggagggc tccgtgaacg gccacgagtt    2160
cgagatcgag ggcgagggcg agggccgccc ctacgagggc acccagaccg ccaagctgaa    2220
```

```
ggtgaccaag ggtggccccc tgcccttcgc ctgggacatc ctgtccctc agttcatgta   2280 cggctccaag gcctacgtga agcaccccgc cgacatcccc gactacttga agctgtcctt   2340
ccccgagggc ttcaagtggg agcgcgtgat gaacttcgag gacggcggcg tggtgaccgt   2400
gacccaggac tcctccctgc aggacggcga gttcatctac aaggtgaagc tgcgcggcac   2460
caacttcccc tccgacggcc ccgtaatgca gaagaagacc atgggctggg aggcctcctc   2520
cgagcggatg taccccgagg acggcgccct gaagggcgag atcaagcaga ggctgaagct   2580
gaaggacggc ggccactacg acgctgaggt caagaccacc tacaaggcca agaagcccgt   2640
gcagctgccc ggcgcctaca acgtcaacat caagttggac atcacctccc acaacgagga   2700
ctacaccatc gtggaacagt acgaacgcgc cgagggccgc cactccaccg gcggcatgga   2760
cgagctgtac aagcaagctt acgtagaaca aaaactcatc tcagaagagg atctgaatag   2820
cgccgtcgac catcatcatc atcatcattg agtttaaacg gtctccagct tggctgtttt   2880
ggcggatgag agaagatttt cagcctgata cagattaaat cagaacgcag aagcggtctg   2940
ataaaacaga atttgcctgg cggcagtagc gcggtggtcc cacctgaccc catgccgaac   3000
tcagaagtga acgccgtag cgccgatggt agtgtggggt ctccccatgc gagagtaggg   3060
aactgccagg catcaaataa aacgaaaggc tcagtcgaaa gactgggcct ttcgttttat   3120
ctgttgtttg tcggtgaacg ctctcctgag taggacaaat ccgccgggag cggatttgaa   3180
cgttgcgaag caacggcccg gagggtggcg ggcaggacgc ccgccataaa ctgccaggca   3240
tcaaattaag cagaaggcca tcctgacgga tggcctttt gcgtttctac aaactctttt   3300
tgtttatttt tctaaataca ttcaaatatg tatccgctca tgagacaata accctgataa   3360
atgcttcaat aatattgaaa aaggaagagt atgagtatt aacatttccg tgtcgccctt   3420
attccctttt ttgcggcatt ttgccttcct gttttgctc acccagaaac gctggtgaaa   3480
gtaaaagatg ctgaagatca gttgggtgca cgagtgggtt acatcgaact ggatctcaac   3540
agcggtaaga tccttgagag ttttcgcccc gaagaacgtt ttccaatgat gagcactttt   3600
aaagttctgc tatgtggcgc ggtattatcc cgtgttgacg ccgggcaaga gcaactcggt   3660
cgccgcatac actattctca gaatgacttg gttgagtact caccagtcac agaaaagcat   3720
cttacggatg gcatgacagt aagagaatta tgcagtgctg ccataaccat gagtgataac   3780
actgcggcca acttacttct gacaacgatc ggaggaccga aggagctaac cgcttttttg   3840
cacaacatgg gggatcatgt aactcgcctt gatcgttggg aaccggagct gaatgaagcc   3900
ataccaaacg acgagcgtga caccacgatg cctgtagcaa tggcaacaac gttgcgcaaa   3960
ctattaactg gcgaactact tactctagct tcccggcaac aattaataga ctggatggag   4020
gcggataaag ttgcaggacc acttctgcgc tcggcccttc cggctggctg gtttattgct   4080
gataaatctg gagccggtga gcgtgggtct cgcggtatca ttgcagcact ggggccagat   4140
ggtaagccct cccgtatcgt agttatctac acgacgggga gtcaggcaac tatggatgaa   4200
cgaaatagac agatcgctga gataggtgcc tcactgatta gcattggta actgtcagac   4260 caagtttact catatatact ttagattgat ttaaaacttc atttttaatt taaaaggatc   4320
taggtgaaga tcctttttga taatctcatg accaaaatcc cttaacgtga gttttcgttc   4380
cactgagcgt cagaccccgt agaaaagatc aaaggatctt cttgagatcc ttttttctg   4440 cgcgtaatct gctgcttgca acaaaaaaa ccaccgctac cagcggtggt ttgtttgccg   4500
gatcaagagc taccaactct ttttccgaag gtaactggct tcagcagagc gcagatacca   4560
aatactgtcc ttctagtgta gccgtagtta ggccaccact tcaagaactc tgtagcaccg   4620
```

```
cctacatacc tcgctctgct aatcctgtta ccagtggctg ctgccagtgg cgataagtcg    4680
tgtcttaccg ggttggactc aagacgatag ttaccggata aggcgcagcg gtcgggctga    4740
acgggggggtt cgtgcacaca gcccagcttg gagcgaacga cctacaccga actgagatac    4800
ctacagcgtg agctatgaga aagcgccacg cttcccgaag ggagaaaggc ggacaggtat    4860
ccggtaagcg gcagggtcgg aacaggagag cgcacgaggg agcttccagg ggaaaacgcc    4920
tggtatcttt atagtcctgt cgggtttcgc cacctctgac ttgagcgtcg attttttgtga   4980
tgctcgtcag gggggcggag cctatggaaa aacgccagca acgcggcctt tttacggttc    5040
ctggcctttt gctggccttt tgctcacatg ttctttcctg cgttatcccc tgattctgtg    5100
gataaccgta ttaccgcctt tgagtgagct gataccgctc gccgcagccg aacgaccgag    5160
cgcagcgagt cagtgagcga ggaagcggaa gagcgcctga tgcggtattt tctccttacg    5220
catctgtgcg gtatttcaca ccgcatatgg tgcactctca gtacaatctg ctctgatgcc    5280
gcatagttaa gccagtatac actccgctat cgctacgtga ctgggtcatg gctgcgcccc    5340
gacacccgcc aacacccgct gacgcgccct gacgggcttg tctgctcccg gcatccgctt    5400
acagacaagc tgtgaccgtc tccgggagct gcatgtgtca gaggttttca ccgtcatcac    5460
cgaaacgcgc gaggcagcag atcaattcgc gcgcgaaggc gaagcggcat gcatttacgt    5520
tgacaccatc gaatggtgca aaacctttcg cggtatggca tgatagcgcc cggaagagag    5580
tcaattcagg gtggtgaatg tgaaaccagt aacgttatac gatgtcgcag agtatgccgg    5640
tgtctcttat cagaccgttt cccgcgtggt gaaccaggcc agccacgttt ctgcgaaaac    5700
gcgggaaaaa gtggaagcgg cgatggcgga gctgaattac attcccaacc gcgtggcaca    5760
acaactggcg ggcaaacagt cgttgctgat tggcgttgcc acctccagtc tggccctgca    5820
cgcgccgtcg caaattgtcg cggcgattaa atctcgcgcc gatcaactgg gtgccagcgt    5880
ggtggtgtcg atggtagaac gaagcggcgt cgaagcctgt aaagcggcgg tgcacaatct    5940
tctcgcgcaa cgcgtcagtg ggctgatcat taactatccg ctggatgacc aggatgccat    6000
tgctgtggaa gctgcctgca ctaatgttcc ggcgttattt cttgatgtct ctgaccagac    6060
acccatcaac agtattattt tctcccatga agacggtacg cgactgggcg tggagcatct    6120
ggtcgcattg ggtcaccagc aaatcgcgct gttagcgggc ccattaagtt ctgtctcggc    6180
gcgtctgcgt ctggctggct ggcataaata tctcactcgc aatcaaattc agccgatagc    6240
ggaacgggaa ggcgactgga gtgccatgtc cggttttcaa caaaccatgc aaatgctgaa    6300
tgagggcatc gttcccactg cgatgctggt tgccaacgat cagatggcgc tgggcgcaat    6360
gcgcgccatt accgagtccg ggctgcgcgt tggtgcggat atctcggtag tgggatacga    6420
cgataccgaa gacagctcat gttatatccc gccgtcaacc accatcaaac aggattttcg    6480
cctgctgggg caaaccagcg tggaccgctt gctgcaactc tctcagggcc aggcggtgaa    6540
gggcaatcag ctgttgcccg tctcactggt gaaaagaaaa accaccctgg cgcccaatac    6600
gcaaaccgcc tctccccgcg cgttggccga ttcattaatg cagctggcac gacaggtttc    6660
ccgactggaa agcgggcagt gagcgcaacg caattaatgt gagttagcgc gaattgatct    6720
g                                                                     6721
```

<210> SEQ ID NO 7
<211> LENGTH: 6721
<212> TYPE: DNA
<213> ORGANISM: Artificial Sequence
<220> FEATURE:
<223> OTHER INFORMATION: SYNTHESIZED

<400> SEQUENCE: 7

```
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatggtgag     420
caagggcgcc gagctgttca ccggcatcgt gcccatcctg atcgagctga atggcgatgt     480
gaatggccac aagttcagcg tgagcggcga gggcgagggc gatgccacct acggcaagct     540
gaccctgaag ttcatctgca ccaccggcaa gctgcctgtg ccctggccca ccctggtgac     600
cacccctgagc tacggcgtgc agtgcttctc acgctacccc gatcacatga agcagcacga     660
cttcttcaag agcgccatgc ctgagggcta catccaggag cgcaccatct tcttcgagga     720
tgacggcaac tacaagtcgc gcgccgaggt gaagttcgag ggcgataccc tggtgaatcg     780
catcgagctg accggcaccg atttcaagga ggatggcaac atcctgggca ataagatgga     840
gtacaactac aacgcccaca atgtgtacat catgaccgac aaggccaaga atggcatcaa     900
ggtgaacttc aagatccgcc acaacatcga ggatggcagc gtgcagctgg ccgaccacta     960
ccagcagaat accccccatcg gcgatggccc tgtgctgctg cccgataacc actacctgtc    1020
cacccagagc gccctgtcca aggaccccaa cgagaagcgc gatcacatga tctacttcgg    1080
cttcgtgacc gccgccgcca tcacccacgg catggatgag ctgtacaagt ccggagctga    1140
tactcgcatt ggtgtaacaa tctataagta cgacgataac tgtatgtctg tagtgcgcaa    1200
ggctattgag caagatgcga aagccgcgcc agatgttcag ctgctgatga atgattctca    1260
gaatgaccag tccaagcaga acgatcagat cgacgtattg ctggcgaaag gggtgaaggc    1320
actggcaatc aacctggttg acccggcagc tgcgggtacg gtgattgaga agcgcgtgg    1380
gcaaaacgtg ccggtggttt tcttcaacaa agaaccgtct cgtaaggcgc tggatagcta    1440
cgacaaagcc tactacgttg gcactgactc caaagagtcc ggcattattc aaggcgattt    1500
gattgctaaa cactgggcgg cgaatcaggg ttgggatctg aacaaagacg gtcagattca    1560
gttcgtactg ctgaaaggtg aaccgggcca tccggatgca gaagcacgta ccacttacgt    1620
gattaaagaa ttgaacgata aaggcatcaa aactgaacag ttacagttag ataccgcaat    1680
gtgggacacc gctcaggcga agataagat ggacgcctgg ctgtctggcc cgaacgccaa    1740
caaaatcgaa gtggttatcg ccaacaacga tgcgatggca atgggcgcgg ttgaagcgct    1800
gaaagcacac aacaagtcca gcattccggt gtttggcgtc gatgcgctgc cagaagcgct    1860
ggcgctggtg aaatccggtg cactggcggg caccgtactg aacgatgcta acaaccaggc    1920
gaaagcgacc tttgatctgg cgaaaaacct ggccgatggt aaaggtgcgg ctgatggcac    1980
caactggaaa atcgacaaca aagtggtccg cgtaccttat gttggcgtag ataaagacaa    2040
cctggctgaa ttcagcaaga aaatgatggt gagcaagggc gaggaggata acatggccat    2100
catcaaggag ttcatgcgct tcaaggtgca catggagggc tccgtgaacg gccacgagtt    2160
cgagatcgag ggcgagggcg agggccgccc ctacgagggc acccagaccg ccaagctgaa    2220
ggtgaccaag ggtggcccc tgcccttcgc ctggacatc ctgtcccctc agttcatgta    2280
cggctccaag gcctacgtga agcaccccgc cgacatcccc gactacttga agctgtcctt    2340
```

```
ccccgagggc ttcaagtggg agcgcgtgat gaacttcgag gacggcggcg tggtgaccgt    2400
gacccaggac tcctccctgc aggacggcga gttcatctac aaggtgaagc tgcgcggcac    2460
caacttcccc tccgacggcc ccgtaatgca agaagaagacc atgggctggg aggcctcctc   2520
cgagcggatg taccccgagg acggcgccct gaagggcgag atcaagcaga ggctgaagct    2580
gaaggacggc ggccactacg acgctgaggt caagaccacc tacaaggcca agaagcccgt    2640
gcagctgccc ggcgcctaca cgtcaacat caagttggac atcacctccc acaacgagga     2700
ctacaccatc gtggaacagt acgaacgcgc cgagggccgc cactccaccg gcggcatgga    2760
cgagctgtac aagcaagctt acgtagaaca aaaactcatc tcagaagagg atctgaatag    2820
cgccgtcgac catcatcatc atcatcattg agtttaaacg gtctccagct tggctgtttt    2880
ggcggatgag agaagatttt cagcctgata cagattaaat cagaacgcag aagcggtctg    2940
ataaaacaga atttgcctgg cggcagtagc gcggtggtcc cacctgaccc catgccgaac    3000
tcagaagtga acgccgtag cgccgatggt agtgtggggt ctccccatgc gagagtaggg     3060
aactgccagg catcaaataa aacgaaaggc tcagtcgaaa gactgggcct ttcgttttat    3120
ctgttgtttg tcggtgaacg ctctcctgag taggacaaat ccgccgggag cggatttgaa    3180
cgttgcgaag caacggcccg gagggtggcg ggcaggacgc ccgccataaa ctgccaggca    3240
tcaaattaag cagaaggcca tcctgacgga tggcctttt gcgtttctac aaactctttt     3300
tgtttatttt tctaaataca ttcaaatatg tatccgctca tgagacaata accctgataa    3360
atgcttcaat aatattgaaa aaggaagagt atgagtattc aacatttccg tgtcgccctt    3420 attcccttt ttgcggcatt ttgccttcct gttttgctc acccagaaac gctggtgaaa      3480
gtaaaagatg ctgaagatca gttgggtgca cgagtgggtt acatcgaact ggatctcaac    3540
agcggtaaga tccttgagag ttttcgcccc gaagaacgtt ttccaatgat gagcactttt    3600
aaagttctgc tatgtggcgc ggtattatcc cgtgttgacg ccgggcaaga gcaactcggt    3660
cgccgcatac actattctca gaatgacttg gttgagtact caccagtcac agaaaagcat    3720
cttacggatg gcatgacagt aagagaatta tgcagtgctg ccataaccat gagtgataac    3780
actgcggcca acttacttct gacaacgatc ggaggaccga aggagctaac cgcttttttg    3840
cacaacatgg gggatcatgt aactcgcctt gatcgttggg aaccggagct gaatgaagcc    3900
ataccaaacg acgagcgtga caccacgatg cctgtagcaa tggcaacaac gttgcgcaaa    3960
ctattaactg gcgaactact tactctagct tcccggcaac aattaataga ctggatggag    4020
gcggataaag ttgcaggacc acttctgcgc tcggcccttc cggctggctg gtttattgct    4080
gataaatctg gagccggtga gcgtgggtct cgcggtatca ttgcagcact ggggccagat    4140
ggtaagccct cccgtatcgt agttatctac acgacgggga gtcaggcaac tatggatgaa    4200
cgaaatagac agatcgctga gataggtgcc tcactgatta gcattggta actgtcagac     4260 caagtttact catatatact ttagattgat ttaaaacttc attttttaatt taaaaggatc   4320 taggtgaaga tccttttga taatctcatg accaaaatcc cttaacgtga gttttcgttc     4380
cactgagcgt cagaccccgt agaaaagatc aaaggatctt cttgagatcc ttttttctg     4440 cgcgtaatct gctgcttgca acaaaaaaa ccaccgctac cagcggtggt ttgtttgccg     4500
gatcaagagc taccaactct ttttccgaag gtaactggct tcagcagagc gcagatacca    4560
aatactgtcc ttctagtgta gccgtagtta ggccaccact tcaagaactc tgtagcaccg    4620
cctacatacc tcgctctgct aatcctgtta ccagtggctg ctgccagtgg cgataagtcg    4680
tgtcttaccg ggttggactc aagacgatag ttaccggata aggcgcagcg gtcgggctga    4740
```

```
acgggggtt cgtgcacaca gcccagcttg gagcgaacga cctacaccga actgagatac    4800
ctacagcgtg agctatgaga aagcgccacg cttcccgaag ggagaaaggc ggacaggtat    4860
ccggtaagcg gcagggtcgg aacaggagag cgcacgaggg agcttccagg gggaaacgcc    4920
tggtatcttt atagtcctgt cgggtttcgc cacctctgac ttgagcgtcg attttttgtga   4980 tgctcgtcag gggggcggag cctatggaaa aacgccagca acgcggcctt tttacggttc    5040
ctggcctttt gctggccttt tgctcacatg ttctttcctg cgttatcccc tgattctgtg    5100
gataaccgta ttaccgcctt tgagtgagct gataccgctc gccgcagccg aacgaccgag    5160
cgcagcgagt cagtgagcga ggaagcggaa gagcgcctga tgcggtattt tctccttacg    5220
catctgtgcg gtatttcaca ccgcatatgg tgcactctca gtacaatctg ctctgatgcc    5280
gcatagttaa gccagtatac actccgctat cgctacgtga ctgggtcatg gctgcgcccc    5340
gacacccgcc aacacccgct gacgcgccct gacgggcttg tctgctcccg gcatccgctt    5400
acagacaagc tgtgaccgtc tccgggagct gcatgtgtca gaggttttca ccgtcatcac    5460
cgaaacgcgc gaggcagcag atcaattcgc gcgcgaaggc gaagcggcat gcatttacgt    5520
tgacaccatc gaatggtgca aaacctttcg cggtatggca tgatagcgcc cggaagagag    5580
tcaattcagg gtggtgaatg tgaaaccagt aacgttatac gatgtcgcag agtatgccgg    5640
tgtctcttat cagaccgttt cccgcgtggt gaaccaggcc agccacgttt ctgcgaaaac    5700
gcgggaaaaa gtggaagcgg cgatggcgga gctgaattac attcccaacc gcgtggcaca    5760
acaactggcg gcaaacagt cgttgctgat tggcgttgcc acctccagtc tggccctgca    5820
cgcgccgtcg caaattgtcg cggcgattaa atctcgcgcc gatcaactgg gtgccagcgt    5880
ggtggtgtcg atggtagaac gaagcggcgt cgaagcctgt aaagcggcgg tgcacaatct    5940
tctcgcgcaa cgcgtcagtg ggctgatcat taactatccg ctggatgacc aggatgccat    6000
tgctgtggaa gctgcctgca ctaatgttcc ggcgttattt cttgatgtct ctgaccagac    6060
acccatcaac agtattattt tctcccatga agacggtacg cgactgggcg tggagcatct    6120
ggtcgcattg ggtcaccagc aaatcgcgct gttagcgggc ccattaagtt ctgtctcggc    6180
gcgtctgcgt ctggctggct ggcataaata tctcactcgc aatcaaattc agccgatagc    6240
ggaacgggaa ggcgactgga gtgccatgtc cggttttcaa caaaccatgc aaatgctgaa    6300
tgagggcatc gttcccactg cgatgctggt tgccaacgat cagatggcgc tgggcgcaat    6360
gcgcgccatt accgagtccg ggctgcgcgt tggtgcggat atctcggtag tgggatacga    6420
cgataccgaa gacagctcat gttatatccc gccgtcaacc accatcaaac aggattttcg    6480
cctgctgggg caaccagcg tggaccgctt gctgcaactc tctcagggcc aggcggtgaa    6540
gggcaatcag ctgttgcccg tctcactggt gaaaagaaaa accaccctgg cgcccaatac    6600
gcaaaccgcc tctccccgcg cgttggccga ttcattaatg cagctggcac gacaggtttc    6660
ccgactggaa agcgggcagt gagcgcaacg caattaatgt gagttagcgc gaattgatct    6720
g                                                                    6721
```

<210> SEQ ID NO 8
<211> LENGTH: 6721
<212> TYPE: DNA
<213> ORGANISM: Artificial Sequence
<220> FEATURE:
<223> OTHER INFORMATION: SYNETHESIZED

<400> SEQUENCE: 8

```
gtttgacagc ttatcatcga ctgcacggtg caccaatgct tctggcgtca ggcagccatc      60
```

```
ggaagctgtg gtatggctgt gcaggtcgta aatcactgca taattcgtgt cgctcaaggc    120
gcactcccgt tctggataat gttttttgcg ccgacatcat aacggttctg gcaaatattc    180
tgaaatgagc tgttgacaat taatcatccg gctcgtataa tgtgtggaat tgtgagcgga    240
taacaatttc acacaggaaa cagcgccgct gagaaaaagc gaagcggcac tgctctttaa    300
caatttatca gacaatctgt gtgggcactc gaccggaatt atcgattaac tttattatta    360
aaaattaaag aggtatatat taatgtatcg attaaataag gaggaataaa ccatggtgag    420
caagggcgcc gagctgttca ccggcatcgt gcccatcctg atcgagctga atggcgatgt    480
gaatggccac aagttcagcg tgagcggcga gggcgagggc gatgccacct acggcaagct    540
gaccctgaag ttcatctgca ccaccggcaa gctgcctgtg ccctggccca ccctggtgac    600
caccctgagc tacggcgtgc agtgcttctc acgctacccc gatcacatga agcagcacga    660
cttcttcaag agcgccatgc ctgagggcta catccaggag cgcaccatct tcttcgagga    720
tgacggcaac tacaagtcgc gcgccgaggt gaagttcgag ggcgataccc tggtgaatcg    780
catcgagctg accggcaccg atttcaagga ggatggcaac atcctgggca taagatgga    840 gtacaactac aacgcccaca atgtgtacat catgaccgac aaggccaaga atggcatcaa    900
ggtgaacttc aagatccgcc acaacatcga ggatggcagc gtgcagctgg ccgaccacta    960
ccagcagaat acccccatcg gcgatggccc tgtgctgctg cccgataacc actacctgtc   1020
cacccagagc gccctgtcca aggaccccaa cgagaagcgc gatcacatga tctacttcgg   1080
cttcgtgacc gccgccgcca tcacccacgg catggatgag ctgtacaagt ccggagctga   1140
tactcgcatt ggtgtaacaa tctataagta cgacgataac actatgtctg tagtgcgcaa   1200
ggctattgag caagatgcga aagccgcgcc agatgttcag ctgctgatga atgattctca   1260
gaatgaccag tccaagcaga acgatcagat cgacgtattg ctggcgaaag gggtgaaggc   1320
actggcaatc aacctggttg acccggcagc tgcgggtacg gtgattgaga agcgcgtgg   1380 gcaaaacgtg ccggtggttt tcttcaacaa agaaccgtct cgtaaggcgc tggatagcta   1440
cgacaaagcc tactacgttg gcactgactc caaagagtcc ggcattattc aaggcgattt   1500
gattgctaaa cactgggcgg cgaatcaggg ttgggatctg aacaaagacg gtcagattca   1560
gttcgtactg ctgaaaggtg aaccgggcca tccggatgca gaagcacgta ccacttacgt   1620
gattaaagaa ttgaacgata aaggcatcaa aactgaacag ttacagttag ataccgcaat   1680
gtgggacacc gctcaggcga agataagat ggacgcctgg ctgtctggcc cgaacgccaa   1740
caaaatcgaa gtggttatcg ccaacaacga tgcgatggca atgggcgcgg ttgaagcgct   1800
gaaagcacac aacaagtcca gcattccggt gtttggcgtc gatgcgctgc agaagcgct    1860 ggcgctggtg aaatccggtg cactggcggg caccgtactg aacgatgcta acaaccaggc   1920
gaaagcgacc tttgatctgg cgaaaaacct ggccgatggt aaaggtgcgg ctgatggcac   1980
caactggaaa atcgacaaca aagtggtccg cgtaccttat gttggcgtag ataaagacaa   2040
cctggctgaa ttcagcaaga aaatgatggt gagcaagggc gaggaggata acatggccat   2100
catcaaggag ttcatgcgct tcaaggtgca catggagggc tccgtgaacg ccacgagtt    2160 cgagatcgag ggcgagggcg agggccgccc ctacgagggc acccagaccg ccaagctgaa   2220
ggtgaccaag ggtggccccc tgcccttcgc ctggacatc ctgtcccctc agttcatgta    2280
cggctccaag gcctacgtga agcaccccgc cgacatcccc gactacttga agctgtcctt   2340
cccccgaggg ttcaagtggg agcgcgtgat gaacttcgag gacggcggcg tggtgaccgt   2400
gacccaggac tcctccctgc aggacggcga gttcatctac aaggtgaagc tgcgcggcac   2460
```

```
caacttcccc tccgacggcc ccgtaatgca gaagaagacc atgggctggg aggcctcctc   2520
cgagcggatg taccccgagg acggcgccct gaagggcgag atcaagcaga ggctgaagct   2580
gaaggacggc ggccactacg acgctgaggt caagaccacc tacaaggcca gaagcccgt    2640 gcagctgccc ggcgcctaca acgtcaacat caagttggac atcacctccc acaacgagga   2700
ctacaccatc gtggaacagt acgaacgcgc cgagggccgc cactccaccg gcggcatgga   2760
cgagctgtac aagcaagctt acgtagaaca aaaactcatc tcagaagagg atctgaatag   2820
cgccgtcgac catcatcatc atcatcattg agtttaaacg gtctccagct tggctgtttt   2880
ggcggatgag agaagatttt cagcctgata cagattaaat cagaacgcag aagcggtctg   2940
ataaaacaga atttgcctgg cggcagtagc gcggtggtcc cacctgaccc catgccgaac   3000
tcagaagtga aacgccgtag cgccgatggt agtgtggggt ctccccatgc gagagtaggg   3060
aactgccagg catcaaataa acgaaaggc tcagtcgaaa gactgggcct ttcgttttat    3120
ctgttgtttg tcggtgaacg ctctcctgag taggacaaat ccgccgggag cggatttgaa   3180
cgttgcgaag caacggcccg gagggtggcg ggcaggacgc ccgccataaa ctgccaggca   3240
tcaaattaag cagaaggcca tcctgacgga tggcctttt gcgtttctac aaactctttt    3300
tgtttatttt tctaaataca ttcaaatatg tatccgctca tgagacaata accctgataa   3360
atgcttcaat aatattgaaa aaggaagagt atgagtattc aacatttccg tgtcgccctt   3420
attccctttt ttgcggcatt ttgccttcct gttttgctc acccagaaac gctggtgaaa    3480
gtaaaagatg ctgaagatca gttgggtgca cgagtgggtt acatcgaact ggatctcaac   3540
agcggtaaga tccttgagag ttttcgcccc gaagaacgtt ttccaatgat gagcactttt   3600
aaagttctgc tatgtggcgc ggtattatcc cgtgttgacg ccgggcaaga gcaactcggt   3660
cgccgcatac actattctca gaatgacttg gttgagtact caccagtcac agaaaagcat   3720
cttacggatg gcatgacagt aagagaatta tgcagtgctg ccataaccat gagtgataac   3780
actgcggcca acttacttct gacaacgatc ggaggaccga aggagctaac cgcttttttg   3840
cacaacatgg ggatcatgt aactcgcctt gatcgttggg aaccggagct gaatgaagcc    3900
ataccaaacg acgagcgtga caccacgatg cctgtagcaa tggcaacaac gttgcgcaaa   3960
ctattaactg gcgaactact tactctagct tcccggcaac aattaataga ctggatggag   4020
gcggataaag ttgcaggacc acttctgcgc tcggcccttc cggctggctg gtttattgct   4080
gataaatctg gagccggtga gcgtgggtct cgcggtatca ttgcagcact ggggccagat   4140
ggtaagccct cccgtatcgt agttatctac acgacgggga gtcaggcaac tatggatgaa   4200
cgaaatagac agatcgctga gataggtgcc tcactgatta gcattggta actgtcagac    4260 caagtttact catatatact ttagattgat ttaaaacttc attttaatt taaaaggatc    4320 taggtgaaga tccttttga taatctcatg accaaaatcc cttaacgtga gttttcgttc    4380
cactgagcgt cagaccccgt agaaaagatc aaaggatctt cttgagatcc ttttttctg    4440 cgcgtaatct gctgcttgca aacaaaaaaa ccaccgctac cagcggtggt ttgtttgccg   4500
gatcaagagc taccaactct ttttccgaag gtaactggct tcagcagagc gcagatacca   4560
aatactgtcc ttctagtgta gccgtagtta ggccaccact tcaagaactc tgtagcaccg   4620
cctacatacc tcgctctgct aatcctgtta ccagtggctg ctgccagtgg cgataagtcg   4680
tgtcttaccg ggttggactc aagacgatag ttaccggata aggcgcagcg gtcgggctga   4740
acggggggtt cgtgcacaca gcccagcttg gagcgaacga cctacaccga actgagatac   4800
ctacagcgtg agctatgaga aagcgccacg cttcccgaag ggagaaaggc ggacaggtat   4860
```

```
ccggtaagcg gcagggtcgg aacaggagag cgcacgaggg agcttccagg gggaaacgcc    4920
tggtatcttt atagtcctgt cgggtttcgc cacctctgac ttgagcgtcg atttttgtga    4980
tgctcgtcag gggggcggag cctatggaaa acgccagca acgcggcctt tttacggttc     5040
ctggcctttt gctggccttt tgctcacatg ttctttcctg cgttatcccc tgattctgtg    5100
gataaccgta ttaccgcctt tgagtgagct gataccgctc gccgcagccg aacgaccgag    5160
cgcagcgagt cagtgagcga ggaagcggaa gagcgcctga tgcggtattt tctccttacg    5220
catctgtgcg gtatttcaca ccgcatatgg tgcactctca gtacaatctg ctctgatgcc    5280
gcatagttaa gccagtatac actccgctat cgctacgtga ctgggtcatg gctgcgcccc    5340
gacacccgcc aacacccgct gacgcgccct gacgggcttg tctgctcccg gcatccgctt    5400
acagacaagc tgtgaccgtc tccgggagct gcatgtgtca gaggttttca ccgtcatcac    5460
cgaaacgcgc gaggcagcag atcaattcgc gcgcgaaggc gaagcggcat gcatttacgt    5520
tgacaccatc gaatggtgca aaacctttcg cggtatggca tgatagcgcc cggaagagag    5580
tcaattcagg gtggtgaatg tgaaaccagt aacgttatac gatgtcgcag agtatgccgg    5640
tgtctcttat cagaccgttt cccgcgtggt gaaccaggcc agccacgttt ctgcgaaaac    5700
gcgggaaaaa gtggaagcgg cgatggcgga gctgaattac attcccaacc gcgtggcaca    5760
acaactggcg ggcaaacagt cgttgctgat tggcgttgcc acctccagtc tggccctgca    5820
cgcgccgtcg caaattgtcg cggcgattaa atctcgcgcc gatcaactgg gtgccagcgt    5880
ggtggtgtcg atggtagaac gaagcggcgt cgaagcctgt aaagcggcgg tgcacaatct    5940
tctcgcgcaa cgcgtcagtg ggctgatcat taactatccg ctggatgacc aggatgccat    6000
tgctgtggaa gctgcctgca ctaatgttcc ggcgttattt cttgatgtct ctgaccagac    6060
acccatcaac agtattattt tctcccatga agacggtacg cgactgggcg tggagcatct    6120
ggtcgcattg ggtcaccagc aaatcgcgct gttagcgggc ccattaagtt ctgtctcggc    6180
gcgtctgcgt ctggctggct ggcataaata tctcactcgc aatcaaattc agccgatagc    6240
ggaacgggaa ggcgactgga gtgccatgtc cggttttcaa caaaccatgc aaatgctgaa    6300
tgagggcatc gttcccactg cgatgctggt tgccaacgat cagatggcgc tgggcgcaat    6360
gcgcgccatt accgagtccg ggctgcgcgt tggtgcggat atctcggtag tgggatacga    6420
cgataccgaa gacagctcat gttatatccc gccgtcaacc accatcaaac aggattttcg    6480
cctgctgggg caaaccagcg tggaccgctt gctgcaactc tctcagggcc aggcggtgaa    6540
gggcaatcag ctgttgcccg tctcactggt gaaaagaaaa accaccctgg cgcccaatac    6600
gcaaaccgcc tctccccgcg cgttggccga ttcattaatg cagctggcac gacaggtttc    6660
ccgactggaa agcgggcagt gagcgcaacg caattaatgt gagttagcgc gaattgatct    6720
g                                                                   6721
```

<210> SEQ ID NO 9
<211> LENGTH: 6685
<212> TYPE: DNA
<213> ORGANISM: Artificial Sequence
<220> FEATURE:
<223> OTHER INFORMATION: SYNTHESIZED

<400> SEQUENCE: 9

```
gtttgacagc ttatcatcga ctgcacggtg caccaatgct tctggcgtca ggcagccatc      60
ggaagctgtg gtatggctgt gcaggtcgta atcactgca taattcgtgt cgctcaaggc     120
gcactcccgt tctggataat gttttttgcg ccgacatcat aacggttctg gcaaatattc     180
```

```
tgaaatgagc tgttgacaat taatcatccg gctcgtataa tgtgtggaat tgtgagcgga   240
taacaatttc acacaggaaa cagcgccgct gagaaaaagc gaagcggcac tgctctttaa   300
caatttatca gacaatctgt gtgggcactc gaccggaatt atcgattaac tttattatta   360
aaaattaaag aggtatatat taatgtatcg attaaataag gaggaataaa ccatggtgag   420
caagggcgcc gagctgttca ccggcatcgt gcccatcctg atcgagctga atggcgatgt   480
gaatggccac aagttcagcg tgagcggcga gggcgagggc gatgccacct acggcaagct   540
gaccctgaag ttcatctgca ccaccggcaa gctgcctgtg ccctggccca ccctggtgac   600
caccctgagc tacggcgtgc agtgcttctc acgctacccc gatcacatga agcagcacga   660
cttcttcaag agcgccatgc ctgagggcta catccaggag cgcaccatct tcttcgagga   720
tgacggcaac tacaagtcgc gcgccgaggt gaagttcgag ggcgataccc tggtgaatcg   780
catcgagctg accggcaccg atttcaagga ggatggcaac atcctgggca taagatgga   840 gtacaactac aacgcccaca atgtgtacat catgaccgac aaggcaaga atggcatcaa   900 ggtgaacttc aagatccgcc acaacatcga ggatggcagc gtgcagctgg ccgaccacta   960
ccagcagaat accccatcg gcgatggccc tgtgctgctg cccgataacc actacctgtc  1020
cacccagagc gccctgtcca aggaccccaa cgagaagcgc gatcacatga tctacttcgg  1080
cttcgtgacc gccgccgcca tcacccacgg catggatgag ctgtacaagt ccggagacga  1140
taacactatg tctgtagtgc gcaaggctat tgagcaagat gcgaaagccg cgccagatgt  1200
tcagctgctg atgaatgatt ctcagaatga ccagtccaag cagaacgatc agatcgacgt  1260
attgctggcg aaaggggtga aggcactggc aatcaacctg gttgacccgg cagctgcggg  1320
tacggtgatt gagaaagcgc gtgggcaaaa cgtgccggtg gttttcttca acaaagaacc  1380
gtctcgtaag gcgctggata gctacgacaa agcctactac gttggcactg actccaaaga  1440
gtccggcatt attcaaggcg atttgattgc taaacactgg gcggcgaatc agggttggga  1500
tctgaacaaa gacggtcaga ttcagttcgt actgctgaaa ggtgaaccgg ccatccggga  1560
tgcagaagca cgtaccactt acgtgattaa agaattgaac gataaaggca tcaaaactga  1620
acagttacag ttagataccg caatgtggga caccgctcag gcgaaagata gatggacgc  1680 ctggctgtct ggcccgaacg ccaacaaaat cgaagtggtt atcgccaaca acgatgcgat  1740
ggcaatgggc gcggttgaag cgctgaaagc acacaacaag tccagcattc cggtgtttgg  1800
cgtcgatgcg ctgccagaag cgctggcgct ggtgaaatcc ggtgcactgg cgggcaccgt  1860
actgaacgat gctaacaacc aggcgaaagc gacctttgat ctggcgaaaa acctggccga  1920
tggtaaaggt gcggctgatg caccaactg gaaaatcgac aacaaagtgg tccgcgtacc  1980
ttatgttggc gtagataaag acaacctggc tgaattcagc aagaaaatga tggtgagcaa  2040
gggcgaggag gataacatgg ccatcatcaa ggagttcatg cgcttcaagg tgcacatgga  2100
gggctccgtg aacggccacg agttcgagat cgagggcgag ggcgagggcc gcccctacga  2160
gggcacccag accgccaagc tgaaggtgac caagggtggc cccctgccct tcgcctggga  2220
catcctgtcc cctcagttca tgtacggctc caaggcctac gtgaagcacc ccgccgacat  2280
ccccgactac ttgaagctgt ccttccccga gggcttcaag tgggagcgcg tgatgaactt  2340
cgaggacggc ggcgtggtga ccgtgaccca ggactcctcc ctgcaggacg gcgagttcat  2400
ctacaaggtg aagctgcgcg gcaccaactt cccctccgac ggccccgtaa tgcagaagaa  2460
gaccatgggc tgggaggcct cctccgagcg gatgtacccc gaggacggcg ccctgaaggg  2520
cgagatcaag cagaggctga agctgaagga cggcggccac tacgacgctg aggtcaagac  2580
```

```
cacctacaag gccaagaagc ccgtgcagct gcccggcgcc tacaacgtca acatcaagtt    2640
ggacatcacc tcccacaacg aggactacac catcgtggaa cagtacgaac gcgccgaggg    2700
ccgccactcc accggcggca tggacgagct gtacaagcaa gcttacgtag aacaaaaact    2760
catctcagaa gaggatctga atagcgccgt cgaccatcat catcatcatc attgagttta    2820
aacggtctcc agcttggctg ttttggcgga tgagagaaga ttttcagcct gatacagatt    2880
aaatcagaac gcagaagcgg tctgataaaa cagaatttgc ctggcggcag tagcgcggtg    2940
gtcccacctg accccatgcc gaactcagaa gtgaaacgcc gtagcgccga tggtagtgtg    3000
gggtctcccc atgcgagagt agggaactgc caggcatcaa ataaaacgaa aggctcagtc    3060
gaaagactgg gcctttcgtt ttatctgttg tttgtcggtg aacgctctcc tgagtaggac    3120
aaatccgccg ggagcggatt tgaacgttgc gaagcaacgg cccggagggt ggcgggcagg    3180
acgcccgcca taaactgcca ggcatcaaat taagcagaag gccatcctga cggatggcct    3240
ttttgcgttt ctacaaactc tttttgttta ttttctaaa tacattcaaa tatgtatccg    3300
ctcatgagac aataaccctg ataaatgctt caataatatt gaaaaggaa gagtatgagt    3360 attcaacatt tccgtgtcgc ccttattccc ttttttgcgg cattttgcct tcctgttttt    3420
gctcacccag aaacgctggt gaaagtaaaa gatgctgaag atcagttggg tgcacgagtg    3480
ggttacatcg aactggatct caacagcggt aagatccttg agagttttcg ccccgaagaa    3540
cgttttccaa tgatgagcac ttttaaagtt ctgctatgtg gcgcggtatt atcccgtgtt    3600
gacgccgggc aagagcaact cggtcgccgc atacactatt ctcagaatga cttggttgag    3660
tactcaccag tcacagaaaa gcatcttacg gatggcatga cagtaagaga attatgcagt    3720
gctgccataa ccatgagtga taacactgcg gccaacttac ttctgacaac gatcggagga    3780
ccgaaggagc taaccgcttt tttgcacaac atgggggatc atgtaactcg ccttgatcgt    3840
tgggaaccgg agctgaatga agccatacca aacgacgagc gtgacaccac gatgcctgta    3900
gcaatggcaa caacgttgcg caaactatta actggcgaac tacttactct agcttcccgg    3960
caacaattaa tagactggat ggaggcggat aaagttgcag gaccacttct gcgctcggcc    4020
cttccggctg gctggtttat tgctgataaa tctggagccg gtgagcgtgg gtctcgcggt    4080
atcattgcag cactggggcc agatggtaag ccctcccgta tcgtagttat ctacacgacg    4140
gggagtcagg caactatgga tgaacgaaat agacagatcg ctgagatagg tgcctcactg    4200
attaagcatt ggtaactgtc agaccaagtt tactcatata tactttagat tgatttaaaa    4260
cttcattttt aatttaaaag gatctaggtg aagatccttt ttgataatct catgaccaaa    4320
atcccttaac gtgagttttc gttccactga gcgtcagacc ccgtagaaaa gatcaaagga    4380
tcttcttgag atcctttttt tctgcgcgta atctgctgct tgcaaacaaa aaaaccaccg    4440
ctaccagcgg tggtttgttt gccggatcaa gagctaccaa ctcttttcc gaaggtaact    4500 ggcttcagca gagcgcagat accaaatact gtccttctag tgtagccgta gttaggccac    4560
cacttcaaga actctgtagc accgcctaca tacctcgctc tgctaatcct gttaccagtg    4620
gctgctgcca gtggcgataa gtcgtgtctt accgggttgg actcaagacg atagttaccg    4680
gataaggcgc agcggtcggg ctgaacgggg ggttcgtgca cacagcccag cttggagcga    4740
acgacctaca ccgaactgag atacctacag cgtgagctat gagaaagcgc cacgcttccc    4800
gaagggagaa aggcggacag gtatccggta agcggcaggg tcggaacagg agagcgcacg    4860
agggagcttc caggggaaa cgcctggtat ctttatagtc ctgtcgggtt tcgccacctc    4920
tgacttgagc gtcgattttt gtgatgctcg tcagggggc ggagcctatg gaaaaacgcc    4980
```

-continued

```
agcaacgcgg ccttttacg gttcctggcc ttttgctggc cttttgctca catgttcttt    5040
cctgcgttat cccctgattc tgtggataac cgtattaccg cctttgagtg agctgatacc    5100
gctcgccgca gccgaacgac cgagcgcagc gagtcagtga gcgaggaagc ggaagagcgc    5160
ctgatgcggt attttctcct tacgcatctg tgcggtattt cacaccgcat atggtgcact    5220
ctcagtacaa tctgctctga tgccgcatag ttaagccagt atacactccg ctatcgctac    5280
gtgactgggt catggctgcg ccccgacacc cgccaacacc cgctgacgcg ccctgacggg    5340
cttgtctgct cccggcatcc gcttacagac aagctgtgac cgtctccggg agctgcatgt    5400
gtcagaggtt ttcaccgtca tcaccgaaac gcgcgaggca gcagatcaat tcgcgcgcga    5460
aggcgaagcg gcatgcattt acgttgacac catcgaatgg tgcaaaacct ttcgcggtat    5520
ggcatgatag cgcccggaag agagtcaatt cagggtggtg aatgtgaaac cagtaacgtt    5580
atacgatgtc gcagagtatg ccggtgtctc ttatcagacc gtttcccgcg tggtgaacca    5640
ggccagccac gtttctgcga aaacgcggga aaaagtggaa gcggcgatgg cggagctgaa    5700
ttacattccc aaccgcgtgg cacaacaact ggcgggcaaa cagtcgttgc tgattggcgt    5760
tgccacctcc agtctggccc tgcacgcgcc gtcgcaaatt gtcgcggcga ttaaatctcg    5820
cgccgatcaa ctgggtgcca gcgtggtggt gtcgatggta gaacgaagcg gcgtcgaagc    5880
ctgtaaagcg gcggtgcaca atcttctcgc gcaacgcgtc agtgggctga tcattaacta    5940
tccgctggat gaccaggatg ccattgctgt ggaagctgcc tgcactaatg ttccggcgtt    6000
atttcttgat gtctctgacc agacacccat caacagtatt attttctccc atgaagacgg    6060
tacgcgactg ggcgtggagc atctggtcgc attgggtcac cagcaaatcg cgctgttagc    6120
gggcccatta agttctgtct cggcgcgtct gcgtctggct ggctggcata aatatctcac    6180
tcgcaatcaa attcagccga tagcggaacg ggaaggcgac tggagtgcca tgtccggttt    6240
tcaacaaacc atgcaaatgc tgaatgaggg catcgttccc actgcgatgc tggttgccaa    6300
cgatcagatg gcgctgggcg caatgcgcgc cattaccgag tccgggctgc gcgttggtgc    6360
ggatatctcg gtagtgggat acgacgatac cgaagacagc tcatgttata tcccgccgtc    6420
aaccaccatc aaacaggatt ttcgcctgct ggggcaaacc agcgtggacc gcttgctgca    6480
actctctcag ggccaggcgg tgaagggcaa tcagctgttg cccgtctcac tggtgaaaag    6540
aaaaaccacc ctggcgccca atacgcaaac cgcctctccc cgcgcgttgg ccgattcatt    6600
aatgcagctg gcacgacagg tttcccgact ggaaagcggg cagtgagcgc aacgcaatta    6660
atgtgagtta gcgcgaattg atctg                                          6685
```

PH-INSENSITIVE GLUCOSE INDICATOR PROTEIN

CROSS REFERENCE TO RELATED APPLICATIONS

This application claims the priority of U.S. provisional application No. 61/250,118, filed Oct. 9, 2009, which is hereby incorporated by reference in its entirety.

GOVERNMENTAL RIGHTS

This invention was made with governmental support under contract number 1R15 EB006378 awarded by the National Institutes of Health. The government has certain rights in the invention.

FIELD OF THE INVENTION

The present invention encompasses a glucose indicator protein.

BACKGROUND OF THE INVENTION

Diabetes mellitus is one of the major health care problems in the world. It affects 16 million people in the United States and over 100 million people worldwide. More frequent monitoring of blood glucose can prevent many long-term complications associated with diabetes. Although finger-stick testing is currently available for blood glucose monitoring, the nature of this test restricts its utility for maintaining a strict level of blood glucose. This has resulted in a worldwide effort to develop noninvasive methods for fast, painless, and convenient monitoring of glucose.

Most biosensors use proteins, which provide the desired analytic specificity, but often are not appropriate for noninvasive detection because they lack an intrinsic signal transduction mechanism. A variety of glucose binding proteins have been isolated and well characterized. These proteins are highly specific for glucose binding, but do not provide any optical signal in the visible region upon glucose binding.

To date, glucose biosensors are pH sensitive, and will not work properly in certain in vivo applications, where the pH can vary with the metabolic activity of the cell. In addition, the glucose binding proteins used to develop the biosensors have a high glucose affinity not suitable for detecting physiological concentrations of glucose.

Therefore, there is a need for pH-insensitive glucose biosensors with intrinsic signal transduction mechanisms to provide non-invasive methods of monitoring a wide range of glucose concentrations in vivo.

SUMMARY OF THE INVENTION

One aspect of the present invention encompasses a pH insensitive glucose indicator protein (GIP). The GIP comprises a glucose binding protein that changes conformation upon exposure to glucose, wherein said glucose binding protein comprises a phenyl alanine, valine, cysteine, threonine, or leucine at the amino acid position equivalent to amino acid position 16 of the mature *E. Coli* glucose/galactose binding protein. The GIP also comprises at least one pH insensitive fluorescence donor coupled to the glucose binding protein, and at least one pH insensitive fluorescence acceptor coupled to the glucose binding protein, wherein the conformational changes of the glucose binding protein upon binding or releasing glucose produces a detectable and reversible signal change.

Another aspect of the present invention encompasses a biosensor. The biosensor comprising at least two pH insensitive glucose indicator proteins (GIP), wherein each GIP comprises a glucose binding protein that changes conformation upon exposure to glucose, wherein said glucose binding protein comprises a phenyl alanine, valine, cysteine, threonine, or leucine at the amino acid position equivalent to amino acid position 16 of the mature *E. Coli* glucose/galactose binding protein; at least one pH insensitive fluorescence donor coupled to said glucose binding protein; and at least one pH insensitive fluorescence acceptor coupled to said glucose binding protein, wherein the conformational changes of the glucose binding protein upon binding or releasing glucose produces a detectable and reversible signal change.

Yet another aspect of the present invention encompasses an in vivo method for determining the concentration of glucose. The method comprises providing a biosensor comprising at least two pH insensitive glucose indicator proteins (GIP), wherein each GIP comprises: a glucose binding protein that changes conformation upon exposure to glucose, wherein said glucose binding protein comprises a phenyl alanine, valine, cysteine, threonine, or leucine at the amino acid position equivalent to amino acid position 16 of the mature *E. Coli* glucose/galactose binding protein; at least one pH insensitive fluorescence donor coupled to said glucose binding protein; and at least one pH insensitive fluorescence acceptor coupled to said glucose binding protein, wherein the conformational changes of the glucose binding protein upon binding or releasing glucose produces a detectable and reversible signal change. The method further comprises exposing said biosensor to varying glucose concentrations and measuring any change in the signal produced to determine the concentration of glucose.

Other aspects and iterations of the invention are described more thoroughly below.

REFERENCE TO COLOR FIGURES

The application file contains at least one photograph executed in color. Copies of this patent application publication with color photographs will be provided by the Office upon request and payment of the necessary fee.

BRIEF DESCRIPTION OF THE FIGURES

FIG. 1 depicts the amino acid sequence of glucose binding protein isolated from *E. coli* K12 (SEQ ID NO: 1). A leader peptide signal sequence and the leader peptide cleavage site are shown.

FIG. 3 depicts the design of a glucose indicator protein (GIP) for sensing glucose based on FRET. (A) Diagram of the GIP structure showing how FRET between two green fluorescent proteins can measure glucose concentration. The GBP adopts an open form in the presence of glucose which triggers a conformation change causing the two GFP molecules to move apart, decreasing FRET. The black dot represents one molecule of glucose bound to the binding site of the GBP. GFPuv: green fluorescent protein with several mutations to enhance the xcitation by UV light. YFP: yellow fluorescent protein. GBP: glucose binding protein. FRET: fluorescence resonance energy transfer. (B) Domain structure of the GIP. The boundary region of amino acid sequence between the fused proteins was determined empirically to ensure the stable and efficient expression of GIP in E. coli. (C) Spectral overlap of GFPuv and YFP. The absorbance spectra are denoted by black lines, and emission spectra are denoted by gray lines.

FIG. 4 depicts the spectral properties of GIP and YFP-GBP. (A) The emission spectra of GIP at different wavelengths in the absence of glucose. Line a represents the emission spectrum of GIP excited at 395 nm, and line b represents the emission spectrum of GIP excited at 513 nm. (B) The excitation and emission spectra of YFP-GBP. Dotted line represents the emission spectrum, and the solid line represents the excitation spectrum.

FIG. 9 depicts the glucose titration curves of GIPs at vatying pH values. (A) pH-sensitive GIP. (B) pH-insensitive GIP. The experiments were performed at room temperature and glucose was titrated into the GIP solution. The slit width for both excitation and emission wavelengths were set at 10 nm. The fluorescent intensities of the ECFP and YFP were measured 10 min after the addition of glucose. The data shown are the mean values of three experiments and the error bars show the standard deviations (+/−SD).

FIG. 20 depicts the uptake of glucose in two segments of a cell. The tau values were found to be about 45 s.

FIG. 26 depicts a sequence encoding sequence of $GIP_i$-Thr (SEQ ID NO: 2).

FIG. 27 depicts a sequence encoding sequence of $GIP_i$-Cys (SEQ ID NO: 3).

FIG. 28 depicts a sequence encoding sequence of $GIP_i$-Leu (SEQ ID NO: 4).

FIG. 29 depicts a sequence encoding sequence of $GIP_i$-Val (SEQ ID NO: 5).

FIG. 30 depicts a sequence encoding sequence of a plasmid encoding the GIP: AcGFP-GBPval-mCherry (SEQ ID NO: 6).

FIG. 31 depicts a sequence encoding sequence of a plasmid encoding AcGFP-GBPcys-mCherry (SEQ ID NO: 7).

FIG. 32 depicts a sequence encoding sequence of a plasmid encoding AcGFP-GBPthr-mCherry (SEQ ID NO: 8).

FIG. 33 depicts a sequence encoding sequence of a plasmid encoding the AcGFP-GBPthrDelta12-mCherry (SEQ ID NO: 9).

DETAILED DESCRIPTION OF THE INVENTION

Figure 2:
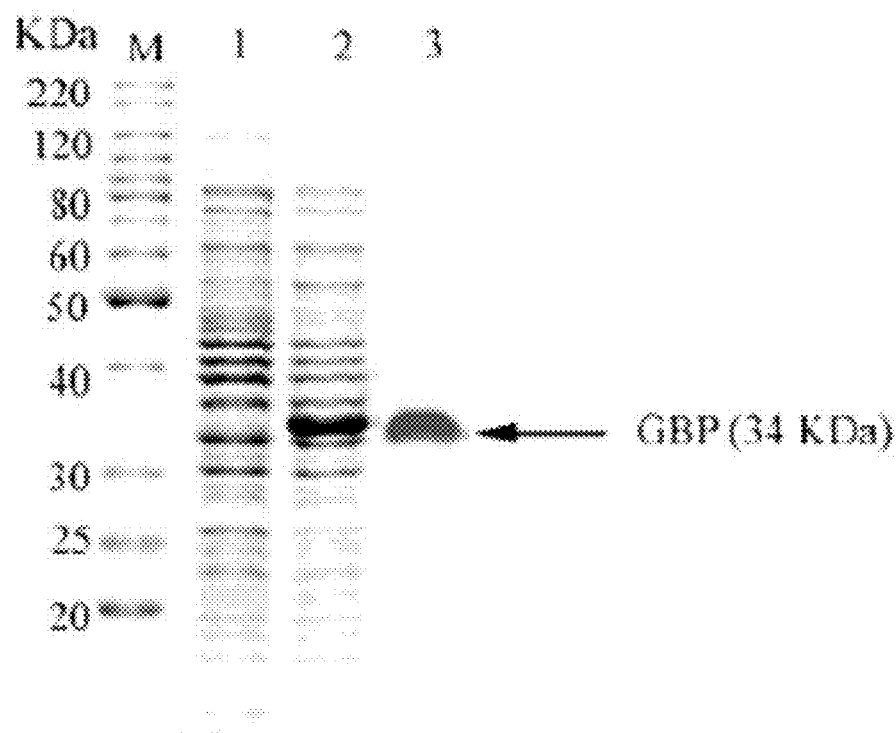
FIG. 2 depicts the SDS-PAGE analysis of GBP expression in *E. coli*. Lane M: protein molecular weight marker; Lane 1: control wild type *E. coli* lysate; Lane 2: lysate of *E. coli* expressing GBP; Lane 3: GBP purified by immobilized metal affinity purification.

A glucose indicator protein (GIP) has been developed. Significantly, the GIP is insensitive to in vivo pH changes. Additionally, the GIP is sensitive to a wide range of glucose concentrations. Advantageously, a GIP of the invention may be used to measure in vivo glucose concentrations.

I. Glucose Indicator Protein

One aspect of the present invention encompasses a glucose indicator protein (GIP). Generally speaking, a GIP comprises a glucose binding protein, a fluorescence donor, and a fluorescence acceptor. Conformational changes in the glucose binding protein caused by glucose binding results in a change in fluorescent resonance energy between the fluorescent acceptor and donor, resulting in a detectable signal. Components of the GIP are discussed in more detail below.

(a) Glucose Binding Protein

A GIP of the invention comprises a glucose binding protein. As used herein, "glucose binding protein" refers to a protein that changes conformation upon glucose binding. A glucose binding protein should be capable of reversibly binding glucose. In some embodiments, a glucose binding protein may be a glucose/galactose binding protein (GGBP) belonging to the family of bacterial periplasmic-binding proteins. In an exemplary embodiment, a glucose binding protein is the glucose/galactose binding protein of *E. coli*. In a further exemplary embodiment, a glucose binding protein is the GGBP of *E. coli* K12 encoded by mgIB. The *E. coli* GGBP comprises a leader peptide signal sequence that is cleaved upon maturation of the protein (see FIG. 1A). In some embodiments, the glucose binding protein of the invention comprises the full length GGBP (including the leader sequence). In other embodiments, the glucose binding protein of the invention comprises the mature GGBP (without the leader sequence).

In some embodiments, the invention comprises a wild type GGBP. In other embodiments, the invention comprises a mutated GGBP. A mutated GGBP refers to a binding protein that contains one or more amino acids that have been substituted for, deleted from, or added to the amino acids present in the wild type protein. In one embodiment, a mutation may affect the pH sensitivity of the binding protein. In another embodiment, a mutation may be made in a residue of the binding protein that contacts glucose, or that is involved in glucose binding. Stated another way, a mutation may alter the affinity of the binding protein for glucose, or alter the Kd. In some embodiments, the amino acid at position 16 of the mature *E. coli* GGBP, or the equivalent amino acid position in another GGBP, may be mutated. In other embodiments, the amino acid at position 183 of the mature *E. coli* GGBP, or the equivalent amino acid position in another GGBP, may be mutated. By way of non-limiting example, the phenylalanine at position 16 may be substituted by valine, cysteine, threonine, or leucine. In one embodiment, a glucose binding protein comprises the *E. Coli* K12 GGBP with a phenylalanine at position 16. In another embodiment, a glucose binding protein comprises the *E. Coli* K12 GGBP with a valine at position 16. In yet another embodiments, a glucose binding protein comprises the *E. Coli* K12 GGBP with a cysteine at position 16. In still another embodiment, a glucose binding protein comprises the *E. Coli* K12 GGBP with a threonine at position 16. In a further embodiment, a glucose binding protein comprises the *E. Coli* K12 GGBP with a leucine at position 16.

In an alternative embodiment, a glucose binding protein may comprise an *E. coli* GGBP with an N-terminus deletion. The deletion may comprise about 1, 2, 3, 4, 5, 6, 7, 8, 9, 10, 11, 12, 13, 14, 15, or more than 15 amino acids.

In some embodiments of the invention, the Kd value for glucose and the glucose binding protein are from about 0.0001 mM to about 20 mM. For instance, the Kd value may be about 0.0001, 0.001, 0.01, 0.1, 1, 10, or 20 mM. Alternatively, the Kd value may be between about 0.0001 mM and about 0.001 mM, between about 0.001 mM and about 0.01 mM, between about 0.01 mM and about 0.1 mM, between about 0.1 mM and about 1 mM, between about 1 mM and about 10 mM, or between about 10 mM and about 20 mM. In an exemplary embodiment, the Kd value ranges from about 0.01 mM to about 10 mM. In another exemplary embodiment, the Kd value may be about 0.01, 0.05, 0.1, 0.15, 0.2. 0.25, 0.3, 0.35, 0.4, 0.45, 0.5, 0.55, 0.6, 0.65, 0.7, 0.75, 0.8, 0.85, 0.9, 0.95, 1.0, 1.5, 2.0, 2.5, 3.0, 3.5, 4.0, 4.5, 5.0, 5.5, 6.0, 6.5, 7.0, 7.5, 8.0, 8.5, 9.0. 9.5, or 10.0 mM.

(b) Fluorescent Donor and Acceptor

The glucose indicator protein comprises at least one fluorescence donor and at least one fluorescence acceptor coupled to the glucose binding protein. Typically, the fluorescence donor and the fluorescence acceptor may be a fluorescent protein, a quantum dot, or a dye. In preferred embodiments, the fluorescence donors and acceptors are fluorescent proteins. Non-limiting examples of fluorescent proteins may include fluorescent proteins isolated from *Aequorea victoria, Aequorea coerulescens, Renilla reniformis, Zoanthus* sp., *Anemonia majano, Anemonia sulcata, Heteractis crispa, Discosoma striata, Clavularia* sp. and *Phialidium gregarium*. Further non-limiting examples may include variants of wild-type fluorescent proteins that possess improved fluorescence, improved stability, different physiological requirements, or altered excitation emission spectra. Suitable examples are known in the art. In one embodiment, the fluorescence donor or acceptor may be *Aequoria victoria* green fluorescent protein (GFP), *Aequorea coerulescens* GFP (AcGFP), enhanced green fluorescent protein (EGFP), GFPuv, blue fluorescent protein (BFP), cyan fluorescent protein (CFP), enhanced cyan fluorescent protein (ECFP), yellow fluorescent protein (YFP), the pH insensitive variant of YFP ($YFP_i$), red fluorescent protein (RFP), amFP486, cFP484, drFP583, and mCherry.

In preferred embodiments, the fluorescence donor and the fluorescence acceptor of the invention are pH insensitive. Insensitivity to pH may be a natural characteristic of the wild type form of the fluorescent protein, or may be the result of specific mutations of the fluorescent protein. Non-limiting examples of pH insensitive fluorescence donors and fluorescence acceptors may include YFPi, CFP, AcGFP and mCherry.

More than one fluorescent donor or fluorescent acceptor may be coupled to the glucose binding protein. For instance, in some embodiments, three fluorescence donors and one fluorescence acceptor may be coupled to the glucose binding protein. In other embodiments, one fluorescence donor and three fluorescence acceptors may be coupled to the glucose binding protein. In certain embodiments, three fluorescence donors and two fluorescence acceptors may be coupled to the glucose binding protein. In one embodiment, two fluorescence donors and three fluorescence acceptors may be coupled to the glucose binding protein. In another embodiment, two fluorescence donors and one fluorescence acceptor may be coupled to the glucose binding protein. In yet another embodiment, one fluorescence donor and two fluorescence acceptors may be coupled to the glucose binding protein. In still other embodiments, two fluorescence donors and two fluorescence acceptors may be coupled to the glucose binding protein. In an alternative embodiment, one fluorescence donor and one fluorescence acceptor may be coupled to the glucose binding protein.

One or more fluorescence donors or fluorescence acceptors may either be coupled to the N-terminus or the C-terminus of the glucose binding protein. In some embodiments, one or more fluorescence donors are coupled to the C-terminus of the glucose binding protein, and one or more fluorescence acceptors are coupled to the N-terminus of the glucose binding protein. In other embodiments, one or more fluorescence donors are coupled to the N-terminus of the glucose binding protein, and one or more fluorescence acceptors are coupled to the C-terminus of the glucose binding protein.

Glucose binding effects a change in conformation of the glucose binding protein that alters the relative position of the fluorescence donor and fluorescence acceptor. This results in increased separation of the donor and acceptor, and results in a change in FRET signal. For excitation transfer from donor to acceptor to occur, the absorption spectrum of the acceptor must overlap the fluorescence emission spectrum of the donor. As a result, the selection of a donor limits the selection of an acceptor, and similarly, the selection of an acceptor limits the selection of a donor. Selection of an appropriate donor and acceptor pairs may be performed by one of skill in the art. Non-limiting examples of suitable pairs of fluorescence donors and fluorescence acceptors capable of producing a FRET signal may include BFP and GFP, GFPuv and YFP, CFP and YFP, ECFP and YFPi, AcGFP and mCherry. In one embodiment, a suitable pair comprises ECFP and YFPi. In another embodiment, a suitable pair comprises AcGFP and mCherry.

(c) Isolation Tags

The glucose indicator protein of the invention may also comprise a tag to simplify isolation. In some embodiments, the glucose indicator protein may be operably linked to an antibody epitope such that the glucose indicator protein is epitope tagged. Non-limiting examples of suitable antibody epitope tags may include AcV5, AU1, AU5, E, ECS, E2, FLAG, Glu-Glu, HSV, KT3, myc, S, S1, T7, V5, VSV-G, TAP tag, DDDDK, and 6×His. In one embodiment, the epitope tag may be a 6×His tag. The location of the antibody epitope tag may vary depending upon the embodiment. For instance, in one embodiment, the epitope tag may be located at the carboxyl terminus of the glucose binding protein. In another embodiment, the epitope tag may be located at the carboxyl terminus of the fluorescence donor. In yet another embodiment, the epitope tag may be located at the amino terminus of the fluorescence donor. In still another embodiment, the epitope tag may be located at the carboxyl terminus of the fluorescence acceptor. In still yet another embodiment, the epitope tag may be located at the amino terminus of the fluorescence acceptor. In certain embodiments, the epitope tag may be located at the amino terminus of the glucose binding protein.

(d) Coupling

The fluorescent acceptor and donor may be coupled to the glucose binding protein through standard molecular biology procedures well known to those of skill in the art. In one embodiment, a fluorescent acceptor or donor may be coupled to the glucose binding protein through a linker. The length and flexibility of the linker moiety is generally chosen to optimize both FRET and the kinetics and specificity of conformational changes induced by glucose binding. As is commonly recognized in the art, linkers may be empirically determined. In some embodiments, the linker is a peptide moiety. In other embodiments, the linker is a peptide from about one to about 30 amino acid residues in length. In still other embodiments, the linker is a peptide from about two to about 15 amino acid residues. For instance, the linker may be about 2, 3, 4, 5, 6, 7, 8, 9, 10, 11, 12, 13, 14, or 15 amino acid residues. In one embodiment, the linker between a fluorescence donor and a glucose binding protein may comprise --Thr-Ser--. In another embodiment, the linker between a fluorescence acceptor and a glucose binding protein may comprise --Gly-Thr--. In yet another embodiment, the linker between a fluorescence donor and a glucose binding protein may comprise --Thr-Ser-- and the linker between a fluorescence acceptor and a glucose binding protein may comprise --Gly-Thr--.

(e) Specific GIPs

In some embodiments, a GIP of the invention comprises a GBP, donor and acceptor combination listed in Table A below. In each case, the GBP listed in Table A is the *E. coli* GGBP.

TABLE A

| Position 16 of the GBP | Donor | Acceptor |
|---|---|---|
| phenylalanine | ECFP | YFPi |
| valine | ECFP | YFPi |
| cysteine | ECFP | YFPi |
| threonine | ECFP | YFPi |
| leucine | ECFP | YFPi |
| alanine | ECFP | YFPi |
| phenylalanine | AcGFP | mCherry |
| valine | AcGFP | mCherry |
| cysteine | AcGFP | mCherry |
| threonine | AcGFP | mCherry |
| leucine | AcGFP | mCherry |
| alanine | AcGFP | mCherry |
| phenylalanine | BFP | GFP |
| valine | BFP | GFP |
| cysteine | BFP | GFP |
| threonine | BFP | GFP |
| leucine | BFP | GFP |
| alanine | BFP | GFP |
| phenylalanine | GFPuv | YFP |
| valine | GFPuv | YFP |
| cysteine | GFPuv | YFP |
| threonine | GFPuv | YFP |
| leucine | GFPuv | YFP |
| alanine | GFPuv | YFP |
| phenylalanine | CFP | YFP |
| valine | CFP | YFP |
| cysteine | CFP | YFP |

TABLE A-continued

| Position 16 of the GBP | Donor | Acceptor |
|---|---|---|
| threonine | CFP | YFP |
| leucine | CFP | YFP |
| alanine | CFP | YFP |

(f) Methods of Making a GIP

A GIP of the invention may be synthetically produced, or alternatively, may be expressed in a cell. Methods for expressing a protein in a cell involve the use of molecular cloning techniques well known in the art. Such techniques are described in Sambrook et al., Molecular Cloning—A Laboratory Manual, Cold Spring Harbor Laboratory, Cold Spring Harbor, N.Y., (1989) and Current Protocols in Molecular Biology, F. M. Ausubel et al., eds.

In one embodiment, a GIP may be expressed in a prokaryotic cell. Suitable prokaryotic cells are known in the art. For instance, a GIP may be expressed in *E. coli*. In another embodiment, a GIP may be expressed in a eukaryotic cell. Suitable eukaryotic cells are known in the art. In some embodiments, the eukaryotic cell may be of human origin. In other embodiments, the cell may be of animal origin. In certain embodiments, the cell may be from an established or a primary cell line. Such cell lines may be isolated, characterized, and expanded using standard techniques known to individuals skilled in the art. The cell line may be adherent or non-adherent, or the cell line may be grown under conditions that encourage adherent, non-adherent or organotypic growth using standard techniques known to individuals skilled in the art. The cell line may be contact inhibited or non-contact inhibited. The cell line may be derived from the digestive system, the skeletal system, the muscular system, the nervous system, the endocrine system, the respiratory system, the circulatory system, the reproductive system, the integumentary system, the lymphatic system, or the urinary system. In some embodiments, the cell line may be derived from epithelial tissue. In other embodiments, the cell line may be derived from nervous tissue. In yet other embodiments, the cell line may be derived from connective tissue. In preferred embodiments, the cell line may be derived from muscle tissue. A non-limiting list of cell lines commonly used in the laboratory setting may include Chinese hamster ovary cells (CHO), vero African green monkey kidney cells, C2C12 mouse myoblast, or HeLa human cervical cancer cells. In preferred embodiments, the cell line may be C2C12 mouse myoblast.

In each of the above embodiments, the GIP may be expressed using a plasmid. Suitable plasmids are known in the art.

Isolating and purifying a GIP expressed in a cell may be performed using techniques generally known in the art. For example, affinity purification may be used to isolate a GIP. Alternatively, column chromatography techniques, precipitation protocols and/or other methods for separating proteins may also be used. (see, e.g., Scopes, Protein Purification: Principles and Practice (1982); U.S. Pat. No. 4,673,641; Ausubel et al., supra; and Sambrook et al., supra; and Leonard et al., J. Biol. Chem. 265:10373-10382 (1990).

(g) Encapsulation of a GIP of the Invention

In certain embodiments, a GIP of the invention may be encapsulated in a semi permeable membrane. See, for instance, FIG. 6. Typically, the semi permeable membrane may be selected so as to be permeable to the passage of glucose, but impermeable to the passage of blood clots, cells, and proteins. In some embodiments, the membrane may be selected so as to exclude most materials having a molecular weight of about 5,000 daltons to about 20,000 daltons. In other embodiments, the membrane may be selected so as to exclude most materials having a molecular weight greater than about 10,000 daltons. Non-limiting examples of such enclosures and semi permeable membranes are discussed in Heller, U.S. Pat. No. 5,593,852, Wilkins, U.S. Pat. No. 5,431,160, Hogen Esch, U.S. Pat. No. 5,372,133, Zier, U.S. Pat. No. 4,919,141, and Gough, U.S. Pat. No. 4,703,756, all hereby incorporated in full by reference.

If a semi-permeable membrane encompassing a GIP is to be implanted in a mammalian body, the semi permeable membrane is preferably an inert, nontoxic material. Non-limiting examples of suitable semi permeable material may include cellulose acetate, cellulose, methyl cellulose, polyvinyl alcohol, polyurethane, and combinations thereof. In one embodiment, a GIP may be encapsulated in a cellulose hollow fiber semi permeable membrane.

II. Biosensor Comprising at Least One GIP

Another aspect of the invention encompasses a biosensor comprising at least one GIP. In one embodiment, the biosensor may comprise one GIP. In another embodiment, the biosensor may comprise two GIPs. In yet another embodiment, the biosensor may comprise three GIPs. In still another embodiment, the biosensor may comprise four GIPs. In a further embodiment, the biosensor may comprise five GIPs. In yet a further embodiment, the biosensor may comprise six GIPs. In an alternative embodiment, the biosensor may comprise seven GIPs. In another alternative embodiment, the biosensor may comprise eight GIPs. In still another alternative embodiment, the biosensor may comprise nine GIPs. In some embodiments, the biosensor may comprise ten GIPs. In other embodiments, the biosensor may comprise more than ten GIPs.

Suitable GIPs include those detailed in section I above. In an exemplary embodiment, suitable GIPs include those detailed in Table A above. In some embodiments, a biosensor of the invention may be encapsulated as detailed in section 1(g) above.

III. Method for In Vivo Detection of Glucose

Yet another aspect of the present invention encompasses a method for detecting and measuring in vivo glucose concentration. Generally, such a method comprises contacting a GIP or biosensor of the invention with glucose in vivo, and detecting the change in FRET, wherein the change in FRET is correlated with a change in glucose concentration.

In some embodiments, a GIP or biosensor of the invention may be exposed to glucose when expressed in a cell. Suitable cells may be grown, sub-cultured, stored and manipulated using standard techniques known to individuals skilled in the art. Generally speaking, the cells should be maintained in effective conditions, meaning conditions that support cell growth/proliferation if essentially no other regulatory compounds are present that would interfere with cell growth/proliferation. The number of cells seeded for the assay will vary with growth conditions as cell growth can be influenced by many factors such as the size of the container used, the rate of growth of the cells used, and composition of the media used to grow the cells.

In other embodiments, a GIP or biosensor of the invention may be exposed to glucose by directly contacting a GIP or biosensor with a solution containing glucose. In an alternative embodiment, a GIP or a biosensor may be exposed to glucose by encapsulating a GIP or biosensor in a semi permeable membrane and exposing the membrane to a solution comprising glucose. Such a solution may comprise blood or interstitial fluid. For more details, see the Examples.

After a GIP or biosensor of the invention is contacted with glucose, the change in FRET may be measured. Methods of measuring FRET are well known in the art and are described in, e.g., "Review in Fluorescence" (2004) Chris D. Geddes (Editor), Joseph R. Lakowicz (Editor), which is hereby incorporated by reference in its entirety. Non-limiting examples of methods to measure FRET may include luminescence spectroscopy, fluorescence microscopy, fluorescent lifetime imaging microscopy (FLIM), and photobleaching FRET. In an exemplary embodiment, the change in FRET may be monitored by FLIM, as detailed in the examples.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

The following examples illustrate various iterations of the invention.

Example 1

Intracellular Expression of Glucose Binding Protein (GBP)

A 32 kDa periplasmic glucose binding protein (GBP) encoded by the mglB gene that serves as a glucose transporter in *Escherichia coli* K12 was selected for this invention (FIG. 1). The initial 23 N-terminal amino acid sequence serves as a leader peptide signal that directs the polypeptide to the bacterial periplasmic space. To ensure the intracellular expression of GBP, the leader peptide signal sequence was deleted from the cDNA of GBP. To facilitate purification, a polyhistidine affinity tag (His)6 was fused to the C-terminus of the GBP.

The protein possesses two distinct helical structural domains, each organized in an a/b folding motif involving the glucose binding region. X-ray structural analysis suggests that the $NH_2$-terminal and COOH-terminal domains are composed of a core of parallel β-sheet flanked by two layers of α-helices.

The expression of intracellular GBP in *E. coli* DH5α transformed with the GBP expression plasmid pTAGBP was determined using SDS-PAGE analysis (FIG. 2) after induction with IPTG. Glucose (4 g/L) was added to the LB media to stabilize the expressed GBP protein. Wild type *E. coli* DH5α lysate served as a control for the assay. The expression of GBP was confirmed in the cell lysate of *E. coli*/DH5α/pTAGBP (lane 2 in FIG. 2) but not in the wild type cell lysate (lane 1 in FIG. 2). The GBP band migrated at a 34 kDa position, which is the expected size of a (His)6-tagged GBP. Clearly, the truncated GBP was efficiently expressed in *E. coli*. Moreover, SDS-PAGE assays showed that the expression of the GBP started from 2 hr post induction and reached a maximum at ~4 to 6 h post induction (data not shown). The expressed GBP could be concentrated nearly 15-fold by an immobilized metal affinity purification (IMAC) column. The purity of GBP eluted from the IMAC column was very high (lane 3 in FIG. 2).

These data demonstrated that GBP could be efficiently expressed intracellularly by the deletion of the leader peptide signal sequence. Previous data in the literature showed low levels of protein expression when confined to the periplasmic space. Thus the methods developed here for the intracellular expression of GBP are of critical importance for large-scale production of GBP for use in glucose biosensors.

Example 2

Construction of the Glucose Indicator Protein (GIP)

The tertiary structure of GBP has two similar N- and C-terminal domains. Both the N- and C-terminal domains are composed of a core of parallel β-sheets flanked by two layers of α-helices. The cleft between the two domains has been identified as the glucose binding site. A calcium binding loop is present in the C-terminal domain. When glucose binds to GBP, the protein undergoes a conformational change, resulting in an alteration of the distance between the C- and N-terminal domains. To achieve a measurable signal upon glucose binding, fluorescent reporter proteins were fused to GBP in such a manner that the spatial separation between the fluorescent moieties changes when the ligand binds (FIG. 3A). As the diameter of GBP is about 50 Angstroms, it will provide a separation between the two reporter proteins and allows the fluorescence energy transfer technique to be used for glucose.

To construct a GIP, two fluorescent proteins were fused, one to each end of the GBP. The amino acid sequences of the boundary region between fusion proteins were determined empirically to achieve a correct and stable folding of the fusion protein. In essence, the GIP has four domains (FIG. 3B). The central two domains (of GBP) involve the glucose binding region that undergoes a change in conformation upon glucose binding. The other two peripheral domains are the added green fluorescent proteins. GFPuv, which was fused to the C-terminus of GBP, served as a donor to transfer the fluorescence energy to the receptor YFP that was fused to the other terminus, the N-terminus, of GBP.

GFPuv has a maximum excitation wavelength at 395 nm and a maximum emission wavelength at 510 nm, whereas YFP has a maximum excitation wavelength at 513 nm and a maximum emission wavelength at 527 nm. Thus high energy transfer efficiency can be achieved as a result of the large spectral overlap between the emission spectra of GFPuv and the absorption spectra of YFP (FIG. 3C). When glucose binds to the protein, rearrangement of the flap region located on one side of the hinge β-sheet of GBP occurs. The change in conformation of the GBP moiety upon the binding of glucose, in turn, alters the relative position of GFPuv (donor) and YFP (acceptor) resulting in increased separation and reduction of FRET (FIG. 3A).

Example 3

Fluorescent Resonance Energy Transfer using GIP

The GIP described in Example 2 was expressed in *E. coli*, purified, and dialyzed against sugar-free binding buffer. Sugar-free proteins were concentrated by ultrafiltration and stored at 4° C. in the dark until use. To determine the glucose response of GIP, the spectra of GIP were first characterized by scanning its emission and/or excitation wavelength using a luminescence spectrometer. The emission of the GIP showed two peaks: one at 510 nm and another at 527 nm when excited at 395 nm (curve a in FIG. 4A). The appearance of an emission peak at 527 nm indicates that some energy transfer occurs from the donor GFPuv to the acceptor YFP in the absence of glucose. The excitation spectra of GIP measured at the emission wavelength of 527 nm revealed three excitation peaks, that is, 395, 488, and 513 nm. It is known that both GFPuv and YFP have a small excitation spectrum peak at 488 nm. Excitation of GIP at 513 nm produced an emission peak at 527 nm (curve b in FIG. 4A), which is the typical emission peak of YFP when excited at 513 nm. This indicated that the fusion of GFPuv-GBP to the C-terminus of YFP does not change the fluorescence spectrum of YFP.

No emission of YFP-GBP could be detected when excited at 395 nm, although it had an emission peak at 527 nm when excited at 513 nm (FIG. 4B). Clearly, in the absence of glucose, the emission of GIP at 527 nm when excited at 395 nm is caused by fluorescence energy transfer. This result is consistent with the X-ray studies on the structure of the glucose binding protein, which reveals that it can adopt at least two different and stable conformations. The protein is able to adopt a closed form in the absence of ligand (glucose/galactose), which places the two terminal domains close to each other. The space between the two domains located in sites 15 and 152 (glucose binding pocket) of GBP shortens the distance between two fluorescent proteins located at N- and C-termini of GBP. On the other hand, the two domains can be relatively far apart in the presence of bound glucose, resulting in a reduction of the fluorescence intensity at 527 nm when excited at 395 nm.

Example 4

Binding Isotherm of GIP for Glucose

Figure 5:
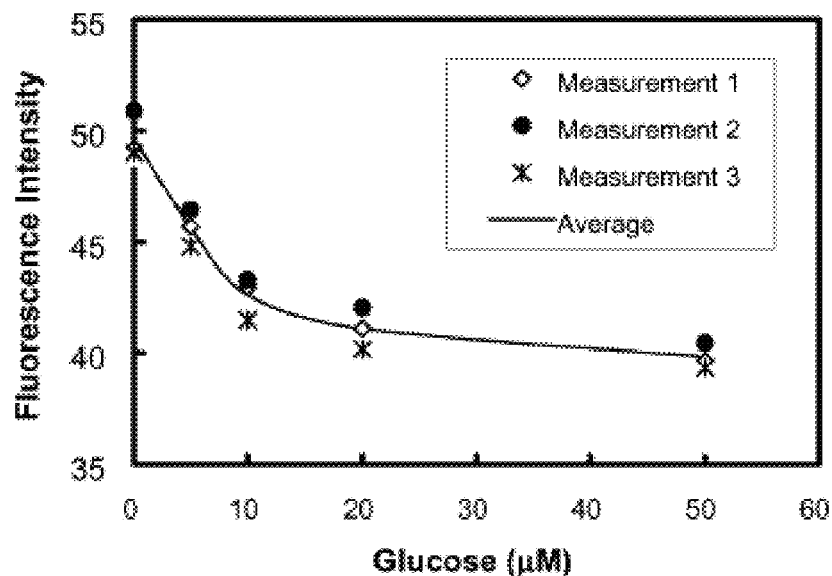
FIG. 5 depicts the glucose affinity to GIP. Data points shown are the average of three experiments. Highly concentrated glucose was diluted into a buffer containing GIP, and the fluorescence intensity of GIP was measured at 527 nm when excited at 395 nm. Slit width was 5 nm. All measurements were conducted at room temperature.

The binding affinity of GIP for glucose was determined by the fluorescence energy transfer method (FIG. 5). GIP was dissolved in the binding buffer and highly concentrated glucose was titrated into the solution. The total volume of the glucose added to the protein throughout the entire procedure was <5 ml. The conformational change induced by glucose binding was determined by measuring the fluorescence intensity of GIP using an excitation wavelength of 395 nm and an emission wavelength of 527 nm. A decrease in the fluorescence intensity from GIP was observed with the addition of glucose, indicating the reduction of FRET between GFPuv and YFP. Moreover, the decrease in fluorescence intensity was linearly related to glucose concentration up to 20 mM. The GIP binding site appeared to become saturated when the glucose concentration was raised above 20 mM, consistent with the reported binding affinity of GBP. Therefore, the apparent Km for GIP is ~5 mM.

Example 5

Glucose Microsensor using GIP

Figure 6:
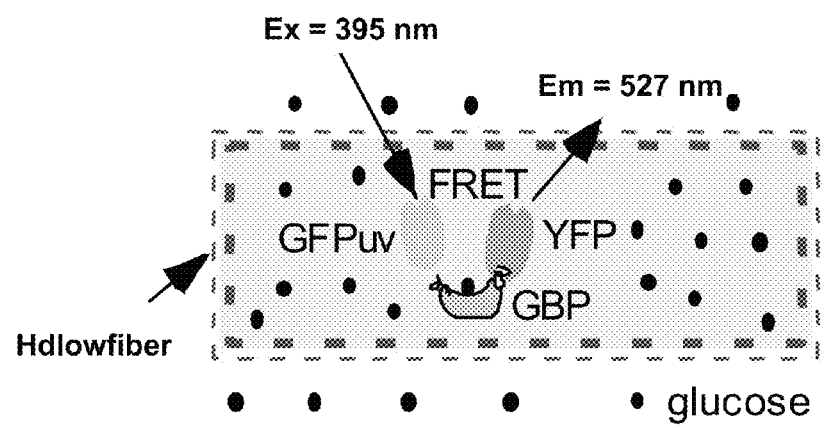
FIG. 6 depicts a representation of a follow-fiber glucose biosensor constructed with GIP in which a GFP-based FRET signal transduction function was integrated for sensing glucose. A dialysis hollow fiber made from regenerated cellulose was used for including the protein. It was cut into a small fragment 1.5 cm in length. The dialysis hollow fiber had a molecular weight cutoff of 10 Kda allowing small molecules such as glucose to pass through the hollow fiber, while retaining GIP, which has a molecular weight of 86 Kda.
Figure 7:
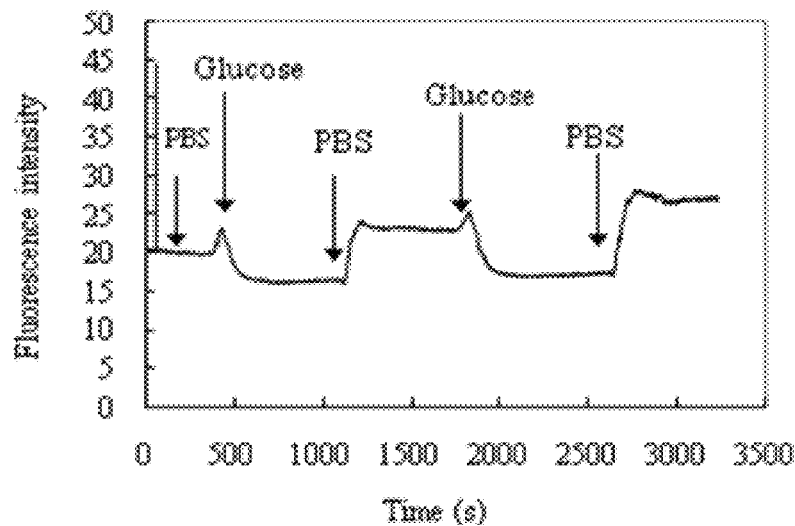
FIG. 7 depicts the response of a hollow fiber glucose biosensor constructed with GIP. Sugar-free PBS was used to provide a baseline for the sensor. Glucose (10 μM) was used in the experiment. The change of FRET was monitored by measuring the change in the fluorescence of GIP included in the hollow fiber. Excitation wavelength of 395 nm and emission wavelength of 527 nm were used. The data interval was 1 second. All experiments were carried out at room temperature.

Finally, a glucose microsensor using GIP was designed as shown in FIG. 6. In this prototype glucose biosensor, GIP was sealed into a dialysis hollow fiber that had an internal diameter of 190 mm, wall thickness of 20 mm, and cutoff molecular weight of 10 kDa. Thus, the protein is retained inside the hollow fiber but small molecules such as glucose can permeate through the dialysis fiber and reversibly bind to GIP, generating a conformational change-induced change in FRET. The hollow fiber microsensor was placed into a quartz cuvette that had an inner cylinder hole with a 7 ml sampling volume. The segment was fixed inside the cell by pushing it down with the inflow cover of the flow-through cell unit. The whole unit was then set up into a luminescence spectrometer. A sugar-free PBS buffer containing 1 mM $CaCl_2$ was gravity-perfused into the flowthrough unit and a baseline for the sensor was produced. A decrease in fluorescence intensity was observed the when the glucose (10 mM) solution flowed past the sensor, indicating the reduction of FRET between the two fluorescent proteins GFPuv and YFP (FIG. 7). Fluorescence intensity recovered when PBS buffer was circulated past the sensor, which removed the glucose (by dialysis) from the encapsulated GIP. The response time was ~100 s. Therefore, it can be concluded that the kinetics of binding and conformational change must be faster than 100 seconds because there are some delays in the exchange of the perfusing solution and the diffusional lag due to the barrier properties of the dialysis tube itself. As is apparent from the data in FIG. 7, the sensor response to glucose was fairly reproducible and reversible over this time period.

Example 6

Development of pH Insensitive GIP

Figure 8:
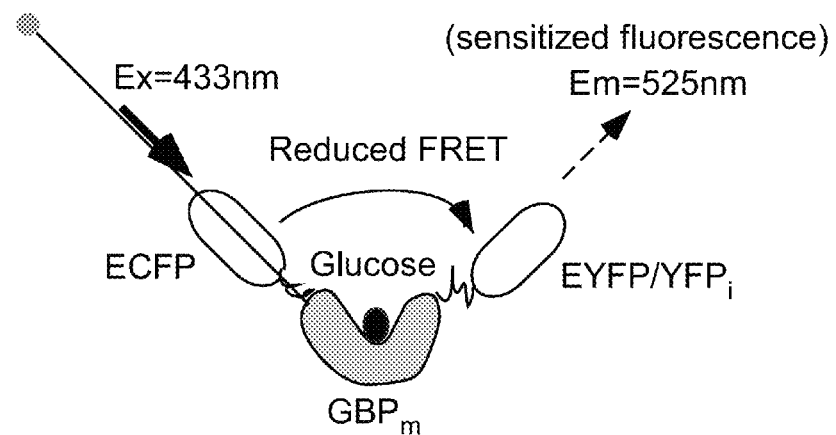
FIG. 8 depicts a schematic diagram of the GIP for continuous glucose monitoring. The GIP was constructed by flanking a mutated GBP (GBPm) with two fluorescent proteins. The GBPm changes its conformation upon binding glucose, leading to a change in distance between ECFP and EYFP or a pH insensitive YFPi. This glucose binding-induced distance change alters the FRET that can be quantitatively measured by detecting by the change in the intensity ratio of fluorescence emitted by both YFP and ECFP.

As it is evident from the data in FIG. 9A, measurement of glucose using the GIP constructed in Example 2 was sensitive to pH. To alleviate the pH effect on the conformational change-induced FRET upon the glucose binding to GIP, a pH insensitive GIP was constructed by replacing pH sensitive components of GIP with pH insensitive components. In this experiment, a mutant form of GBP (GBPm) where Phe 16 is replaced with Ala (See Example 7 below) was used. The $pK_d$ of GBPm was 589 mM for glucose and $pK_d$ of 848 mM for galactose. Thus the GIP constructed with this mutated glucose binding protein should be able to measure a glucose concentration up to 5 mM. GBPm was flanked at its N and C termini with an ECFP (enhanced cyan fluorescent protein), and a pH insensitive YFPi (yellow fluorescent protein), respectively (FIG. 8). The resulting GIP was designated $C_oY_i$. In a control construct, enhanced YFP (EYFP) was used instead of YFPi to produce the GIP refered to as $C_oY_o$.

Sensitivity of the resulting GIPs to pH was then tested in a glucose binding affinity test (FIG. 9). To establish a calibration curve of $C_oY_i$, the highly concentrated glucose was added directly to the protein solution and the change of fluorescence intensity ratios of YFPi over ECFP was measured. This experiment indicates that 10 min was sufficient for glucose binding to the GIPs as the fluorescence intensity ratio tended to be stable after 10 min incubation at room temperature (data not shown). These observations are consistent with our previous studies on the glucose binding to GIPs. As previously reported, the conformational change-induced FRET can be determined by fitting the substrate titration curves to the equation for the binding of a ligand to a protein.

$$\frac{R_{max} - R}{R_{max} - R_{min\square}} = \frac{n[S]^n}{K_d + [S]^n} \quad (1)$$

where [S] is the glucose concentration, Kd is the apparent dissociation constant that corresponds to a glucose concentration yielding an R (fluorescent intensity ratio of YFP to ECFP) midway between $R_{max}$ and $R_{min}$, n is the Hill coefficient. The $(R_{max}-R)/(R_{max}-R_{min})$ is defined as a saturation of the FRET. As shown in FIG. 9A, the glucose titration curve of the pH sensitive $C_oY_o$ at pH=6.2 was almost the same as that determined at pH=7.3. Nevertheless, the response of $C_oY_o$ to glucose fluctuated wildly when pH dropped to 5.2 due to the instability of EYFP under an acidic environment. In contrast, $C_oY_i$ exhibited high stability under an acidic environment. No significant deviation in the glucose titration curves was found when exposing the $C_oY_i$ to an acidic environment. The glucose titration curves of $C_oY_i$ obtained at pH=7.3, 6.2, and 5.3 were almost the same, showing much improvement in reporting a quantitatable and consistent glucose measurement in a varying pH environment. Therefore, $C_oY_i$ is an ideal GIP for intracellular glucose studies where the pH values could vary significantly.

By using a pH-stable YFP to construct the glucose indicator $C_oY_i$, we were able to show that the $C_oY_i$ was more tolerant to the acidic environment. The resulting conclusion from this work is that a pH-insensitive glucose indicating protein can be engineered through flanking a glucose binding protein with pH insensitive fluorescent proteins such as YFPi used in this work. This protein allows for the quantitation of glucose concentration despite a changing pH environment. The conception and production of a pH-insensitive GIP is a great tool for use in varying pH environments. An exemplary application is the measurement of intracellular glucose. The use of this GIP as a noninvasive glucose measurement instrument will work well as interstitial glucose levels tend to follow blood glucose concentrations within a 3 to 5 minute time frame.

Example 7

Construction of an Array of GIPs with the Ability of Sensing a Wide Range of Glucose Concentrations Wild-type GBP has phenylalanine at the 16th amino acid residue and has a carbohydrate ligand binding pocket. Crystallographic analysis of wild-type GBP reveals that the D-glucose/D-galactose is sandwiched in the GBP binding pocket by facing Phe16 and Trp183 of GBP through extensive van der Waals interactions, indicating the super-positioning effect of the 16th and 183th amino acid in the sugar binding site. In an attempt to alter the affinity of GBP and to improve the glucose monitoring range of GIPs constructed with GBP for real-time glucose detection, the effect of point mutation at the 16th amino acid residue of the GBP on its glucose binding affinity was examined. In brief, Phe16 of GBP in $C_oY_i$ constructed in Example 6 was replaced with either valine, cysteine, threonine, or leucine through site-directed mutagenesis. The resultant GIPs were designated as GIP$_i$-Val, GIP$_i$-Cys, GIP$_i$-Thr, GIP$_i$-Leu and GIP$_i$-Ala. A protein variant with a single amino acid deletion of the 16th amino acid of GBP was constructed and assigned as GIPi-Null for control measurements. Similar point mutations, in addition to a Phe16 to Leu substitution, were also made to the original GIP constructed in Example 2.

Figure 10:
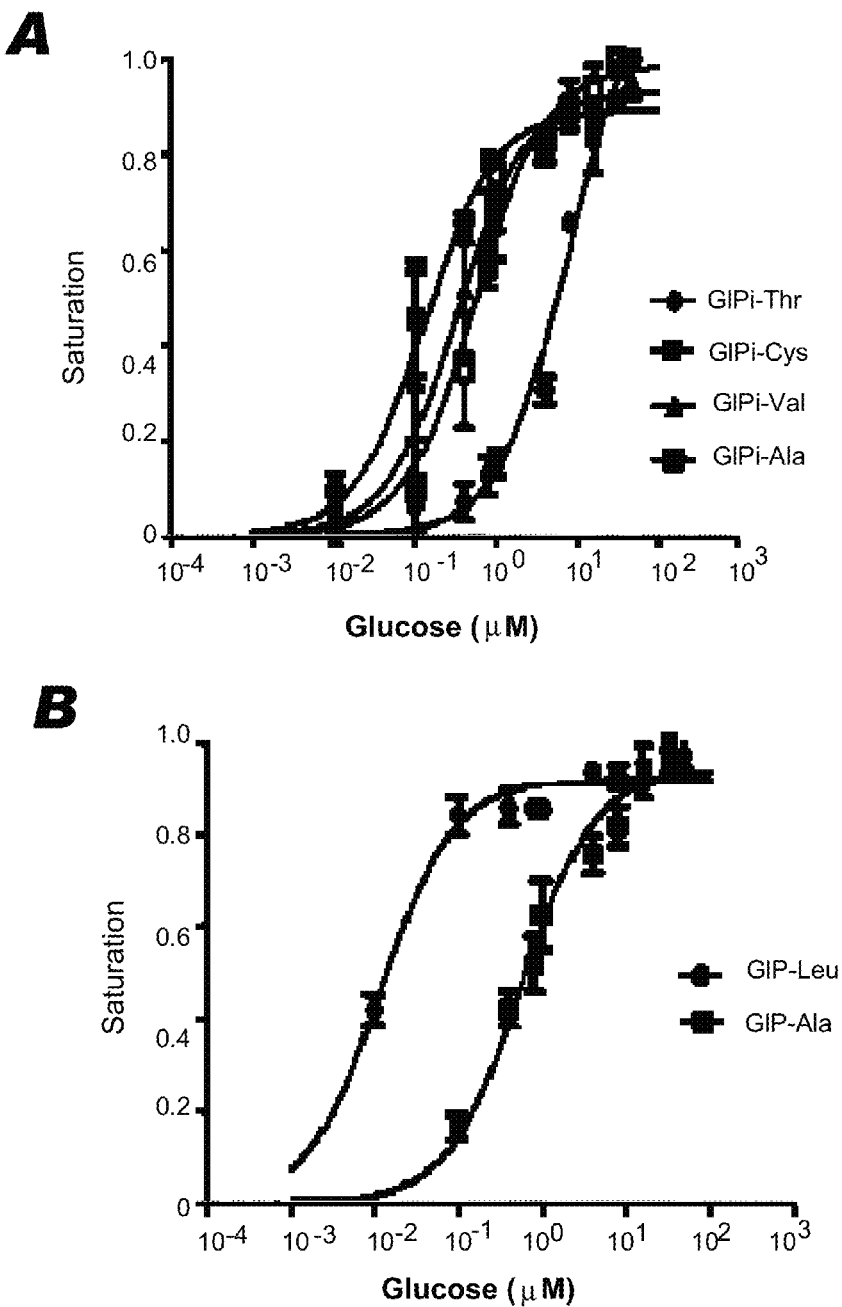
FIGS. 10 (A) and (B) depict non-linear regression on glucose curves of mutated GIP: (A) $GIP_i$-Thr, $GIP_i$-Cys, $GIP_i$-Val and $GIP_i$-Ala; (B) GIP-Leu and GIP-Ala. Data shown are the mean values of three experiments and error bars represent the standard deviation.

Titration of the purified GIPs presented a glucose dose-dependent decrease in FRET (FIG. 10). The binding affinities of mutated GIP were determined using non-linear regression and the properties of mutated GIP nanosensors were listed in Table B. The binding affinities of GIP$_i$-Cys and GIP$_i$-Val were 0.13 mM and 0.33 mM, respectively, which decreased the affinity of the sensor for glucose as compared with wild-type phe16 of GBP. The threonine substitution had an affinity of 7.9 mM, and therefore, a greatly decreased binding affinity for glucose. As two references, the binding affinities of GIPi-Ala and GIP-Leu were determined as 0.554 mM and 0.605 mM, respectively. For GIPi-Thr, where threonine substitutes the Phe at amino acid position 16, the glucose sensing range is spanned from 1 mM to 32 mM (FIG. 10A). The substitution of cysteine and valine manages the glucose sensing range from the 0.01 mM to 0.8 mM, and the 0.01 mM to 1.0 mM, respectively. Leucine mutation from phenylalanine presented 5-fold increase of Kd value with sensing range from 0.004 mM to 0.4 mM. It is worth to note that the average value of maximum number of binding sites was calculated as 0.984, indicating the one-site specific binding (Table B).

TABLE B

Binding properties of the glucose nanosensors [a]

| Nanosensor | $K_d$ (mM) for glucose [b] | Std. Error of the mean | $R^2$ |
|---|---|---|---|
| GIPi-Cys | 0.131 | 0.026 | 0.920 |
| GIPi-Thr | 7.859 | 1.612 | 0.927 |
| GIPi-Val | 0.331 | 0.085 | 0.846 |
| GIPi-Ala | 0.554 | 0.084 | 0.942 |
| GIP-Leu | 0.026 | 0.005 | 0.973 |
| GIP-Ala | 0.605 | 0.077 | 0.959 |

[a] Determinations are averages of data collected from three measurments.
[b] Calculation of the binding affinity was performed using steady-state intensity data fit to one-site saturation binding isotherm with non-linear regression.

Example 8

Specificity of GBP Mutants to Glucose

Figure 11A:
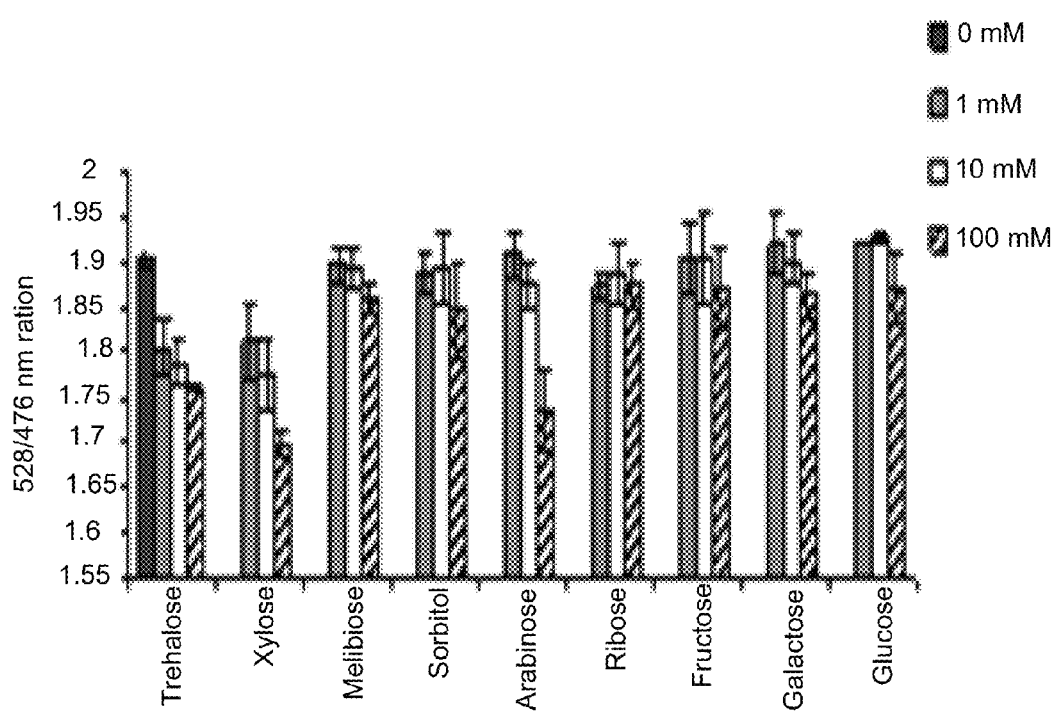
FIG. 11 depicts experiments showing that mutated GIPs retain specificity for glucose and galactose. Purified GIP-Ala (A), $GIP_i$-Cys (B), and $GIP_i$-Thr (C) were incubated for 10 min in solutions containing three concentrations of various substrates. The ratio of emission intensity at 526 nm and 476 nm are plotted for each substrate tested. The data shown are the mean of three experiments and the error bars represent standard deviations.
Figure 11B:
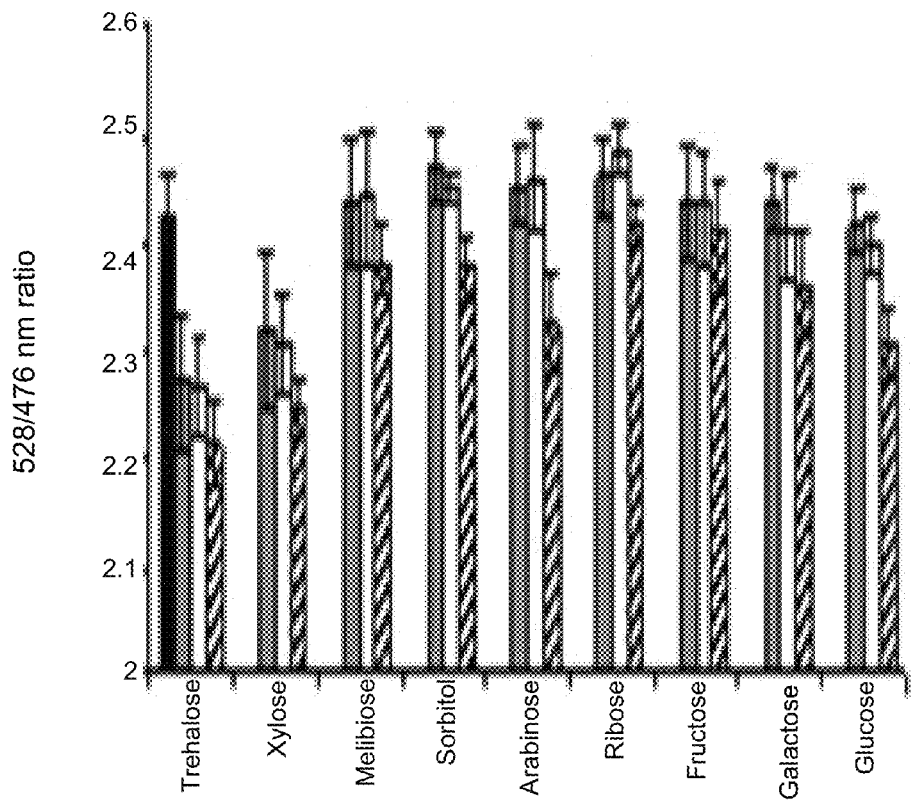
Figure 11C:
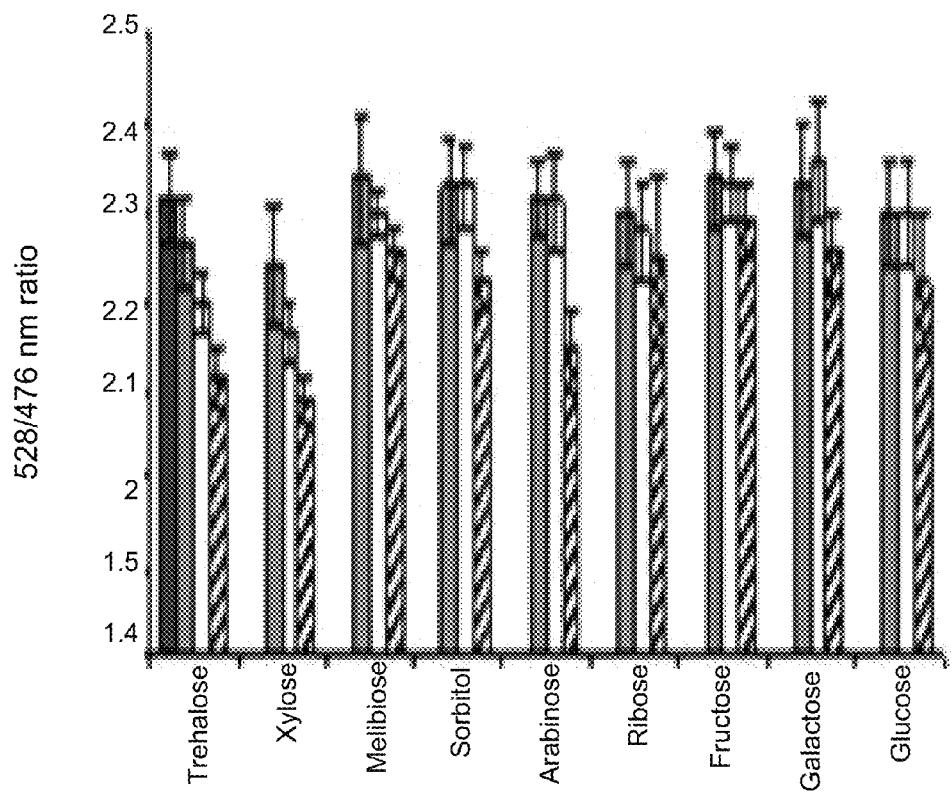

Monitoring glucose concentrations in living cells requires sensors possessing a high specificity to glucose. Thus it was next investigated whether the mutations of GBP described in Example 7 would lead to binding other carbohydrates. To assess specificity of the mutated GIP biosensors for glucose, a panel of related sugars was used to examine the specificity of the mutated GIPs. Proteins were purified from *E. coli* and analyzed for binding to galactose, fructose, ribose, arabinose, sorbitol, melibiose, xylose, and trehalose, and compared with binding of glucose by measuring the ratio of emission intensity at 526 nm and 476 nm. The GIP$_i$ mutants demonstrated the exact same specificity for all the sugars tested as compared with GIP-Ala (FIG. 11). As shown in FIGS. 11B and C, when incubated with 1 mM and 10 mM substrates, GIP$_i$-Cys and GIPi-Thr mutants exhibited response to the changes of glucose and galactose concentrations. The specificity of GIP-Ala in which the 16th amino acid of GBP is alanine was shown for comparison (FIG. 11A). None of the other substrates caused significant ratio changes at 1 mM and 10 mM concentrations. Although 100 mM of arabinose, trehalose, xylose, and ribose resulted in slight decreased ratios, 100 mM is far beyond physiological concentration for living cell monitoring. Thus, GIP$_i$ mutants remain high sugar selectivity for glucose and are appropriate for monitoring glucose concentration in vivo.

Example 9

Figure 12A:
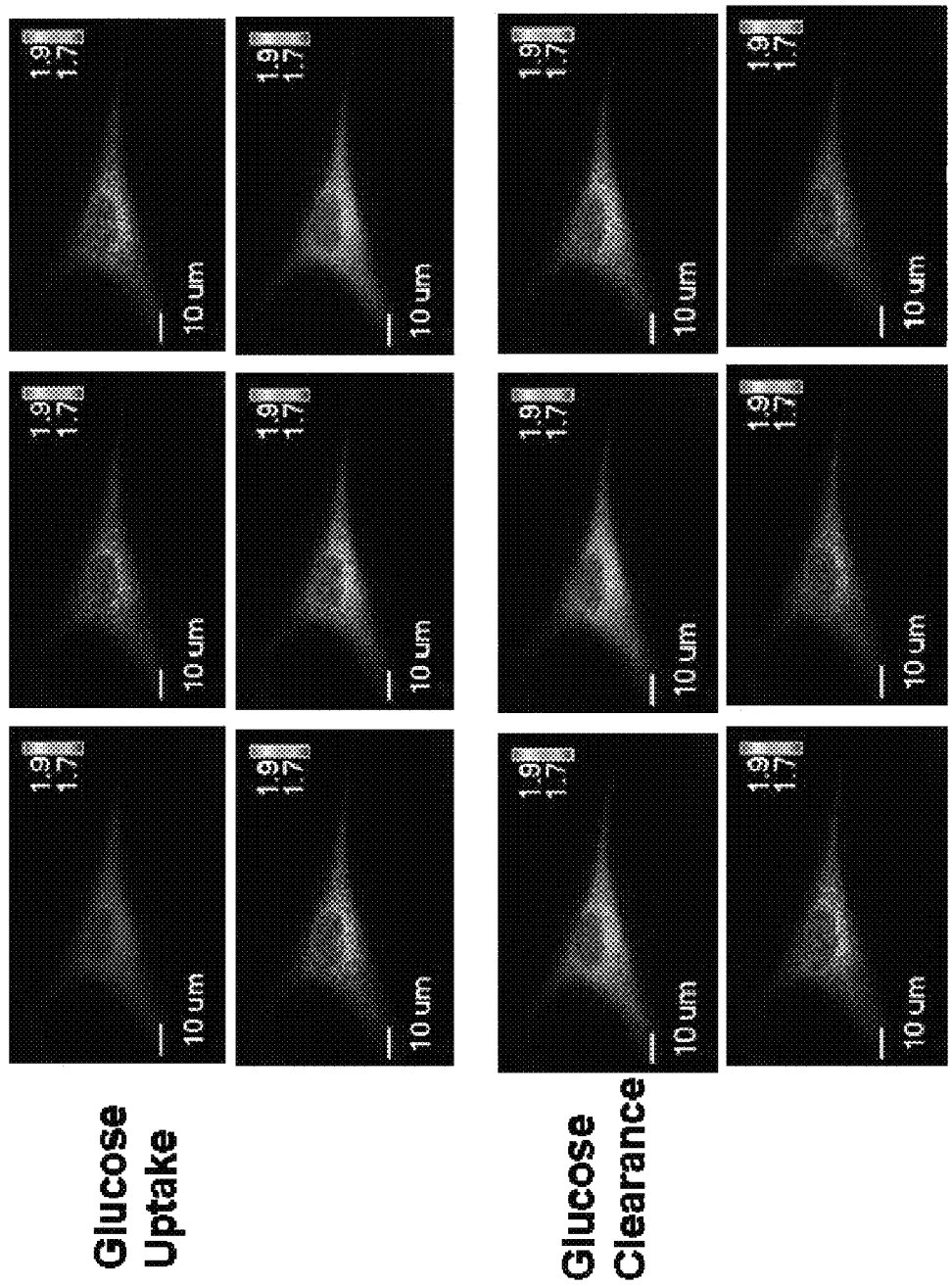
FIG. 12 depicts glucose-induced FRET changes in C2C12 cells expressing GIP. (A) Pseudo-color images of the FRET ratio in a cell expressing GIP. Red color indicates high FRET and low glucose concentration, and green color indicates low FRET and high glucose concentration. (B) Alternating FRET ratio values during glucose addition and removal illustrating the stability and repeatability of the sensor inside the celluler environment. The FRET ratio was measured at six second intervals during the perfusion of bath solutions containing 10 mM glucose or no glucose.

Visualization of Intracellular Glucose through FRET Microscopy Imaging Measurement with GIP To demonstrate the suitability of the GIP for visualizing the glucose within living cells, myoblast C2C12 cells were transfected with a plasmid that encodes the GIP. Pseudo color images of the cells were generated by the Slidebook software using 2-channel corrected FRET module based on the pixel-by-pixel intensity captured by the camera. The FRET intensity ratio was measured at six second intervals during the perfusion of bath solutions containing 10 mM glucose or no glucose. The images in FIG. 12A were captured with 200 ms exposure and 2×2 binning in a single live C2C12 cell. It was observed that the sensor protein was expressed in the cytosol with uniform distribution (FIG. 12A). The series of pseudo color images in the top panel of FIG. 12A indicate glucose uptake by the cells by the gradual reduction in the FRET ratio values. When the ratios were stabilized, the reversibility of the FRET sensor protein was tested by perfusion of the bath solution, in which glucose was replaced with 10 mM N-methyl-d-glucamine. As shown in the lower panel of the images in FIG. 12A, the intensity ratio returned closer to the original value due to the clearance of intracellular glucose.

Figure 12B:
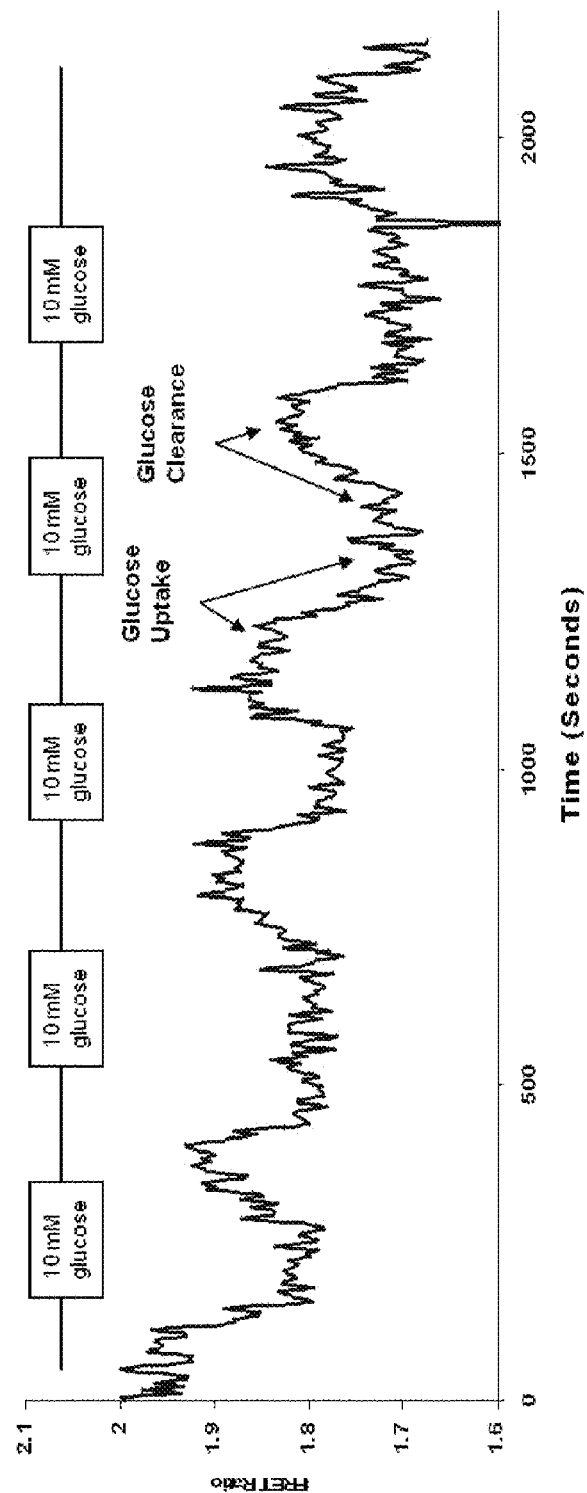

Following the addition of external glucose to the cells by perfusion with 10 mM glucose bath, the FRET ratio decreased from 2.0 to 1.8 in the company of the uptake of the glucose by living cells (FIG. 12B). The FRET ratio increased with the perfusion of glucose-free medium. The reversible ratio changes during the repeated on-off of extracellular glucose supplement demonstrated that the glucose indicator sensor is functional in vivo. The time constants for the glucose uptake and clearance were calculated as 31 and 101 seconds respectively by first order exponential curve fitting (data not shown) and the change in FRET ratio was about 0.2 in C2C12 cells under the culture conditions. We also observed the progressive decrease of the FRET ratio baseline from 2.0 to approximately 1.67 with the repeated switch of 10 mM glucose bath to glucose-free bath solution (FIG. 12B). The phenomenon is consistent with previous studies, which illustrated that even when the extracellular glucose was removed completely by perfusion, intracellular glucose concentration could not be returned to its original level because non-sugar substrates or glycogen were stimulated by the removal of extracellular glucose.

Example 10

Figure 13A:
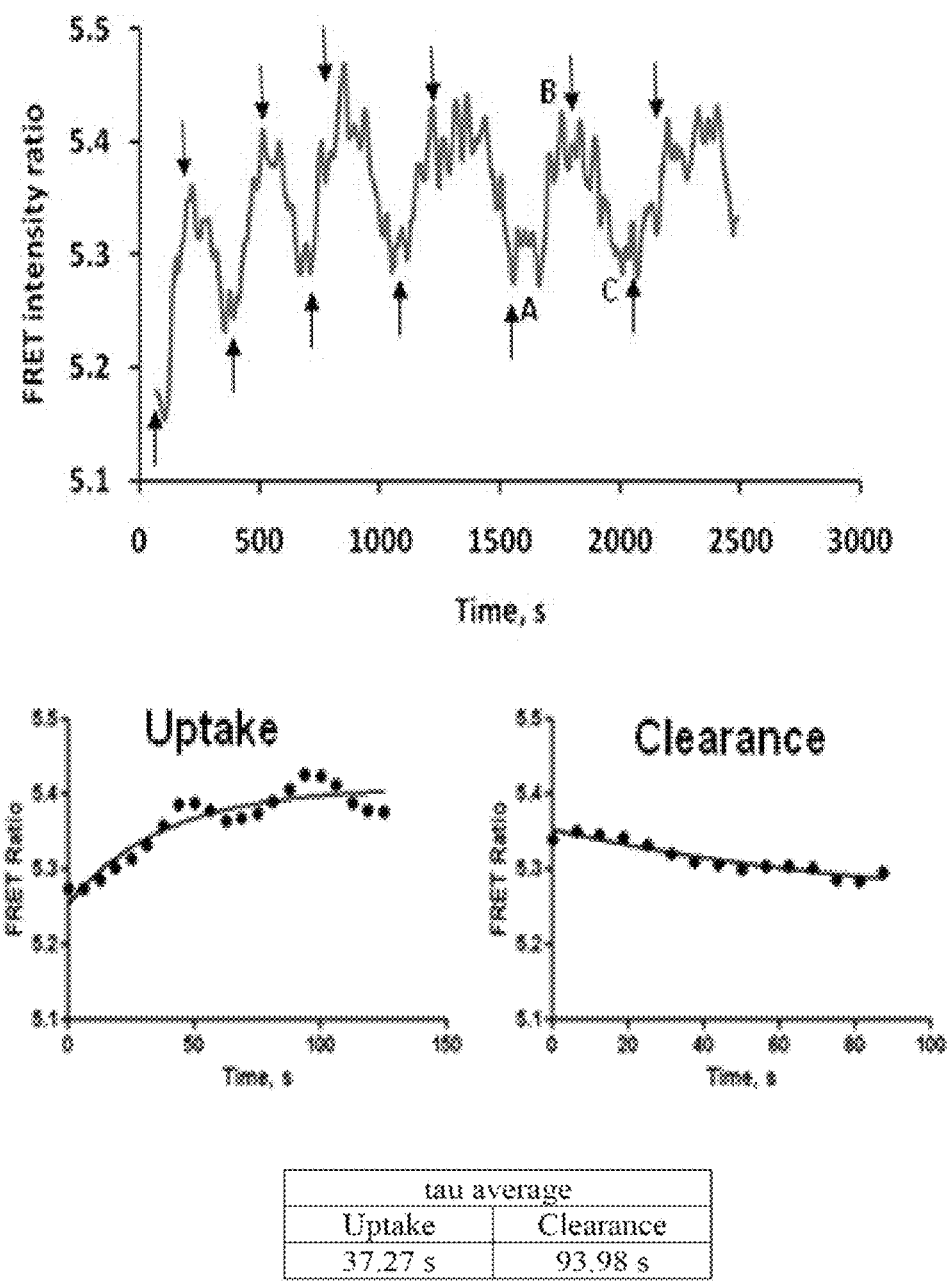
FIG. 13 depicts measurements and visualization of glucose within living cells through fluorescence lifetime microscopy imaging. (A) Time-lapse Intracellular glucose response imaged in C2C12 cells using AcGFP-GBPval-mCherry protein sensor. Upward arrows indicate external glucose addition (intracellular uptake) and downward arrows indicate the clearance of glucose from the cells. (B) Representative pseudocolor FRET ratio images (selected between time point A and B indicated in the image) from an individual C2C12 cell showing the increase intracellular glucose concentration. Typical glucose uptake and clearance curves were fitted to first order exponential and the time constant (tau) values were calculated.
Figure 13B:
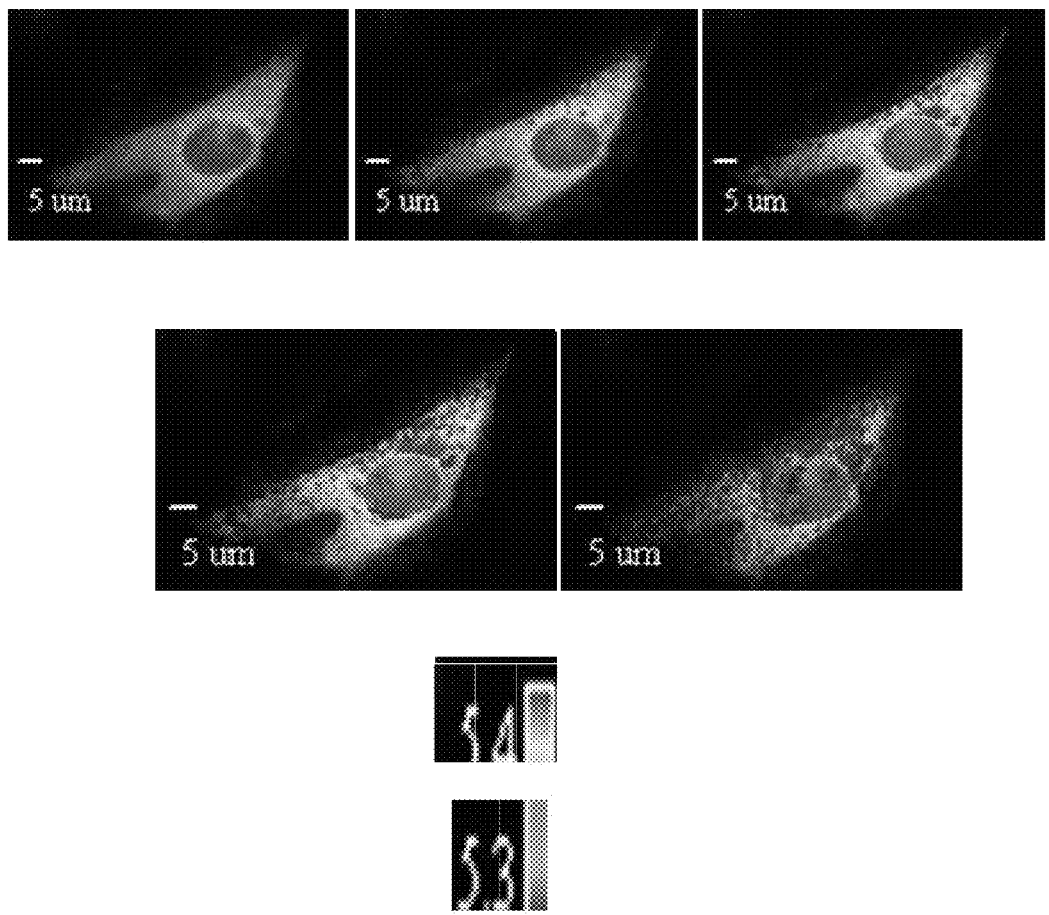

Visualization of Glucose Concentration within Living Cells Using AcGFP-GBPval-mCherry GIP A GIP comprising the GBPval mutant GBP, AcGFP as the fluorescence donor, and mCherry as the fluorescence donor was constructed. The AcGFP-GBPval-mCherry protein biosensor was transiently expressed in C2C12 cells. The cells were perfused with 10 mM glucose bath solution or a wash buffer through a Focht Chamber System-2 (FCS-2) micro-observation flow chamber (Bioptechs Inc, Bulter, Pa.). The chamber volume was 0.330 ml and the flow rate was maintained at 1.2-1.5 ml/min. FRET intensity images were captured using a 12-bit Rolera fast CCD camera (Q-imaging Inc. surrey, Canada). To control the camera and filterwheels as well as to analyze the images, Slidebook Imaging Software (Intelligent Imaging Innovations Inc., Denver, Colo.) was used. As shown in FIG. 13 in the C2C12 mouse myoblast cell line, this GIP can provide a stable base line.

Example 11

Figure 14C:
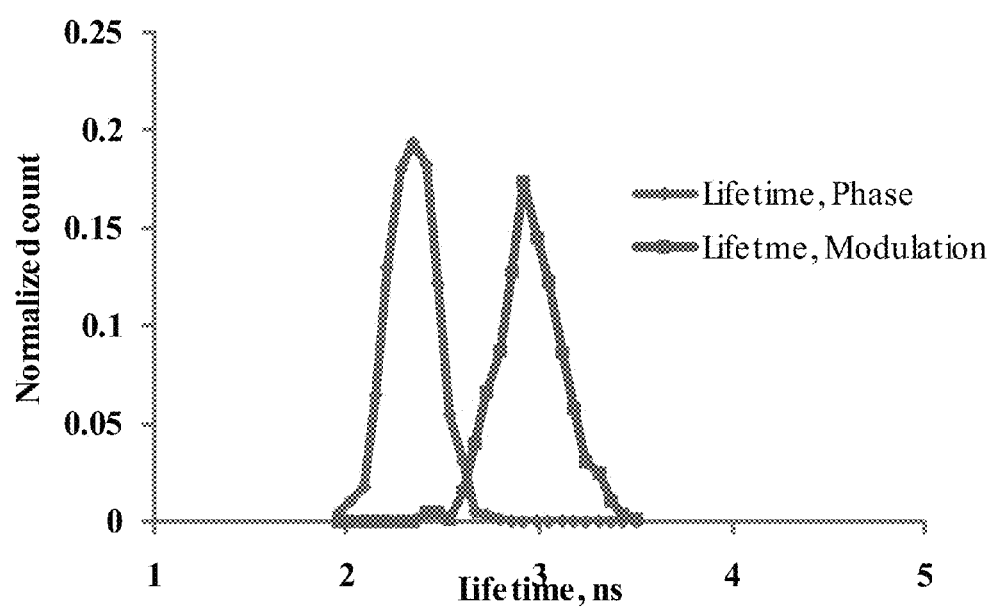
FIG. 14 depicts the determination of lifetime of GIP in transfected murine myoblast C2C12 cells. (A) Phase contrast micrograph and (B) fluorescence lifetime microscopy image of C2C12 cells transfected with GIPval. The images were taken 48 h post transfection. (C) Phase and modulation lifetimes of ECFP.
Figure 15C:
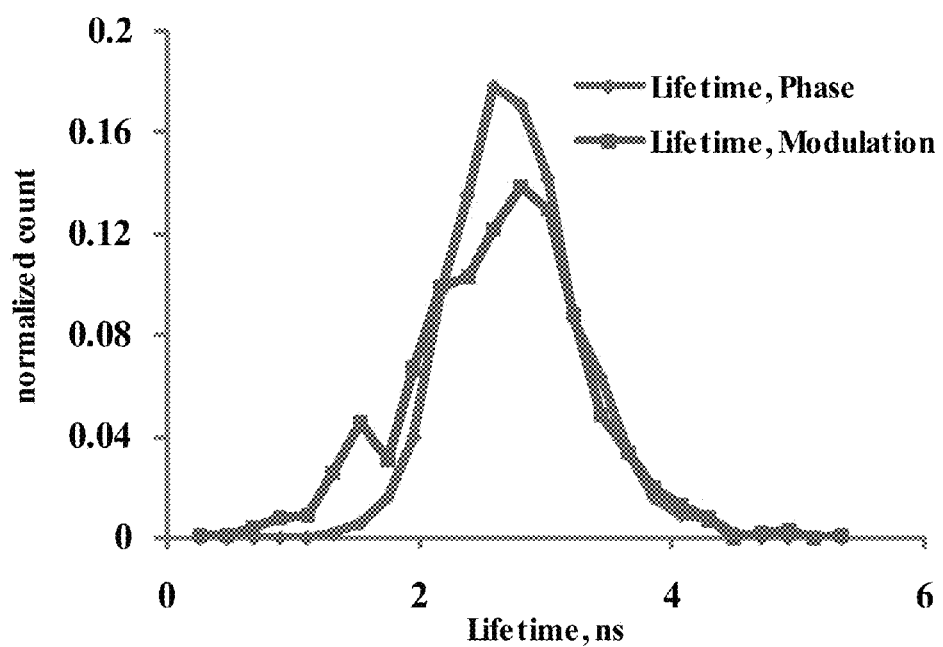
FIG. 15 depicts the determination of phase and modulation lifetime of AcGFP in living cells. (A) A phase contrast micrograph and (B) fluorescence lifetime microscopy image of pcDNA3.1-AcGFP-GBPval-mCherry transfected C2C12 cells. (C) phase and modulation lifetime of AcGFP.

Visualization of Glucose within Living Cells Through Fluorescence Lifetime Microscopy Imaging (FLIM) Measurement In frequency domain, lifetime can be determined from either the phase shift or change in modulation of the fluorescence. If the lifetime in phase and modulation is identical, the fluorescence is considered mono-exponential. It has been determined that ECFP is multi-exponential (FIG. 14). The multi-exponential nature of ECFP makes GIP comprising a FRET pair of ECFP and EYFP difficult to use in the FLIM measurement. To circumvent this drawback, a new type of GIP was designed using AcGFP as a donor flurophore, and mCherry as an acceptor fluorophore. We first determined whether the AcGFP is mono-exponential using a frequency-domain FLIM system (FIG. 15). Murine myoblast cells C2C12 were transiently transfected with a GIP expression plasmid pcDNA3.1-AcGFP-GBPval-mCherry. The FLIM images were performed 48 h post transfection. The phase and modulation lifetime of AcGFP were identical. The average phase or modulation lifetime was 2.6-2.7 ns; hence, the AcGFP expressed in C2C12 cells is mono-exponential in nature.

In addition, although AcGFP was somewhat prone to photobleaching (FIG. 16A), the lifetime remained relatively constant (FIG. 16B). Also, the perfusion of glucose did not affect the lifetime measurement.

Example 12

Determining Glucose Concentration Through FLIM Measurement of GIPs

Figure 16:
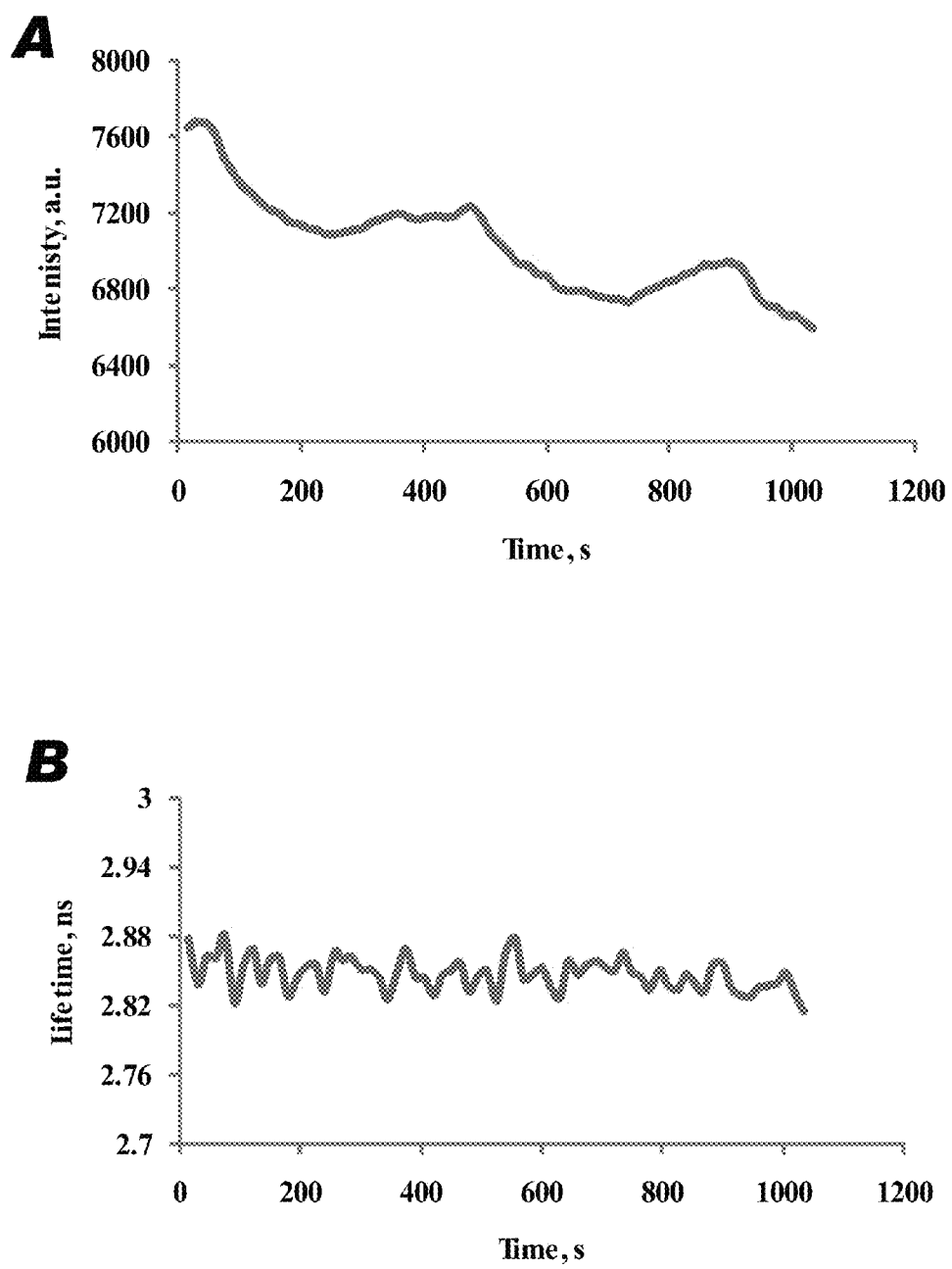
FIG. 16 depicts the determination of photo bleaching of AcGFP in transfected C2C12 cells. (A) Photo bleaching of AcGFP during the fluorescence lifetime microscopy measurement and (B) time course of lifetime of AcGFP during fluorescence lifetime microscopy imaging.
Figure 17:
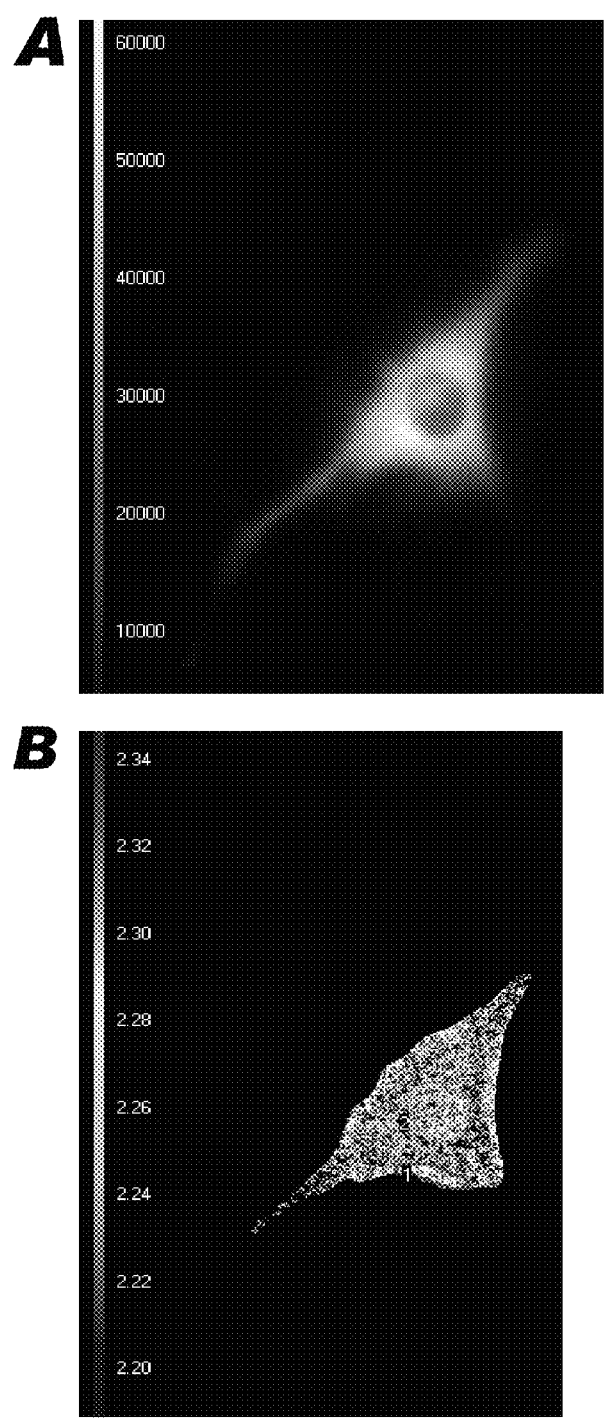
FIG. 17 depicts C2C12 cells expressing GIP imaged in presence of 20 mM extracellular glucose. (A) Fluorescence intensity image and (B) a pseudo colored lifetime image. (C) The average lifetime intensity for two ROIs. (D) The total fluorescence intensity and donor lifetime for two ROIs.
Figure 17:
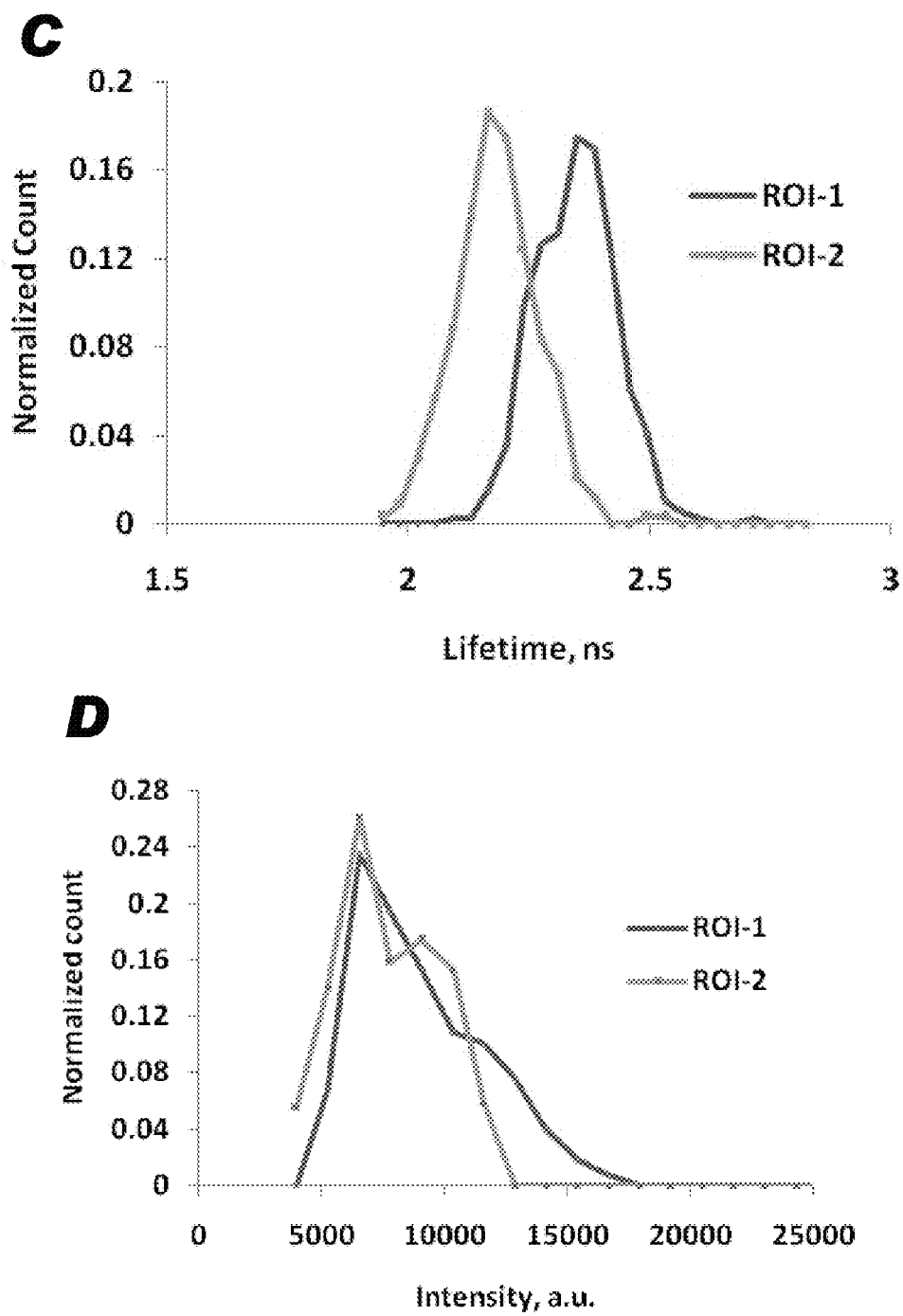

C2C12 cells were transfected with an AcGFP-GBPval-mCherry expression plasmid and two measurements were collected using FRET-FLIM 48 h post transfection; one in the cell periphery, and another around the nucleus (FIG. 16). The average total intensity for these ROIs was almost identical (FIG. 16D), whereas the average lifetime was clearly distinguishable (2.18 ns for ROI-2 and 2.34 ns for ROI-1) (FIG. 16C). Thus, the fluorescence lifetime microscopy imaging can more accurately differentiate the local glucose concentration in different cellular compartments.

Example 13

Fluorescence Lifetime Monitoring using AcGFP-GBPcys-mCherry

Figure 18:
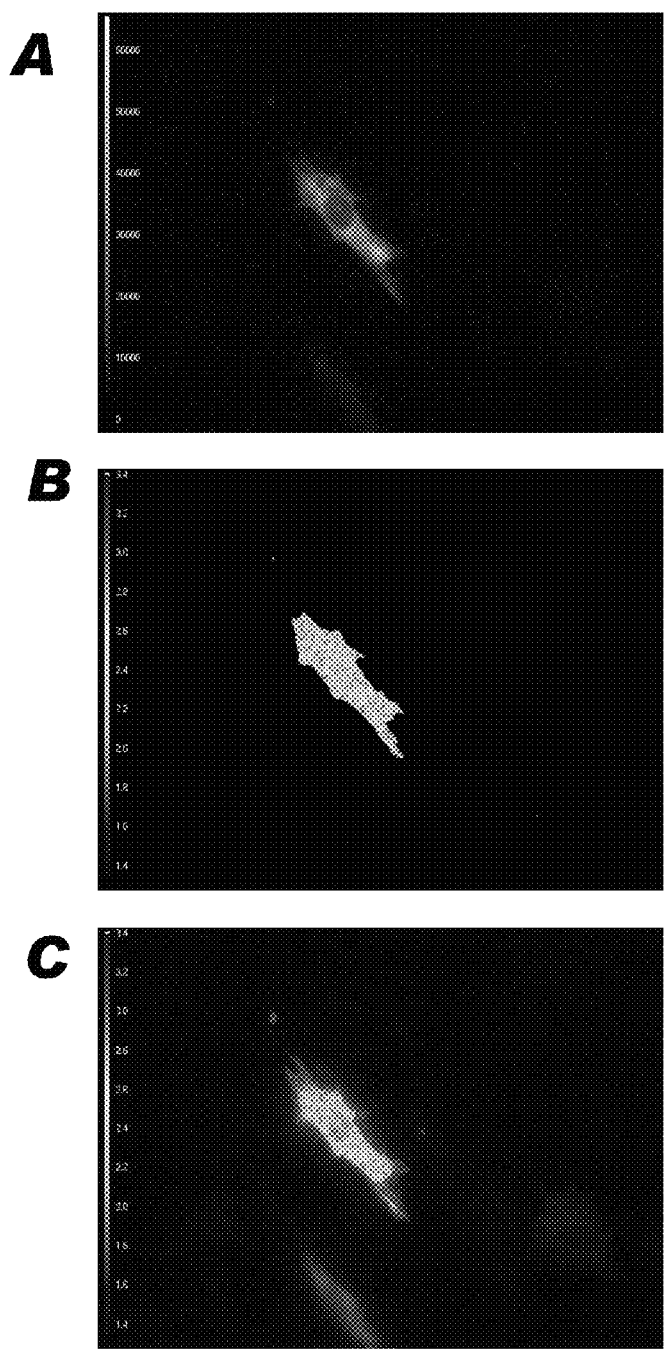
FIG. 18 depicts C2C12 cells showing the expression of (A) AcGFP-GBPcys-mCherry. (B) A typical fluorescent lifetime map of the cell, which is merged with (C) fluorescent intensity image are also shown.
Figure 19:
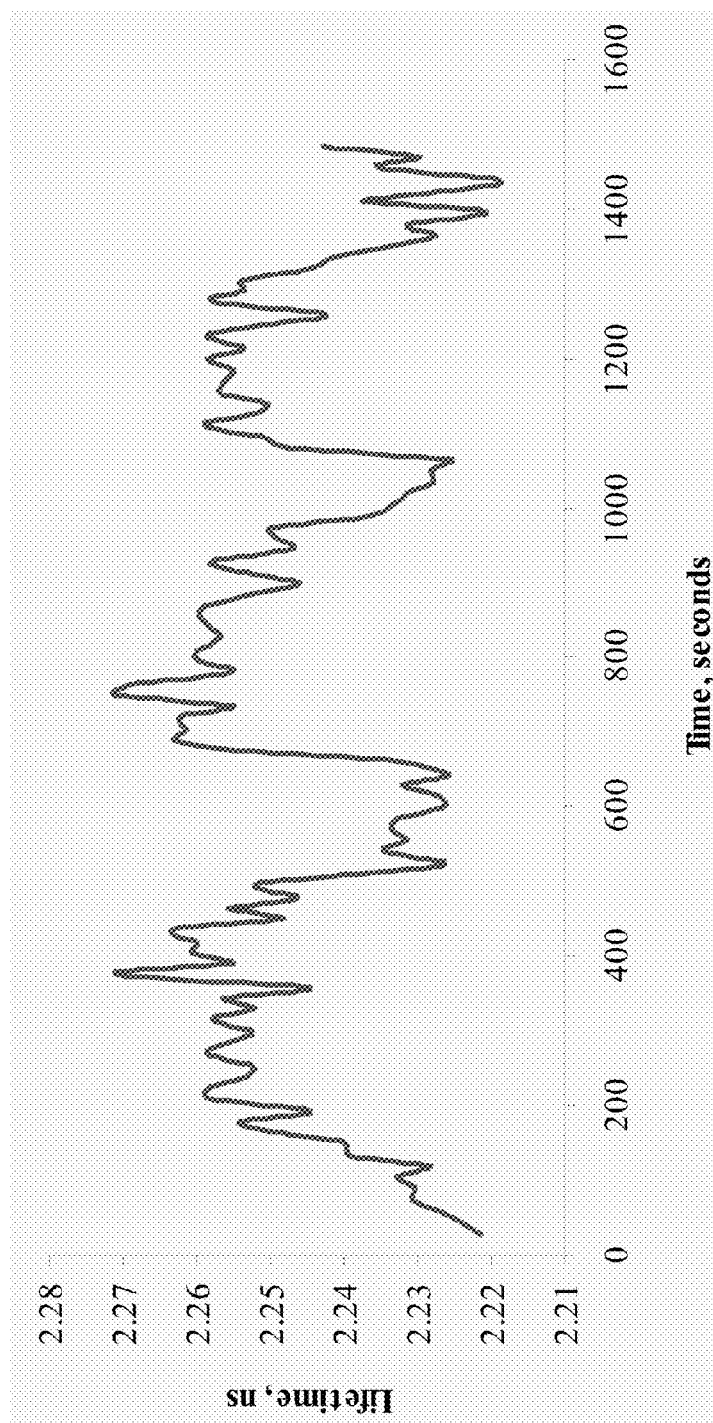
FIG. 19 depicts raw data from the frequency domain lifetime imaging system for the cell showed in FIG. 18.

The GIPs comprising AcGFP also allow continuous glucose monitoring using live cell FLIM (FIG. 18). When extracellular glucose (10 mM) is added to cells expressing AcGFP-GBPcys-mCherry, the lifetime is increased by about 35 ps, and thereafter stabilized at the lower value (FIG. 19). Upon flushing the extracellular glucose with a bath solution (glucose is replaced by equal concentration of analogue to maintain the osmolarity), the lifetime regained the initial value, and stabilized thereafter. Experiments were performed in multiple batches, and various cells from each batch were monitored for glucose response The rate of glucose uptake was determined from the time points and corresponding lifetime values between the addition of extracellular glucose and the lower most lifetime value at which the response was stabilized (FIG. 20). The data points were fitted to first order exponential nonlinear regression. The Tau value is the time constant, expressed in the same units as the X axis. It is computed as the reciprocal of K, rate constant, expressed in reciprocal of the X axis time units. Hence either K or Tau characterizes the reaction rate or binding and dissociation rates. In these experiments, the Tau values were about 45 seconds.

Figure 21:
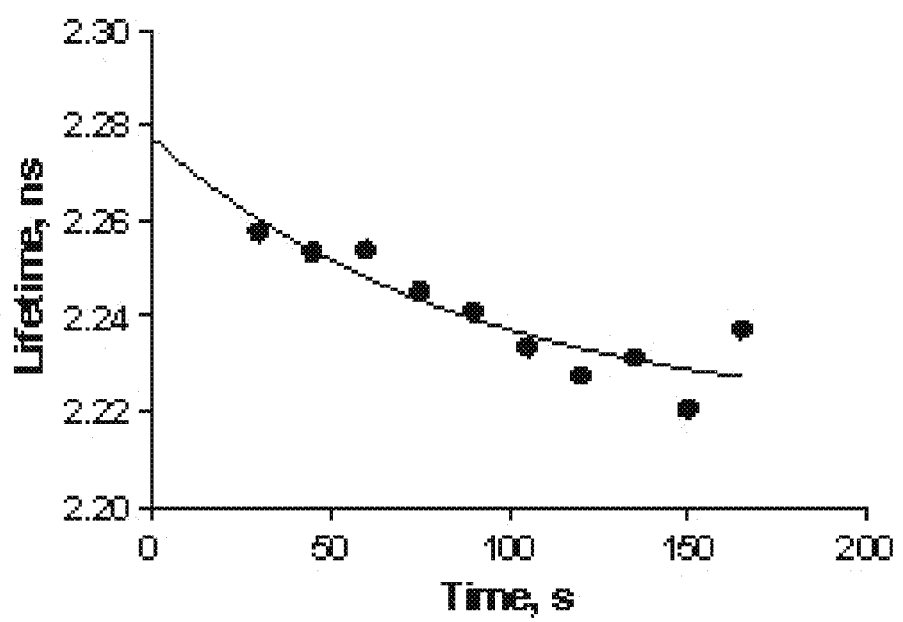
FIG. 21 depicts the clearance of glucose.

Similarly, glucose clearance was also fitted by first order exponential non-linear regression, revealing a relatively high Tau of 88.6 seconds, and revealing a slower rate of glucose clearance from the C2C12 cells (FIG. 21). The fit could not be made for the other clearance segments of the response curve without omitting some of the time points, probably because of the higher noise levels in the signal.

Figure 22:
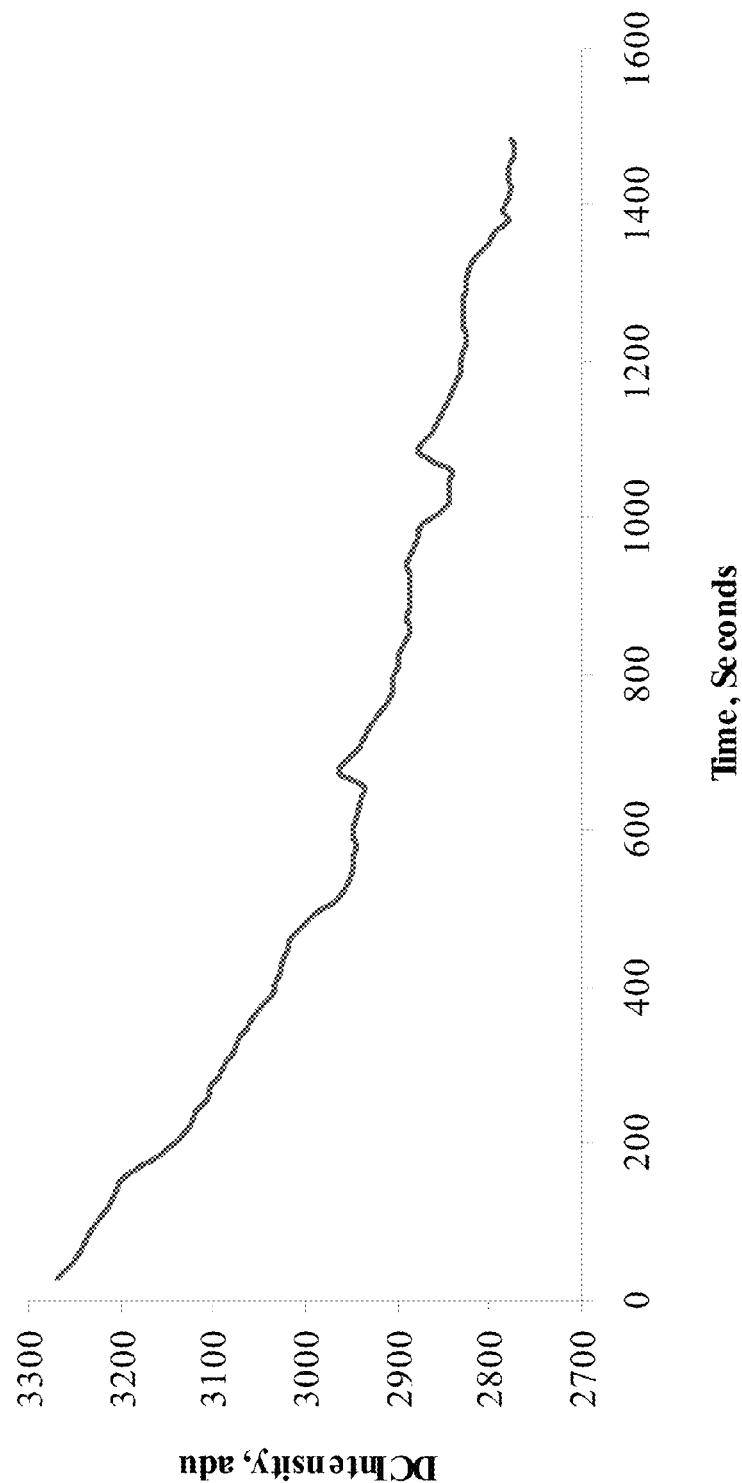
FIG. 22 depicts the change in fluorescence intensity in the area of the cell selected for the glucose monitoring.

The total intensity from the cell gradually decreased during the time lapse measurement (FIG. 22). This reduction was estimated to be about 15%. However, the change in intensity did not contribute to erratic patterns in the lifetime measurements. This is one of the major advantages of employing the lifetime measurement system for continuous live cell imaging.

Example 14

Glucose Response in C2C12 Cells Grown at Physiological Glucose Concentration

Figure 23:
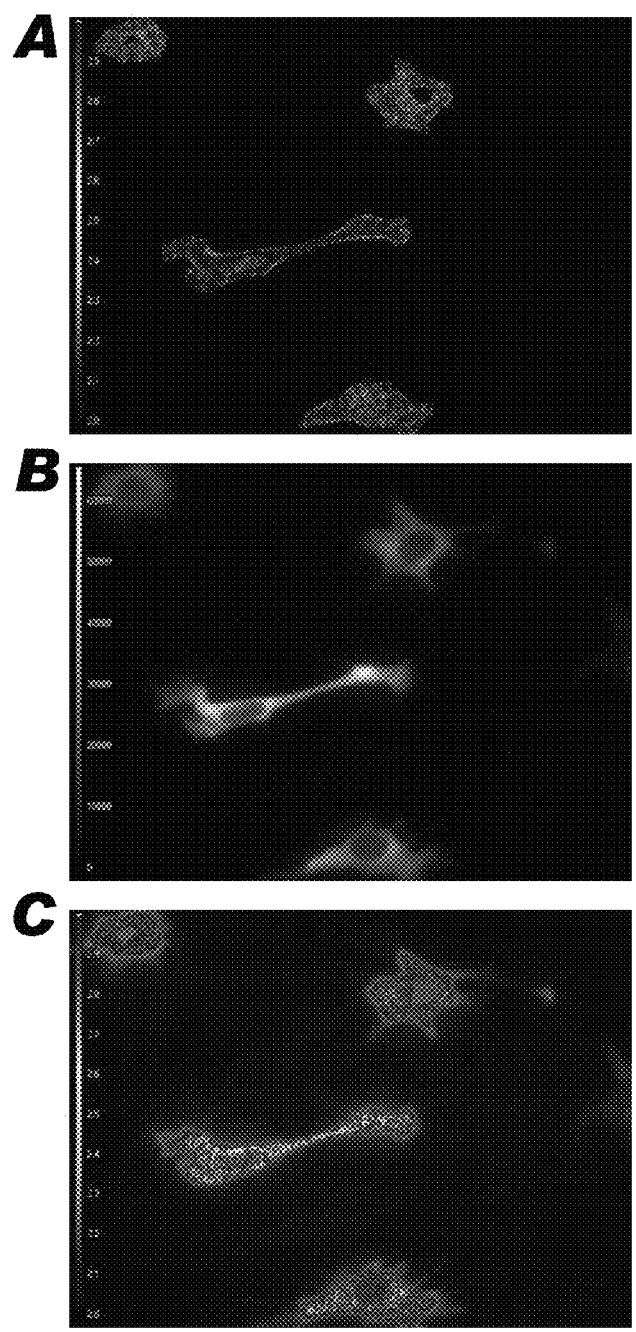
FIG. 23 C2C12 cells grown under physiological glucose concentration visualized with GIP. (A) Phase contrast micrograph, (B) FRET-FLIM image, and (C) overlapped cellular images of GIP expression plasmids transfected C2C12 cells. The images were taken 48 h post transfection.
Figure 24:
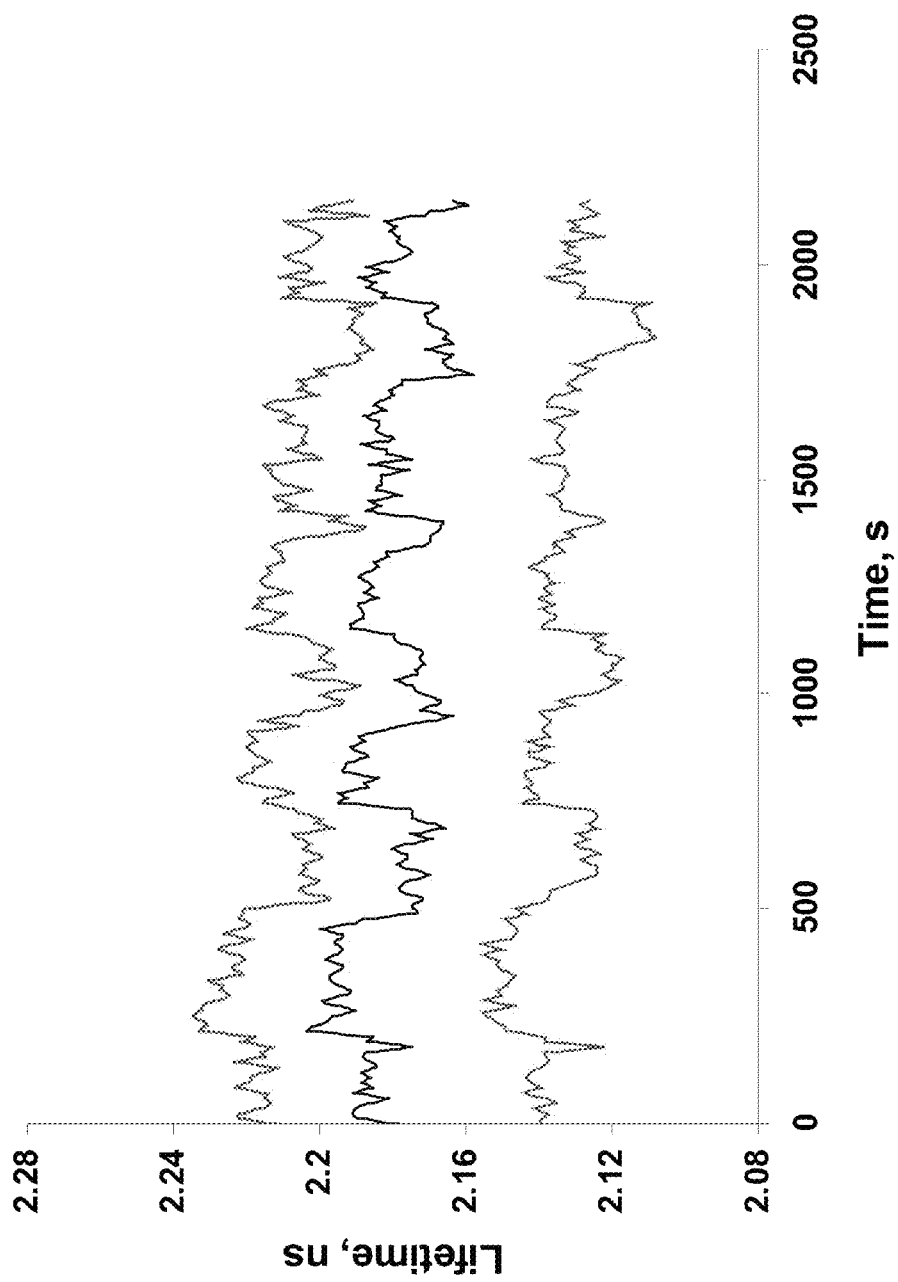
FIG. 24 depicts glucose response in the C2C12 cells maintained at physiological glucose concentration, visualized by the FRET-FLIM measurement. Three traces are from 3 different cells shown in FIG. 23.
Figure 25C:
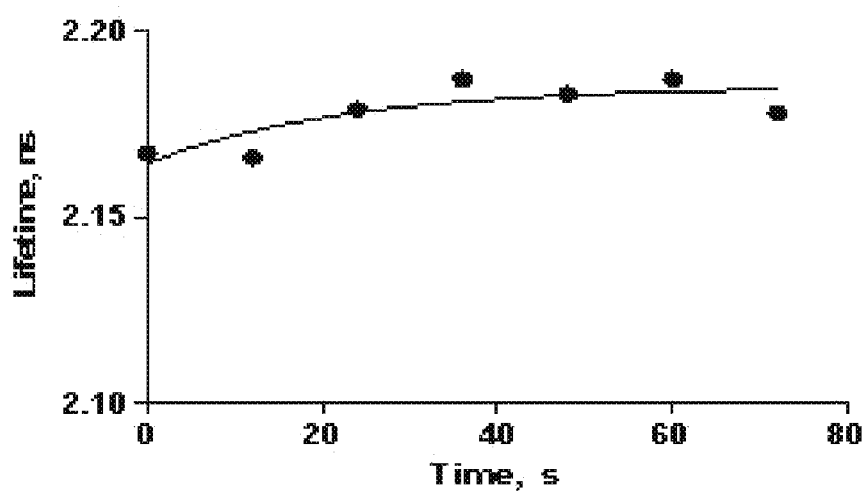
FIG. 25 depicts single exponential fit for the glucose uptake in C2Cl2 cells maintained in physiological glucose levels (5 mM).

These experiments were also performed in C2C12 cells grown under physiological glucose concentrations (5 mM) instead of the 25 mM commonly used in maintaining the cell lines (FIG. 23). FRET-FLIM measurements were then collected as described above (FIG. 24). Representative glucose uptake segments from the traces were fitted by single exponential regression (FIG. 25). Compared to the C2C12 cells grown in the high glucose, the uptake rate here was higher as indicated by the lower Tau values (21.63 ns against 40 ns).

What is claimed is:

1. A pH insensitive glucose indicator protein (GIP) that has a glucose binding dissociation constant ($K_d$) between about 1 mM and about 20 mM comprising:
   a. a glucose binding protein that changes conformation upon exposure to glucose, wherein said glucose binding protein comprises amino acids 24-333 of SEQ ID NO: 1 and has a threonine substituted for phenylalanine at position 39;
   b. at least one pH insensitive fluorescence donor coupled to the glucose binding protein; and
   c. at least one pH insensitive fluorescence acceptor coupled to the glucose binding protein, wherein the conformational changes of the glucose binding protein upon binding or releasing glucose produces a detectable and reversible signal change.

2. The GIP of claim 1, wherein the donor fluorescent protein moiety and the acceptor fluorescent protein moiety are Aequorea-related fluorescent protein moieties.

3. The GIP of claim 1, wherein the donor is enhanced cyan fluorescent protein (ECFP) and the acceptor is yellow fluorescent protein (YFP).

4. The GIP of claim 1, wherein the donor is fused to the N terminus of the glucose binding protein and the acceptor is fused to the C terminus of the glucose binding protein.

5. The GIP of claim 1, further comprising two donors.

6. A pH insensitive glucose indicator protein (GIP) that produces a detectable signal in the presence of from at least 1 mM to about 32 mM glucose comprising:
   (a) a glucose binding protein that changes conformation upon exposure to glucose, wherein said glucose binding protein comprises amino acids 24-333 of SEQ ID NO: 1 and has a threonine substituted for phenylalanine at position 39;
(b) at least one pH insensitive fluorescence donor coupled to the glucose binding protein; and
(c) at least one pH insensitive fluorescence acceptor coupled to the glucose binding protein, wherein the conformational changes of the glucose binding protein upon binding or releasing glucose produces a detectable and reversible signal change.

7. The GIP of claim 6, wherein the donor fluorescent protein moiety and the acceptor fluorescent protein moiety are Aequorea-related fluorescent protein moieties.

8. The GIP of claim 6, wherein the donor is enhanced cyan fluorescent protein (ECFP) and the acceptor is yellow fluorescent protein (YFP).

9. The GIP of claim 6, wherein the donor is fused to the N terminus of the glucose binding protein and the acceptor is fused to the C terminus of the glucose binding protein.

10. The GIP of claim 6, further comprising two donors.

* * * * *